US 8,554,488 B2

(12) United States Patent
Wigler et al.

(10) Patent No.: US 8,554,488 B2
(45) Date of Patent: Oct. 8, 2013

(54) DETERMINING A PROBABILISTIC DIAGNOSIS OF AUTISM BY ANALYSIS OF GENOMIC COPY NUMBER VARIATIONS

(75) Inventors: Michael H. Wigler, Cold Spring Harbor, NY (US); Lakshmi Muthuswamy, Toronto (CA); Jonathan Sebat, San Diego, CA (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 394 days.

(21) Appl. No.: 11/639,712

(22) Filed: Dec. 14, 2006

(65) Prior Publication Data
US 2010/0227768 A1   Sep. 9, 2010

Related U.S. Application Data

(60) Provisional application No. 60/751,353, filed on Dec. 14, 2005, provisional application No. 60/860,280, filed on Nov. 20, 2006.

(51) Int. Cl.
G06F 19/18    (2011.01)
C12Q 1/68     (2006.01)
G06F 19/00    (2011.01)

(52) U.S. Cl.
CPC ............. *G06F 19/34* (2013.01); *G06F 19/18* (2013.01); *C12Q 1/6883* (2013.01); *C12Q 1/6886* (2013.01)
USPC ............................ 702/19; 435/6.11; 435/6.14

(58) Field of Classification Search
None
See application file for complete search history.

(56) References Cited

U.S. PATENT DOCUMENTS

| | | | |
|---|---|---|---|
| 5,436,142 A | 7/1995 | Wigler et al. | |
| 5,501,964 A | 3/1996 | Wigler et al. | |
| 5,569,753 A | 10/1996 | Wigler et al. | |
| 5,876,929 A | 3/1999 | Wigler et al. | |
| 6,159,713 A | 12/2000 | Wigler et al. | |
| 6,251,601 B1 * | 6/2001 | Bao et al. | 435/6 |
| 6,272,479 B1 * | 8/2001 | Farry et al. | 706/13 |
| 6,277,606 B1 | 8/2001 | Wigler et al. | |
| 6,350,576 B1 | 2/2002 | Wigler et al. | |
| 6,647,341 B1 * | 11/2003 | Golub et al. | 702/19 |
| 2003/0082606 A1 | 5/2003 | Lebo et al. | |
| 2004/0137473 A1 | 7/2004 | Wigler et al. | |

(Continued)

FOREIGN PATENT DOCUMENTS

| WO | WO/94/11383 | 5/1994 |
|---|---|---|
| WO | WO/96/19589 | 6/1996 |

(Continued)

OTHER PUBLICATIONS

Lucito R, Healy J, Alexander J, et al.; "Representational Oligonucleotide Microarray Analysis: A High-Resolution Method to Detect Genome Copy Number Variation"; Genome Res. vol. 13; 2003; pp. 2291-2305.*

(Continued)

*Primary Examiner* — Soren Harward
(74) *Attorney, Agent, or Firm* — Gary J. Gershik; Cooper & Dunham LLP

(57) ABSTRACT

The present invention provides methods and compositions related to genomic profiling, and in particular, to assigning probabilistic measure of clinical outcome for a patient having a disease or a tumor using segmented genomic profiles such as those produced by representational oligonucleotide microarray analysis (ROMA).

4 Claims, 45 Drawing Sheets
(32 of 45 Drawing Sheet(s) Filed in Color)

(56) References Cited

U.S. PATENT DOCUMENTS

| | | | |
|---|---|---|---|
| 2004/0197774 A1 | 10/2004 | Wigler et al. | |
| 2005/0032095 A1* | 2/2005 | Wigler et al. | 435/6 |
| 2005/0196799 A1 | 9/2005 | Wigler et al. | |
| 2005/0266444 A1 | 12/2005 | Wigler et al. | |
| 2006/0078917 A1* | 4/2006 | Mishra et al. | 435/6 |
| 2007/0207481 A1 | 9/2007 | Wigler | |
| 2007/0259351 A1* | 11/2007 | Chinitz et al. | 435/6 |

FOREIGN PATENT DOCUMENTS

| | | |
|---|---|---|
| WO | WO/97/22721 | 6/1997 |
| WO | WO/99/23256 | 5/1999 |
| WO | WO/01/83882 | 11/2001 |
| WO | WO/2005/035792 | 4/2005 |
| WO | WO/2007/070640 | 6/2007 |
| WO | WO/2008/016374 A2 | 2/2008 |

OTHER PUBLICATIONS

Aguirre AJ, Brennan C, Bailey G, et al.; "High-resolution characterization of the pancreatic adenocarcinoma genome"; Proc Natl Acad Sci vol. 101 nr 24; Jun. 15, 2004; pp. 9067-9072.*

Sebat J, Lakshmi B, Troge J, et al.; "Large-Scale Copy Number Polymorphism in the Human Genome"; Science vol. 305; Jul. 23, 2004; pp. 525-528.*

Newton MA; "Discovering Combinations of Genomic Aberrations Associated With Cancer"; J Am Stat Assoc vol. 97 nr 460; Dec. 2002; pp. 931-942.*

Smit AFA, Hubley R, Green P; "RepeatMasker Open-3.0"; 1996-2004; <http://www.repeatmasker.org>.*

Barginear, M. F., Bradley, T., Shapira, I. & Budman, D. R. Implications of applied research for prognosis and therapy of breast cancer. Critical Reviews in Oncology/Hematology 65, 223-234 (2008).*

Geyer, F. C., Lopez-Garcia, M. A., Lambros, M. B. & Reis-Filho, J. S. Genetic characterization of breast cancer and implications for clinical management. Journal of Cellular and Molecular Medicine 13, 4090-4103 (2009).*

Grubor, V. et al. Novel genomic alterations and clonal evolution in chronic lymphocytic leukemia revealed by representational oligonucleotide microarray analysis (ROMA). Blood 113, 1294-1303 (2009).*

Iafrate, A. J. et al. Detection of large-scale variation in the human genome. Nature Genetics 36, 949-951 (2004).*

Staden, R. Computer methods to locate signals in nucleic acid sequences. Nucleic Acids Research 12, 505-519 (1984).*

Lander, E. S. & Schork, N. J. Genetic dissection of complex traits. Science (New York, N.Y.) 265, 2037-2048 (1994).*

Muhle, R., Trentacoste, S. V. & Rapin, I. The genetics of autism. Pediatrics 113, e472-e486 (2004).*

Newschaffer, C. J. et al. The epidemiology of autism spectrum disorders. Annual review of public health 28, 235-258 (2007).*

Vorstman, J. A. S. et al. Identification of novel autism candidate regions through analysis of reported cytogenetic abnormalities associated with autism. Molecular Psychiatry 11, 18-28 (2005).*

Zafeiriou, D. I., Ververi, A. & Vargiami, E. Childhood autism and associated comorbidities. Brain & development 29, 257-272 (2007).*

Ahr et al. (2002). Identification of high risk breast-cancer patients by gene expression profiling. Lancet 359, 131-132.

Al Kuraya et al. (2004). Prognostic relevance of gene amplifications and coamplifications in breast cancer. Cancer Res 64, 8534-8540.

Albertson, D.G. (2003). Profiling breast cancer by array CGH. Breast Cancer Res Treat. 78, 289-298.

Balmain et al. (2003). The genetics and genomics of cancer. Nature Genetics Supplement 33, 238-244.

Berns et al. (1995). Association between RB-1 gene alterations and factors of favourable prognosis in human breast cancer, without effect on survival. Int. J. Cancer 64, 140-145.

Chunder et al. (2004). Analysis of different deleted regions in chromosome 11 and their interrelations in early- and late-onset breast tumors: association with cyclin D1 amplification and survival. Diagn. Mol. Pathol. 13, 172-182.

Coquelle et al. (1997). Expression of fragile sites triggers intrachromosomal mammalian gene amplification and sets boundaries to early amplicons. Cell 89, 215-225.

Daruwala et al. (2004). A versatile statistical analysis algorithm to detect genome copy number variation. Proc. Natl. Acad. Sci. U. S. A 101, 16292-16297.

DePinho and Polyak (2004). Cancer chromosomes in crisis. Nature Genetics 36, 932-934.

Edén et al. (2004). "Good Old" clinical markers have similar power in breast cancer prognosis as microarray gene expression profilers. Eur. J Cancer 40, 1837-1841.

Forsslund and Zetterberg (1990). Ploidy level determinations in high-grade and low-grade malignant variants of prostatic carcinoma. Cancer Res 50, 4281-4285.

Forsslund et al. (1996). Near tetraploid prostate carcinoma. Methodologic and prognostic aspects. Cancer 78, 1748-1755.

Garcia et al. (2005). A 1 Mb minimal amplicon at 8p11-12 in breast cancer identifies new candidate oncogenes. Oncogene 24, 5235-5245.

Gisselsson et al. (2000). Chromosomal breakage-fusion-bridge events cause genetic intratumor heterogeneity. Proc Natl Acad Sci U S A 97, 5357-5362.

Hellman et al. (2002). A role for common fragile site induction in amplification of human oncogenes. Cancer Cell 1, 89-97.

Jarvinen and Liu (2003). HER-2/neu and topoisomerase IIalpha in breast cancer. Breast Cancer Res Treat. 78, 299-311.

Kallioniemi et al. (1992a). Comparative genomic hybridization for molecular cytogenetic analysis of solid tumors. Science 258, 818-821.

Kallioniemi et al. (1992b). Detection of retinoblastoma gene copy number in metaphase chromosomes and interphase nuclei by fluorescence in situ hybridization. Cytogenet. Cell Genet. 60, 190-193.

Kallioniemi et al. (1992c). ERBB2 amplification in breast cancer analyzed by fluorescence in situ hybridization. Proc. Natl. Acad. Sci. U. S. A 89, 5321-5325.

Kallioniemi et al. (1994). Detection and mapping of amplified DNA sequences in breast cancer by comparative genomic hybridization. Proc Natl Acad Sci U S A 91, 2156-2160.

Knoop et al. (2005). Retrospective analysis of topoisomerase IIa amplifications and deletions as predictive markers in primary breast cancer-patients randomly assigned to cyclophosphamide, methotrexate, and fluorouracil or cyclophosphamide, epirubicin, and fluorouracil. Danish Breast Cancer Cooperative Group. J. Clin Oncol. 23, 7483-7490.

Kronenwett et al. (2004). Improved grading of breast adenocarcinomas based on genomic instability. Cancer Res 64, 904-909.

Lage et al. (2003). Whole genome analysis of genetic alterations in small DNA samples using hyperbranched strand displacement amplification and array-CGH. Genome Res 13, 294-307.

Loo et al. (2004). Array comparative genomic hybridization analysis of genomic alterations in breast cancer subtypes. Cancer Res 64, 8541-8549.

Lucito R, Healy J, Alexander J, Reiner A, Esposito D, Chi M, Rodgers L, Brady A, Sebat J, Troge J, West JA, Rostan S, Nguyen KC, Powers S, Ye KQ, Olshen A, Venkatraman E, Norton L, Wigler M, "Representational oligonucleotide microarray analysis: a high-resolution method to detect genome copy number variation," Genome Res. Oct. 2003;13(10):2291-305. Epub Sep. 15, 2003.

Madjd et al. (2005). Total loss of MHC class I is an independent indicator of good prognosis in breast cancer. Int. J. Cancer 117, 248-255.

McClintock (1938). The production of homozygous deficient tissues with mutant characteristics by means of the aberrant mitotic behavior of ring-shaped chromosomes. Genetics 23, 315-376.

McClintock (1941). The stability of broken ends of chromosomes in Zea Mays. Genetics 26, 234-282.

Menard et al. (2001). HER2 as a prognostic factor in breast cancer. Oncology 61, 67-72.

(56) References Cited

OTHER PUBLICATIONS

Navin et al. (2006). PROBER : oligonucleotide FISH probe design software. Bioinformatics. 22:2437-2438.
Nessling et al. (2005). Candidate genes in breast cancer revealed by microarray-based comparative genomic hybridization of archived tissue. Cancer Res. 65, 439-447.
Olshen et al. (2004). Circular binary segmentation for the analysis of array-based DNA copy number data. Biostat 5, 557-572.
Ormandy et al. (2003). Cyclin D1, EMS1 and 11q13 amplification in breast cancer. Breast Cancer Res Treat. 78, 323-335.
Paik et al. (2004). A multigene assay to predict recurrence of tamoxifen-treated, node-negative breast cancer. N Engl J Med 351, 2817-2826.
Perou et al. (2000). Molecular portraits of human breast tumours. Nature 406, 747-752.
Pollack et al. (2002). Microarray analysis reveals a major direct role of DNA copy number alteration in the transcriptional program of human breast tumors. Proc Natl Acad Sci U S A 99, 12963-12968.
Ried et al. (1995). Comparative genomic hybridization of formalin-fixed, paraffin-enbedded breast tumors reveals different patterns of chromosomal gains and losses in fibroadenomas and diploid and aneuploid carcinomas. Cancer Res 5, 5415-5423.
Ried et al. (1997). Tumor cytogenetics revisited: comparative genomic hybridization and spectral karyotyping. J. Mol. Med. 75, 801-814.
Sebat J, Lakshmi B, Troge J, Alexander J, Young J, Lundin P, Maner S, Massa H, Walker M, Chi M, Navin N, Lucito R, Healy J, Hicks J, Ye K, Reiner A, Gilliam TC, Trask B, Patterson N, Zetterberg A, Wigler M, "Large-scale copy number polymorphism in the human genome," Science. Jul. 23, 2004;305(5683):525-8.
Shuster et al. (2000). A consistent pattern of RIN1 rearrangements in oral squamous cell carcinoma cell lines supports a breakage-fusion-bridge cycle model for 11q13 amplification. Genes Chromosomes Cancer 28, 153-163.
Slamon et al. (1989). Studies of the HER-2/neu proto-oncogene in human breast and ovarian cancer. Science 244, 707-712.
Sorlie et al. (2001). Gene expression patterns of carcinomas distinguish tumor subclasses with clinical implications. Proc Natl Acad Sci U S A 98, 10869-10874.
Sotiriou, C. (2003). Breast cancer classification and prognosis based on gene expression profiles from a population-based study. Proc Natl Acad Sci U S A 100, 10393-10398.
Tanaka et al. (2005). Widespread and nonrandom distribution of DNA palindromes in cancer cells provides a structural platform for subsequent gene amplification. Nat. Genet. 37, 320-327.
Tirkkonen et al. (1998). Molecular cytogenetics of primary breast cancer by CGH. Genes Chromosomes Cancer 21, 177-184.
van't Veer et al. (2002). Gene expression profiling predicts clinical outcome of breast cancer. Nature 415, 530-536.
van de Vijver et al. (1987). Amplification of the neu (c-erbB72) oncogene in human mammmary tumors is relatively frequent and is often accompanied by amplification of the linked c-erbA oncogene. Mol. Cell Biol. 7, 2019-2023.
Wiedswang et al. (2003). Detection of isolated tumor cells in bone marrow is an independent prognostic factor in breast cancer. J. Clin Oncol. 21, 3469-3478.
Restriction Requirement issued Oct. 17, 2008 in connection with U.S. Appl. No. 11/639,674, filed Dec. 14, 2006.
Office Action issued Jun. 11, 2009 in connection with U.S. Appl. No. 11/639,674, filed Dec. 14, 2006.
Notification of Concerning Transmittal of International Preliminary Report on Patentability, issued Jun. 26, 2008, in connection with International Application No. PCT/US06/047913.
Hicks et al. High-resolution ROMA CGH and FISH analysis of aneuploid and diploid breast tumors. Cold Spring Harbor Symposia on Quantitative Biology (2005) 70:51-63.
Hicks, D. G,, et al. The incidence of topoisomerase II-alpha genomic alterations in adenocarcinoma of the breast and their relationship to human epidermal growth factor receptor-2 gene amplification: A Fluorescence in Situ Hybridization Study. Human Pathology (2005) 36:348-356.
Hicks, J., et al. Novel patterns of genome rearrangement and their association with survival in breast cancer. Genome Res. Dec. 2006;16(12):1465-79.
Lakshmi, B., et al. Mouse genomic representational oligonucleotide microarray analysis: detection of copy number variations in normal and tumor specimens. Proc Natl Acad Sci U S A. Jul. 25, 2006;103(30):11234-9. Epub Jul. 14, 2006.
Lucito, R. et al. Detecting gene copy number fluctuations in tumor cells by microarray analysis of genomic representations. Genome Res. Nov. 2000;10(11):1726-36.
Lucito, R. et al. Genetic analysis using genomic representations. Proc Natl Acad Sci U S A. Apr. 14, 1998; 98(8) :4487-92.
Zender, L., et al. Identification and validation of oncogenes in liver cancer using an integrative oncogenomic approach. Cell. Jun. 30, 2006; 125(7) :1253-67.
Jacobson (Genes, Chromosome, and Cancer, 2005, 40:19-31).
Official Action issued Apr. 2, 2009 in connection with European Patent Application No. 06851479.3.
Request for Further Processing and Response to Apr. 7, 2009 Official Action filed Dec. 22, 2009 in connection with European Patent Application No. 06851479.
Final Office Action issued Apr. 14, 2010 in connection with U.S. Appl. No. 11/639,674, filed Dec. 14, 2006.
Orsetti, B., et al. Genomic and expression profiling of chromosome 17 in breast cancer reveals complex patterns of alterations and novel candidate genes. Cancer Res. 64(18):6453-60. (2004).
Albrecht, B. et al. Array-based comparative genomic hybridization for the detection of DNA sequence copy number changes in Barrett's adenocarcinoma. J Pathol. 203(3):780-8 (2004).
Request for Further Processing and Response to Apr. 2, 2009 Official Action filed Dec. 22, 2009 in connection with European Patent Application No. 06845431.3.
Jul. 14, 2010 Amendment in Response to Apr. 14, 2010 Final Office Action submitted in connection with U.S. Appl. No. 11/639,674, filed Dec. 14, 2006.
Jul. 23, 2010 Advisory Action issued in connection with U.S. Appl. No. 11/639,674, filed Dec. 14, 2006.
Oct. 14, 2010 Amendment and Supplemental Information Disclosure Statement as a Submission Accompanying a RCE, Summary of Aug. 17, 2010 Telephonic Examiner Interview, and Petition for Three-Month Extension of Time submitted in connection with U.S. Appl. No. 11/639,674, filed Dec. 14, 2006.
Jan. 21, 2011 Official Action issued in connection with European Application No. 06845431.3.
May 31, 2011 Response to Jan. 21, 2011 Official Action submitted in connection with European Application No. 06845431.3.
Feb. 8, 2011 Office Action issued in connection with Israeli Patent Application No. 192199 (including English translation).
Supplemental Response to Apr. 7, 2009 Communication filed Feb. 21, 2011 in connection with European Patent Application No. EP06851479.3.
May 13, 2011 Office Action issued in connection with European Patent Application No. EP06851479.3.
Official Action issued Apr. 2, 2009 in connection with European Patent Application No. 06845431.3.
Official Action issued Apr. 7, 2009 in connection with European Patent Application No. 06851479.3.
Kallionlemi, OP et al. (1993) "Comparative genomic hybridization: a rapid new method for detecting and mapping DNA amplification in tumors," Semin Cancer Biol. 4(1):41-6.
The Autism Society, *About Autism*, http://asa.pub30.convio.net/about-autism/ (last visited Aug. 24, 2012).
Howlin et al. (2004) "Adult outcome for children with autism" Journal of Child Psychology and Psychiatry, 45:212-229 (Abstract Only).
Billstedt et al. (2005) "Autism after Adolescence: Population-based 13-22-year Follow-up Study of 120 Individuals with Autism Diagnosed in Childhood" Journal of Autism and Developmental Disorders, 35(3):351-360 (Abstract Only).
American Academy of Pediatrics, Committee on Children with Disabilities, Sandler, A.D., Chairperson, (2001) "Technical Report: The

(56) References Cited

OTHER PUBLICATIONS

Pediatrician's Role in the Diagnosis and Management of Autistic Spectrum Disorder in Children" Pediatrics, 107(5); e85 (pp. 1-18).
Jan. 21, 2011 Communication from the Examining Division, issued in connection with European Patent Application No. 06845431.3.

May 31, 2011 Response to Communication from the Division, Examining filed in connection with European Patent Application No. 06845431,3.
Sep. 23, 2011 Response to Communication from the Examining Division, filed in connection with European Patent Application No. 06851479.3.

* cited by examiner

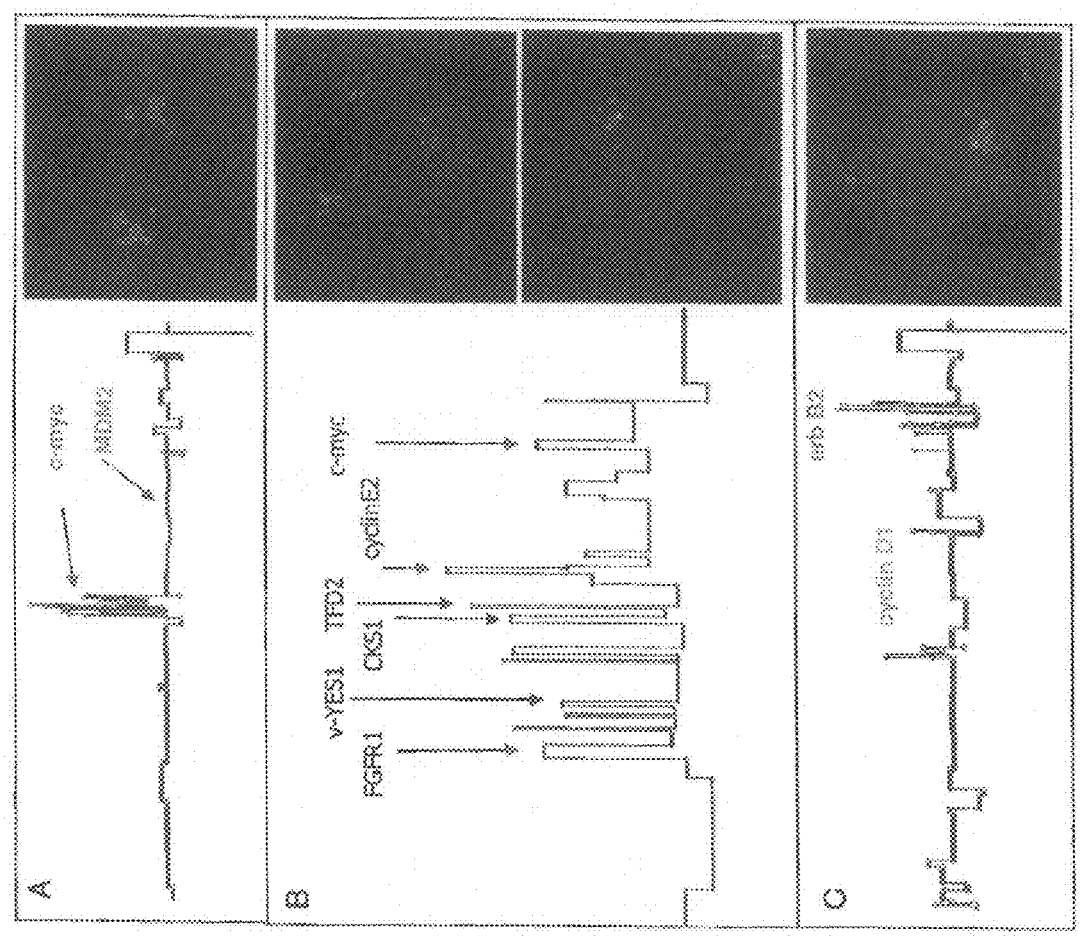

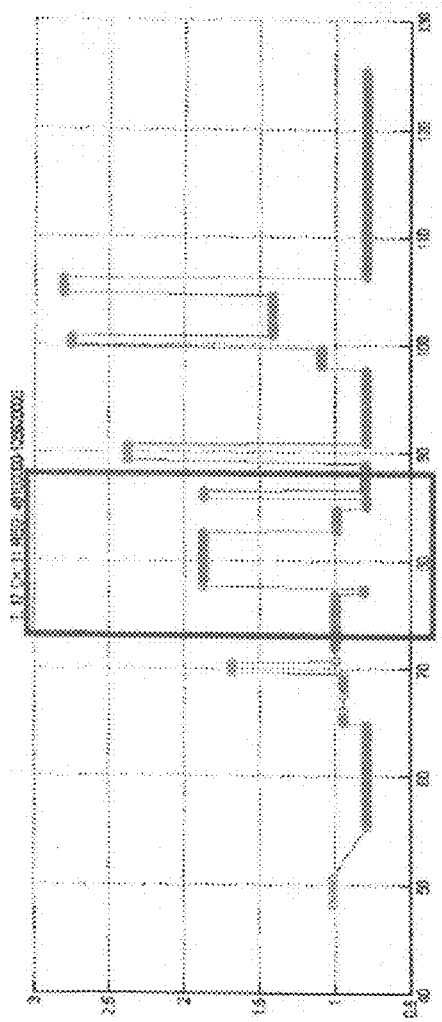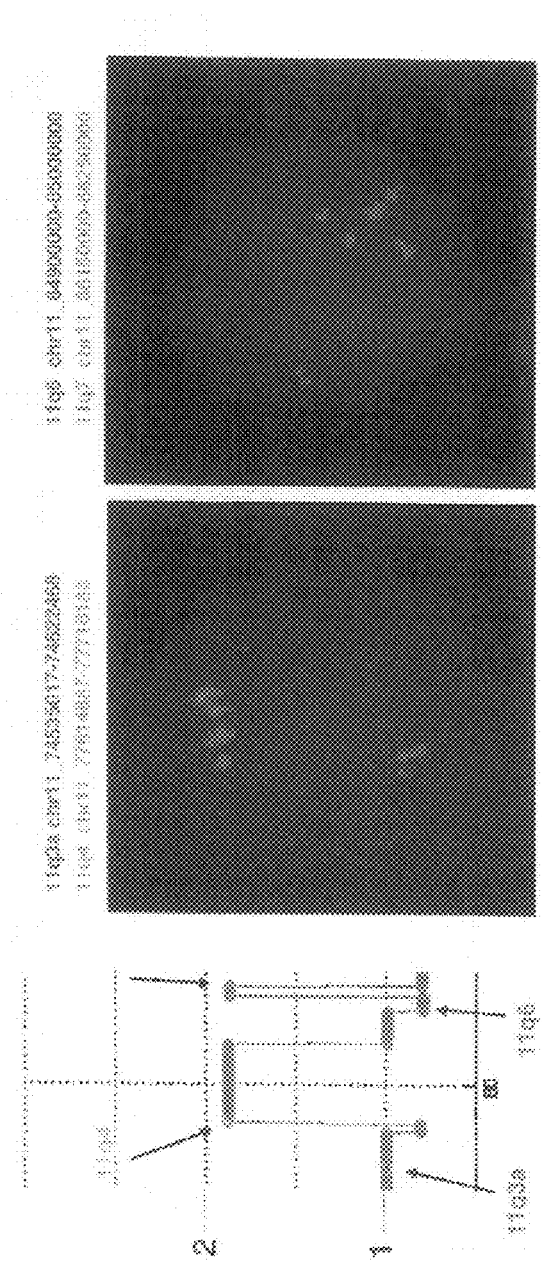
FIG. 6E

| Perturbation Index Value | P-Value | Strength of Association Value | Relative Risk |
|---|---|---|---|
| [1,] | 0.008 | 3.396357e-04 | 0.20735144 | 2.526132 |
| [2,] | 0.016 | 3.208695e-06 | 0.11511483 | 3.265306 |
| [3,] | 0.024 | 2.333362e-07 | 0.08894734 | 3.571429 |
| [4,] | 0.032 | 1.141996e-05 | 0.10844212 | 2.955466 |
| [5,] | 0.040 | 2.532106e-06 | 0.09896698 | 3.115789 |
| [6,] | 0.048 | 3.105921e-06 | 0.07753419 | 3.139130 |
| [7,] | 0.056 | 8.226442e-06 | 0.08578385 | 3.000000 |
| [8,] | 0.064 | 7.876568e-03 | 0.18520750 | 2.200000 |
| [9,] | 0.072 | 7.876568e-03 | 0.18520750 | 2.200000 |
| [10,] | 0.080 | 7.876568e-03 | 0.18520750 | 2.200000 |
| [11,] | 0.088 | 3.039742e-02 | 0.24180735 | 1.984619 |
| [12,] | 0.096 | 5.760382e-02 | 0.28061767 | 1.870968 |
| [13,] | 0.104 | 1.055418e-01 | 0.33043701 | 1.750000 |
| [14,] | 0.112 | 4.647053e-02 | 0.24424775 | 1.946875 |
| [15,] | 0.120 | 4.647053e-02 | 0.24424775 | 1.946875 |
| [16,] | 0.128 | 4.647053e-02 | 0.24424775 | 1.946875 |
| [17,] | 0.136 | 4.647053e-02 | 0.24424775 | 1.946875 |
| [18,] | 0.144 | 1.486651e-01 | 0.29328484 | 1.818182 |

Figure 19

| Biopsy | Status | Mean segment ratio for probe$_i$ | | Biopsy | Status | Mean segment ratio for probe$_i$ |
|---|---|---|---|---|---|---|
| 1 | S | 1.01 | | 3 | D | 4.18 |
| 2 | D | 2.37 | | 2 | D | 2.37 |
| 3 | D | 4.18 | rank → | 4 | S | 1.14 |
| 4 | S | 1.14 | | 1 | S | 1.01 |
| 5 | S | 0.98 | | 6 | S | 0.99 |
| 6 | S | 0.99 | | 5 | S | 0.98 |

DETERMINING A PROBABILISTIC DIAGNOSIS OF AUTISM BY ANALYSIS OF GENOMIC COPY NUMBER VARIATIONS

CROSS REFERENCE TO RELATED APPLICATIONS

This application claims the benefit of and priority to U.S. Provisional Application No. 60/751,353, filed on Dec. 14, 2005, and No. 60/860,280, filed on Nov. 20, 2006, the contents of which are hereby incorporated by reference in their entirety.

STATEMENT REGARDING GOVERNMENT FUNDING

This invention was made with government support under 5R01-CA078544-07 awarded by the U.S. National Institutes of Health, and W81XWH04-1-0477, W81XWH-05-1-0068, and W81XWH-04-0905 awarded by the U.S. Department of Army. The U.S. government has certain rights in the invention.

BACKGROUND OF THE INVENTION

Global methods for genomic analysis, such as karyotyping, determination of ploidy, and more recently comparative genomic hybridizaton (CGH) (Feder et al., 1998, Cancer Genet. Cytogenet, 102:25-31; Gebhart et al., 1998, Int. J. Oncol. 12:1151-1155; Larramendy et al., 1997, Am. J. Pathol. 151:1153-1161; Lu et al., 1997, Genes Chromosomes Cancer 20:275-281) have provided useful insights into the pathophysiology of cancer and other diseases or conditions with a genetic component, and in some instances have aided diagnosis, prognosis and selection of treatment. However, those methods do not afford a level of resolution of greater than can be achieved by standard microscopy, or about 5-10 megabases. Moreover, while many particular genes that are prone to mutation can be used as probes to interrogate the genome in very specific ways (e.g., Ford et al., 1998, Am. J. Hum. Genet. 62:676-689; Gebhart et al., 1998, Int. J. Oncol. 12:1151-1155; Hacia et al., 1996, Nat. Genet. 14:441-447), this one-by-one query is an inefficient and incomplete method for genetically typing cells.

The microarray or "chip" technology has made it possible to contemplate obtaining a high resolution global image of genetic changes in cells. Two general approaches can be conceived. One is to profile the expression pattern of the cell using microarrays of cDNA probes (e.g., DeRisi et al., 1996, Nat. Genet. 14:457-460). The second approach is to examine changes in the cancer genome itself, which has several advantages over the expression profiling approach. First, DNA is more stable than RNA, and can be obtained from poorly handled tissues, and even from fixed and archived biopsies. Second, the genetic changes that occur in the cancer cell, if their cytogenetic location can be sufficiently resolved, can be correlated with known genes as the databases of positionally mapped cDNAs mature. Thus, the information derived from such an analysis is not likely to become obsolete. The nature and number of genetic changes can provide clues to the history of the cancer cell. Third, a high resolution genomic analysis may lead to the discovery of new genes involved in the etiology of the disease or disorder of interest.

DNA-based methods for global genome analysis, for example, measuring changes in copy number, include fluorescent in situ hybridization (FISH), the BAC array, and cDNA arrays. FISH has been used clinically to evaluate amplification at the ErbB-2 locus in breast cancer (Tkachuk et al., 1990, Science 250:559-562; Bartlett and Mallon, 2003, J. Pathology 199:418-423), but FISH relies on having a probe that hybridizes to a single locus that may be important in selecting cancer therapy. A major disadvantage of the BAC array and the cDNA array methods is low resolution.

WO0183822 and WO00923256 disclose certain methods and compositions to solve the problems associated with using microarrays to conduct DNA-based global genome analysis, particularly of a genome based on DNA extracted from scant, nonrenewable sources such as tumor or cancer tissue samples. These patent applications relate to a technology termed Representational Oligonucleotide Microarray Analysis (ROMA), a powerful tool for detecting genetic rearrangements such as amplifications, deletions, and sites of breakage in cancer and normal genomes, by comparative genomic hybridization (CGH).

These genomic profiling methods provide useful tools to detect and identify chromosomal alterations, which are hallmarks of cancer cells as well as of other diseases such as certain degenerative and neurobehavioral diseases. See e.g., Gericke, Med. Hypotheses. 2006; 66(2):276-285, Epub 2005 Sep. 22. In humans, non-cancerous cells contain two complete copies of each of 22 chromosomes plus to two X chromosomes in females, or one X and one Y chromosomes in males. Cancer cells exhibit a wide range of genomic rearrangements, including deletion (e.g., lowering copy number from 2 to 1 or 0), duplication (e.g., raising copy number from 2 to 3 or 4) of DNA segments, amplification of DNA segments up to 60 copies, and duplication or triplication of the entire set of chromosomes (i.e., aneuploidy). Comparing genomic profiles between cancer cells and normal cells from a particular patient, or between cancer cells from samples from different patients with different disease progression states and who have undergone different treatments would provide correlations between particular genetic alterations with particular cancer or patient traits. Such correlations would be useful in cancer diagnosis, cancer patient stratification for any given therapy, and predicting clinical outcome based on a patient's genomic profile. Therefore, a need exists for new methods that would make such correlation feasible.

Many diseases and conditions involve alterations at the chromosomal level. Many cancers, for example, involve genomic alterations. As cancers evolve, their genomes undergo many alterations, including point mutations, rearrangements, deletions and amplifications, which presumably alter the ability of the cancer cell to proliferate, survive and spread in the host (Balmain et al., 2003; DePinho and Polyak, 2004). Other diseases that may involve genomic rearrangements include, but are not limited to, autism and schizophrenia. Diseases that involve certain genetic predisposition may also involve genomic rearrangements, such as obesity. For other diseases (such as certain degenerative diseases and neurobehavioral diseases), genomic changes or rearrangements are presumably deleterious to cell growth and/or survival.

An understanding of these chromosomal level alterations or genomic changes will allow the design of more rational therapies and, by providing precise diagnostic criteria, allow fitting the correct therapy to each patient according to need. For example, primary breast cancers in particular exhibit a wide range of outcomes and degrees of benefit from systemic therapies, which are incompletely predicted by conventional clinical and clinico-pathological features. This is especially apparent in the case of small primaries without axillary lymph node involvement, which usually have a good prognosis but are sometimes associated with eventual metastatic dissemination and inevitable lethality.

Breast tumors, for example, have long been known to suffer multiple genomic rearrangements during their development and thus it is reasonable to hypothesize that clinical heterogeneity may be caused by the existence of genetically distinct subgroups. One common approach to the molecular characterization of breast cancer has been "expression profiling", measuring the entire transcriptome by microarray hybridization. Expression profiling has been very effective at revealing phenotypic subtypes of breast cancer and clinically useful diagnostic patterns of gene expression in tumors (Ahr et al., 2002; van't Veer et al., 2002; Paik et al., 2004; Perou et al., 2000; Sorlie et al., 2001; Sotiriou, 2003). Expression profiling does not look directly at underlying genetic changes, and its dependence on RNA, a fragile molecule, creates some problems in standardization and cross validation of microarray platforms. Moreover, variation in the physiological context of the cancer within the host, such as the proportion of normal stroma and the degree of inflammatory response, or the degree of hypoxia, as well as methods used for extraction and preservation of sample, are all potentially confounding factors (Eden et al., 2004).

Direct analysis of the tumor genome provides an alternative and perhaps, complementary, means of comparing breast tumors by revealing the genetic events accumulated during tumor progression. A long-term genomic study has been initiated and conducted for clinically well-defined sets of breast cancer patients with ROMA (Lucito et al., 2003). ROMA is based on the principle that noise in microarray hybridization can be significantly reduced by reducing the complexity of the labeled DNA target in the hybridization mix. In its current configuration ROMA uses a "representation" of the genome created by PCR amplification of the smallest fragments of a BglII restriction digest. The representation contains less than 3% the complexity of the normal human genome and is specifically matched with a unique microarray containing over 83,000 oligonucleotide probes designed to pair with the amplified fragments. Coupled with an efficient edge-detection or segmentation algorithm, ROMA yields highly precise profiles of even closely spaced amplicons and deletions. Currently, ROMA is capable of detecting the breakpoints of chromosomal events at a resolution of 50 kb.

ROMA is a powerful tool for genomic profiling. Nevertheless, there remains a need for improvements in analysis of data obtained by ROMA as well as by other methods that represent segments of the genome. With such improved analytical tools and methods, one will be better able to manipulate high resolution genomic data analysis and apply it to the clinical, therapeutic setting. Such improved analytical tools and methods will also continue to improve our ability to track genetic events and to understand their effects on the etiology of disease.

The first global studies capable of resolving deletions and amplifications combined comparative genomic hybridization (CGH) and cytogenetics (Kallioniemi et al., 1992a; Kallioniemi et al., 1992b; Kallioniemi et al., 1992c) and this approach has been applied to breast tumors (Kallioniemi et al., 1994; Tirkkonen et al., 1998; Ried et al., 1997). Subsequently, microarray methods employing CGH have increased resolution and reproducibility, and improved throughput (Albertson, 2003; Lage et al., 2003; Ried et al., 1995; Pollack et al., 2002). These published microarray studies have largely validated the results of cytogenetic CGH, but have not had sufficient resolution to significantly improve our knowledge of the role of genetic events in the etiology of disease, nor assist in the treatment of the patient. On the other hand, knowledge of specific genetic events, like amplification of ERBB2, as studied by FISH or Q-PCR, has been clinically useful (van, V et al., 1987; Slamon et al., 1989; Menard et al., 2001). ROMA provides an extra measure of resolution in genomic analysis that might be useful in clinical evaluation, as well as delineating loci important in disease evolution.

SUMMARY OF THE INVENTION

The present invention solves the problems discussed above by providing the following illustrative methods and compositions.

A first aspect of the present invention relates to a method for assigning a probabilistic measure of a clinical outcome for an individual patient having a disorder, condition or disease, such as a tumor. In certain embodiments, the method includes obtaining a segmented genomic profile, $GP_{(indvl)}$, of DNA extracted from one or more affected or diseased cells, e.g., tumor cells, from a first individual patient, said $GP_{(indvl)}$ comprising information on the copy number of a plurality of discrete segments of the genome, or one or more portions of the genome; wherein, when relative copy number as a function of genomic position is plotted for a plurality of genomic segments within said $GP_{(indvl)}$, a particular geometric pattern may be observed. The method further includes comparing part or all of said $GP_{(indvl)}$ and/or part or all of its associated geometric pattern to a database or clinical annotation table $GP_{(DB)}$ comprising a plurality of entries. In specific embodiments, each entry in the database or clinical annotation table includes clinical information pertaining to a patient or the patient's tumor or disease and one or more quantitative measures derived from a genomic profile of the patient. Accordingly, a similarity between part or all of the individual patient's $GP_{(indvl)}$ or its particular geometric pattern and that of one or more quantitative measures derived from a genomic profile of the $GP_{(DB)}$ database or clinical annotation table is evaluated and used to assign a probabilistic measure of an outcome or a set of outcomes to said individual patient.

In another aspect, a method of the present invention includes obtaining a segmented genomic profile, $GP_{(indvl)}$, of DNA extracted from one or more affected or diseased cells, e.g., tumor cells, from a first individual patient, said $GP_{(indvl)}$ comprising information on the copy number of a plurality of discrete segments of the genome or one or more portions of the genome. The method also includes applying to said $GP_{(indvl)}$ or a portion thereof a mathematical function that provides a measure of one or more of: (i) the number of said discrete segments, (ii) the lengths or areas of said discrete segments, and (iii) the distribution of the lengths or areas of at least two adjacent segments, thereby obtaining a genomic perturbation index value, PI(i), or firestorm index, FSI, related to the proximity and frequency of breakpoints within one or more genomic regions from the genome of the individual patient. The method may further include comparing said perturbation index value PI(i) to a database or clinical annotation table comprising a plurality of entries, $GP_{(DB)}$, each entry comprising (i) clinical information pertaining to a different patient and that patient's tumor or disease; and (ii) one or more quantitative measures derived from a genomic profile of the different patient that can generate a genomic perturbation index value. Accordingly, a similarity between the individual patient's genomic perturbation index value PI(i) and one or more perturbation index values of the $PI_{(DB)}$ database or clinical annotation table is evaluated and used to assign a probabilistic measure of an outcome or a set of outcomes to said individual patient.

In certain embodiments, a method of the invention may further include the step of identifying one or more specific genomic segments whose relative copy number correlates with clinical outcome.

A further aspect of the present invention provides a method for masking the contribution of copy number polymorphism among individuals in a segmented genomic profile representing chromosome rearrangements present in DNA derived by measuring relative copy number of a plurality of discrete segments of the genome or a portion of the genome. In certain embodiments, the method includes generating a mask, the generating step including: providing a set of non-cancer genomes and determining at least one contiguous set of probes in the set of non-cancer genomes satisfying at least two predetermined conditions. In certain embodiments, the method further includes applying the mask to provide a mask of the segmented genomic profile, the applying step including: determining at least one contiguous group of segments in a segmented profile of an individual that is a subset within one of the at least one contiguous set of probes; and changing the value of a segment ratio of at least one segment within the at least one contiguous group of segments.

Another aspect of the present invention provides a genomic segment useful as a copy number probe for assessing probable clinical outcome for an individual patient having a tumor associated with breast cancer. In certain embodiments, a genomic segment corresponds or relates to: an EGFR locus as shown, e.g., in FIG. 15 or Table 8, which indicates chromosomal positions of probes specific to the EGFR locus; a Her2 locus as shown, e.g., in FIG. 4 or Table 8, which indicates chromosomal positions of probes specific to the Her2 locus; and an INK4 (CDKN2A) locus located at chromosome 9p21.97 or, e.g., as shown in Table 8, which indicates chromosomal positions of probes specific to the CDKN2A locus.

A further aspect of the present invention provides a method for assessing probable clinical outcome for an individual patient having a disorder, condition or disease, such as a tumor, the method including: obtaining a segmented genomic profile, $GP_{(i)}$, of DNA extracted from one or more diseased (e.g., tumor) cells from a first individual patient, said $GP_{(i)}$ representing a subpopulation of chromosome rearrangements present in the extracted diseased (e.g., tumor) cell DNA derived by measuring relative copy number of one or more segments representing a portion of the genome comprising one or more of the genomic segment of the present invention.

Another aspect of the present invention provides a method for identifying one or more potential oncogenic loci associated with a particular tumor type or disease. In certain embodiments, the method includes the steps of comparing genomic profiles generated according to the methods of present invention, and identifying as oncogenic loci segments of the genome that correlate with high probability, alone or in combination, to probable clinical outcome for an individual patient having the particular tumor type or disease.

Another aspect of the present invention relates to a method for determining whether a subject tumor in an individual patient is related to a tumor that occurred earlier (earlier tumor) in the same patient. In certain embodiments, the method includes obtaining a segmented genomic profile, $GP_{(T2)}$, of DNA extracted from one or more cells of the subject tumor, said $GP_{(T2)}$ representing chromosome rearrangements present in the extracted DNA derived by measuring relative copy number of a plurality of discrete segments of the genome or one or more portions of the genome. In certain embodiments, the method further includes comparing the $GP_{(T2)}$ to a $GP_{(T1)}$, wherein the $GP_{(T1)}$ is a segmented genomic profile of DNA extracted from one or more cells of the same patient's earlier tumor and representing chromosomal rearrangements present in DNA extracted from the earlier tumor derived by measuring relative copy number of a plurality of discrete segments of the genome or a portion of the genome. Accordingly, a match in one or more chromosomal rearrangements present in both $GP_{(T2)}$ and $GP_{(T1)}$ is used to determine that the subject tumor is related to the earlier tumor.

In another aspect, the present invention provides a method for determining whether two or more tumors present in an individual patient at the same time are related to each other. In certain embodiments, the method includes obtaining a segmented genomic profile, $GP_{(Ti)}$, of DNA extracted from one or more cells of each respective tumor, each $GP_{(Ti)}$ representing chromosome rearrangements present in the extracted DNA derived by measuring relative copy number of a plurality of discrete segments of the genome or one or more portions of the genome. The method may further include comparing each $GP_{(Ti)}$ to each other $GP_{(Ti)}$; and accordingly, a match in one or more chromosomal rearrangements present in two or more $GP_{(Ti)}$s is used to determine that one tumor is related to the other tumor.

A further aspect of the present invention relates to a method for determining the origin of one or more tumors. In certain embodiments, said one or more tumors are present in a patient. In other alternative or further embodiments, said one or more tumors are present in a biological sample. The method may include the steps of obtaining a segmented genomic profile, $GP_{(Ti)}$, of DNA extracted from one or more cells of each respective tumor, each $GP_{(Ti)}$ representing chromosome rearrangements present in the extracted DNA derived by measuring relative copy number of a plurality of discrete segments of the genome or a portion of the genome; and comparing each $GP_{(Ti)}$ to one or more segmented genomic profiles in a database or clinical annotation table for tumors of known origin. Accordingly, a match in one or more chromosomal rearrangements present in one or more $GP_{(Ti)}$ is used to determine the origin of said one or more tumors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A shows FISH analysis of multiply amplified regions. Photographs show two color FISH images of loci labeled in the ROMA profiles. A. Tumor WZ11 showing a 'firestorm' of amplification on chromosome 8 (Chr8) and cluster of spots compared to single-copy MDM2. B. Enlarged view of Chr8 showing location of amplicons and putative oncogenes. FISH images show results of probing two separate pairs of amplicons within the same region. C. Tumor WZ20 where amplicons appear on different chromosomes. The FISH image shows that the repeated loci occupy separate regions of the nucleus.

FIGS. 6C-6E show the validation of peaks and valleys in ROMA profiles by interphase FISH.

FIG. 6C shows the profile of tumor WZ19 in which two firestorms are observed on chromosomes 11q and 17q. In contrast to the overlapping clusters shown in panel A, amplifications on unrelated arms visualized using FISH probes for CCN D1 and ERBB2 cluster independently in the nucleus.

FIG. 6D shows the expanded ROMA profile of a firestorm on chromosome 8 in the diploid tumor WZ11. The graph shows the normalized raw data (grey) and segmented profile (red) along with the genes for which the probes shown in the FISH images were constructed. Several distinct conditions are exemplified in the images. First, the ROMA profile indicates that the 8p arm is deleted distal to the 8p12 cytoband yielding a single copy of DBC1(green), but >10 tightly clustered copies of BAG4, which is located in the frequently amplified 8p12 locus (Garcia et al., 2005). Tight clusters of multiple copies corresponding to ROMA peaks are also shown in the FISH images for CKS1, MYC, TPD52 and the uncharacterized ORF AK096200. Note that the FISH signals corresponding to distinct loci cluster together irrespective of their distance on the same arm (CKS1/MYC) or across the centromere (BAG4/AK096200). Finally the spaces between ROMA peaks on 8q, exemplified by NBS1, uniformly showed two copies as indicated by the ROMA profile.

FIG. 6E shows the expanded view of the centromere and 11q arm from diploid tumor WZ17 showing correspondence of the copy number as measured by FISH with the copy number predicted by the ROMA profile. The Y-axis represents the segmented ratios of sample versus control. Chromosome position on the X-axis is in megabases according to Freeze 15 (April, 2003) on the UCSC Genome Browser (Karolchik et al., 2003). FISH probes were amplified from primers identified from specific loci using PROBER software. The insert outlined in black is magnified to show specific details. Comparative data for the probes shown in black are publicly available, e.g., on the interne. In the boxed region, note that the non-amplified regions the ROMA profile predicts two copies of the arm proximal to amplification. Consistent with the profile, the FISH image shows two copies of probe 11Q3, with one of the spots located in the cluster along with the amplified copies. The amplicon to the right yields 4 copies by FISH (probe 11Q4). The ROMA profile for the amplicon represented by probe 11Q6 suggests that it is in a region in which the surrounding non-amplified portion of the arm is deleted. This arrangement is commonly observed in firestorms and is confirmed by the FISH image showing one pair of the loci 11q5 and 11Q6 together, representing the intact arm, and no copy of probe 11Q5 in the amplified cluster of spots for 11Q6.

FIG. 19 shows an illustrative table that may be used to assign a probabilistic measure of one or more outcomes for an individual.

FIG. 23 shows an illustrative table of data obtained from six biopsies.

FIG. 30 shows a map of copy number polymorphisms (CNPs) detected in control samples.

FIG. 31 illustrates an experimental approach that can identify rare variants in the CNPs (e.g., as shown in FIG. 30) and uses the CNP data with linkage data to identify large scale genetic variants that correlate with certain phenotypes or diseases. The illustrative method includes the following steps: i) copy number polymorphisms (CNPs) were obtained from genomic samples from the AGRE collection of biomaterials; ii) the CNPs of the patients were then compared against the database of normal genetic variations (e.g., the map of CNPs obtained from 91 control samples as shown in FIG. 30); iii) rare variants were then identified from that comparison; and iv) large scale CNP variants that correlate with the disease were then identified by integrating the CNP data with the linkage data.

FIG. 32 shows a recurrent CNP at Xp22 detected by ROMA.

FIG. 33 shows recurrent duplication of Yp11.2 detected by ROMA in autism and schizophrenia patients.

FIG. 34 illustrates that the presence of a causal genetic variant detected by ROMA correlates with familial inheritance of a disease.

FIG. 35 shows a deletion of 2q37.3 detected by ROMA in a single patient with autism.

FIG. 37A. Complete Swedish diploid dataset grouped according to three different discriminator settings ($F_d$) of F: $F_d$=0.08 (red); $F_d$=0.09 (blue); $F_d$=0.1(green). FIG. 37B. Swedish diploid dataset separated into node negative (red) and node positive (blue) subsets with $F_d$ set to 0.09.

DETAILED DESCRIPTION OF THE INVENTION

Figure 1:
FIG. 1 shows general features of ROMA CGH profiling. A. Comparison of normal female and male fibroblast cell lines; B. Enlarged version showing X and Y chromosomes; C. WZ39, a representative early stage diploid tumor; D. WZ20, a representative aggressive diploid tumor showing multiply amplified regions.

The present invention is based, in part, on genomic studies of clinically well-defined sets of cancer patients that combine FISH analysis of specific sites with ROMA (Lucito et al., 2003), discussed above. The studies were intended to explore whether high resolution of the genetic events in tumors can form an additional basis for the clinical assessment of breast cancer. The genomic studies were further intended to determine whether increased resolution of the genetic events in tumors can identify significant oncogenes and tumor suppressor loci, known and new, and whether such genetic events can be used to form a more accurate clinical diagnosis and therapeutic assessment of cancers. The genomic studies were also intended to determine whether increased resolution of the genetic events in other diseases, disorders or conditions that may involve genomic rearrangements can identify significant events and/or loci to be used to form a more accurate clinical diagnosis and therapeutic assessment of the respective diseases, disorders or conditions.

In particular embodiments, the present invention is based on data obtained from two studies, one from a collection of over ten thousand frozen breast cancer biopsies maintained at the Karolinska Institute, Stockholm, Sweden; and one from a collection of similar size, based at the Radium Hospital in Oslo, Norway. Samples in each collection are linked to extensive clinical annotations and historical follow-up information for associated tumors and patients. The first study was based on a subset of 140 breast cancer biopsies selected from the Karolinska Institute and is the main set described herein. This subset was designed to have both aneuploid and diploid tumors, with a balance of good and poor outcomes. The individual profiles of these tumors are publicly available. The second study was designed to compare expression profiling with genome profiling in 110 tumor samples from the Norway collection.

The studies demonstrate the similarity of patterns from two different study populations, as well as the commonality of affected loci in aneuploid and diploid cancers. Significantly, a different frequency pattern between diploid tumors with good and poor outcome was found. Moreover, the complexity of events, and the number of events, clearly indicates that genomic profiling is a powerful tool for malignant staging of breast cancer, with the further expectation that it will similarly be a powerful tool for characterizing other cancers, as well as other diseases, disorders and conditions involving chromosomal rearrangements. Thus, results obtained from the studies have important applications in clinical practice, as described in more detail below.

I. "Geometry"—Methods for Predicting Clinical Outcome of a Tumor or Individual Patient Having a Tumor by Phenotyping of Chromosomal Rearrangement Patterns A first aspect of the invention relates to methods in which a global state of genomic rearrangements or the "genomic landscape" (rearrangement position, size, number of events and proximity of rearrangements to each other or the entire genome or a portion thereof), is used as a reliable predictor of clinical outcome. The global state of genomic rearrangements can be mapped using any suitable method. Preferably, methods in which breakpoints (i.e., the location at which relative copy number of adjacent sequences changes) are defined using segmentation genomic profiling methods, such as ROMA, for example, are used to generate genomic landscapes. The genomic landscape, in turn, may be used to derive a number that defines probabilistic measures of clinical outcome for the patient, tissue or cell sample, such as for example a tumor, from which the genomic profile was obtained.

Accordingly, certain embodiments of the invention provide a method for assigning a probabilistic measure of a clinical outcome for an individual patient having a condition, disorder or disease. In certain embodiments, the individual patient has a tumor. The term "tumor" generally refers to abnormal growth of tissue and can be classified as malignant or benign. Malignant tumors generally refer to cancers, which cells can invade and/or destroy neighboring tissues. "Tumor" as used herein encompasses invasive solid cancers, non-invasive solid cancers, e.g., ductal carcinoma in situ, and humoral cancerous cells, such as for example those of the blood. Such embodiments of the present invention are envisioned to be useful for assigning a probabilistic measure of a clinical outcome for an individual patient having diseases other than tumors, such as, for example, degenerative diseases. It will be readily appreciated by the skilled worker that any condition, disorder or disease characterized by genomic rearrangements may be analyzed using the present methods as set forth herein, as explained and exemplified for tumor cells herein. In other embodiments, the individual patient has a disease that involves one or more genomic rearrangements such as copy number variations (e.g., amplification or deletion of one or more genomic regions).

In certain embodiments of the invention, the method may comprise: obtaining a segmented genomic profile, $GP_{(indvl)}$, of DNA extracted from one or more affected cells, e.g., tumor cells, from a first individual patient, the $GP_{(indvl)}$ comprising information on the copy number of a plurality of discrete segments of the genome, or one or more portions of the genome. When relative copy number as a function of genomic position is plotted for genomic segments within said $GP_{(indvl)}$, a particular geometric pattern may be observed. Part or all of the $GP_{(indvl)}$ of the individual patient and part or all of its associated geometric pattern is compared to a database, $GP_{(DB)}$. The $GP_{(DB)}$ database or clinical annotation table comprises multiple entries, each entry comprising: (i) clinical information pertaining to a different patient's or that patient's tumor or disease; and (ii) one or more quantitative measures derived from a genomic profile of the different patient. Thus, the $GP_{(DB)}$ database or clinical annotation table links or associates genomic profile information, which can also include geometric pattern information and which can be at the level of the entire genome or directed to specific regions or loci, to clinical information about the patient or the patient's disease or condition, e.g., tumor. A similarity or correlation between part or all of the individual patient's genomic profile, $GP_{(indvl)}$, or its particular geometric pattern, and that of one or more entries in the $GP_{(DB)}$ database or clinical annotation table is evaluated and used to assign a probabilistic measure of an outcome or a set of outcomes to said individual patient.

In particular embodiments, the method also includes the step of masking the $GP_{(indvl)}$ for known copy number polymorphism (CNP) between genomes or portions of genomes from different individuals to obtain, for the first individual patient, a CNP-masked segmented genomic profile, $GP_{(Mi)}$. The CNP-masked segmented genomic profile, $GP_{(Mi)}$, is then compared to the database or clinical annotation table that comprises one or more quantitative measures derived from a genomic profile of the different patient, wherein optionally, the database or clinical annotation table comprises similarly obtained, CNP-masked segmented genomic profile information for one or more entries.

A "geometric pattern" according to the invention generally includes shape of the profiles, such as for example, flat, simplex, complex, saw toothed, firestorm or any other pattern that can show the number, spacing, level of change of the lesions in the genome or a portion thereof. A "genomic pattern" obtained from a particular patient may be predictive of the clinical outcome for that patient. For example, a high proportion of saw toothed or firestorm patterns is frequently associated with decreased patient survival.

In alternative embodiments of the invention, a genomic profile is used to derive and index value of genomic perturbation. The perturbation index value may be a value associated with rearrangements at the genomic level, or may focus on rearrangements in particular genomic regions or loci, depending on whether characteristics of a full genomic profile or those of localized regions of the genome are used to generate the index value.

In certain embodiments, the method comprises obtaining a segmented genomic profile, $GP_{(indvl)}$, of DNA extracted from one or more affected cells, e.g., tumor cells, from a first individual patient, the $GP_{(indvl)}$ comprising information on the copy number of a plurality of discrete segments of the genome or one or more portions of the genome. A mathematical function is applied to the $GP_{(indvl)}$ (or portion thereof).

In particular embodiments, the mathematical function provides a measure of one or more of: (i) the number of said discrete segments, (ii) the lengths or areas of said discrete segments, and (iii) the distribution of the lengths or areas of at least two adjacent segments and generates a genomic perturbation index value, $PI_{(i)}$ (or firestorm index, FSI), related to the proximity and frequency of breakpoints within one or more genomic regions from the genome of the individual patient. The perturbation index value $PI_{(i)}$ from the individual is compared to a database or clinical annotation table $PI_{(DB)}$, comprising multiple entries, each entry comprising: (i) clinical information pertaining to a different patient and that patient's tumor or disease; and (ii) one or more quantitative measures derived from a genomic profile of the different patient that can generate a genomic perturbation index value. Thus, the database or clinical annotation table $PI_{(DB)}$ links or associates genomic profile information, such as a genomic perturbation index, to clinical information about the patient or the patient's tumor or other diseased tissue or cells. The comparison may be at the level of the entire genome or may be directed to specific regions or loci. A similarity or correlation between part or all of the individual patient's genomic perturbation index value PI(i) and one or more entries of the $PI_{(DB)}$ database, such as a perturbation index value, is evaluated and used to assign a probabilistic measure of an outcome or a set of outcomes to said individual patient.

In particular embodiments, the method further comprises, between steps (a) and (b), performing the step of masking the $GP_{(indvl)}$ for known copy number polymorphism (CNP) between genomes or portions of genomes from different individuals to obtain, for the first individual patient, a CNP-masked segmented genomic profile, $GP_{(Mi)}$. In such embodiments, the mathematical function of step (b) is applied to the masked profile $GP_{(Mi)}$ (or a portion thereof) to obtain the genomic perturbation index value, $PI_{(i)}$.

In particular embodiments, the mathematical function is a monotonic function. The monotonic function can perform in either direction, i.e., can be increasing or decreasing. In particular embodiments, the mathematical function relates to the lengths of at least two adjacent discrete segments. In particular embodiments, the mathematical function is the sum of the reciprocal of the sum of the lengths of at least two adjacent segments. In other particular embodiments, the mathematical function is the sum of the reciprocal of the sum of areas of at least two adjacent segments. In yet other particular embodiments, the mathematical function is the sum of the total number of breakpoints within a genomic region including one or more loci, one or more arms, one or more chromosomes, or any combination thereof, of the tumor or otherwise diseased genome of the individual patient.

In particular embodiments, the mathematical function employs some form of the following relationship:

$$P = \sum_i \frac{1}{S_i + S_{i+1}}$$

where P is the perturbation index value, "i" is a particular segment, and $S_i$ is the length of segment i.

In certain embodiments, a segmented genomic profile, $GP_{(indvl)}$, is at a resolution of 100, 80, 60, 50, 40, 30, 20, 10, 5 or 1 kilobase(s) or less. In particular embodiments, a segmented genomic profile, $GP_{(indvl)}$, is at a resolution of 35 kilobases or less. In other embodiments, $GP_{(indvl)}$, is at a resolution of 800, 600, 400, 200, 100, 50 or fewer bases.

To practice a method of the invention, the relative copy number of genomic segments is measured above a noise threshold determined by a method comprising the step of:

(a) setting the relative copy number of a genomic segment to a measured value of that genomic segment when the measured value differs from 1 by more than a predetermined fraction of the standard deviation of the relative copy number found in a set of cancer-free genomes or to 1 when the measured value does not differ from 1 by more than a predetermined fraction of the standard deviation of the relative copy number found in the set of disease-free (e.g., cancer-free) genomes.

CNP Masking

Certain embodiments of the present invention relate to a method for masking the contribution of copy number polymorphism among individuals in a segmented genomic profile representing chromosome rearrangements present in DNA derived by measuring relative copy number of a plurality of discrete segments of the genome or a portion of the genome.

In certain embodiments, the CNP masking of the segmented genomic profile is performed by a method comprising the steps of:

(a) generating a mask, the generating comprising:
(i) providing a set of non-cancer genomes; and
(ii) determining at least one contiguous set of probes in the set of non-cancer genomes satisfying at least two predetermined conditions; and (b) applying the mask to provide a mask of the segmented genomic profile, the applying step comprising:
(i) determining at least one contiguous group of segments in a segmented profile of an individual that is a subset within one of the at least one contiguous set of probes; and
(ii) changing the value of a segment ratio of at least one segment within the at least one contiguous group of segments.

The two predetermined conditions of step (a)(ii) above may comprise: (1) requiring the relative copy number to be greater (for amplifications) and less (for deletions) than 1 in no less than x percentage of all probes within a particular contiguous set of probes; and (2) requiring the relative copy number to be greater (for amplifications) and less (for deletions) than 1 in no less than y percentage of at least one probe within a particular contiguous set of probes.

In certain embodiments, the changing step (b)(ii) above may comprise the steps of:
selecting a probe from the at least one contiguous group of segments in the segmented profile of the individual;
locating a first segment bordering the contiguous group of segments on the left;
extending the first segment to the right through the selected probe;
locating a second segment bordering the contiguous group of segments on the right; and
extending that segment to the left until the selected probe.

In certain embodiments, the changing step (b)(ii) above may comprise the steps of:
selecting a probe from the at least one contiguous group of segments in the segmented profile of the individual, wherein when the contiguous group of segments of the selected probe spans a chromosome, the relative copy number is set to 1 throughout that chromosome.

Methods of Genomic Profiling/Measuring Copy Number

The present invention can employ any suitable method for genomic profiling that generates information relating to copy number as a function of genomic position. Preferably, the method is one that involves segmentation of part or all of the genome. Representative methods that can be used according to the invention include, but are not limited to: ROMA; optical mapping methods; cytogenetic analyses; multiplex PCR; random PCR; mass spectrometry; NMR; and any combination thereof.

Genomic profiles can be obtained by mapping, which can include genetic mapping and/or physical mapping. Genetic mapping commonly involves DNA-based markers, which may include one or more of the following: 1) RFLPs, or restriction fragment length polymorphisms, defined by the presence or absence of a restriction site; 2) VNTRs, or variable number of tandem repeat polymorphisms, defined by the presence of a nucleotide sequence that is repeated several times; 3) MSPs, or microsatellite polymorphisms, defined by a variable number of repetitions of a very small number of base pairs within a sequence; and 4) SNPs, or single nucleotide polymorphisms, which are individual point mutations, or substitutions of a single nucleotide, that do not change the overall length of the DNA sequence in that region. Physical maps of a genome can be divided into three general types: chromosomal or cytogenetic maps based on the distinctive banding patterns observed by light microscopy of stained chromosomes, radiation hybrid (RH) maps which are similar to linkage maps and capable of estimating distance between genetic and physical markers, and sequence maps generated by mapping STSs or sequence tagged sites (including expressed sequence tags or ESTs, simple sequence length polymorphisms or SSLPs, and random genomic sequences).

Optical mapping is an approach for the rapid, automated, non-electrophoretic construction of ordered restriction maps of DNA from ensembles of single molecules. It was initially developed as a light microscope-based technique for rapidly constructing ordered physical maps of chromosomes. Schwartz et al., *Science* 1993 Oct. 1; 262(5130):110-4. For a review, see Aston et al., *Methods Enzymol.* 1999; 303:55-73.

A combination of optical mapping and long-range polymerase chain reaction (PCR) has been reported (Skiadas et al., *Mamm. Genome.* 1999 October; 10(10):1005-1009), a process we term optical PCR, which enables automated construction of ordered restriction maps of long-range PCR products spanning human genomic loci. In that report, three long PCR products were amplified, each averaging 14.6 kb in length, which span the 37-kb human tissue plasminogen activator (TPA) gene. The PCR products were surface mounted in gridded arrays, which were then mapped in parallel with either ScaI, XmnI, HpaI, ClaI, or BglII. The technique generated overlapping high-resolution maps, which agreed closely with maps predicted from sequence data. Thus, this approach can be used for constructing physical maps of genomic loci where very little prior sequence information exists. Automated optical mapping also made it possible to map a set of sixteen BAC clones derived from the DAZ locus of the human Y chromosome long arm, a locus in which the entire DAZ gene as well as subsections within the gene copies have been duplicated. Giacalone et al., *Genome Res.* 2000 September; 10(9):1421-9.

A recent report on chromosomal breakpoint mapping involved the applications of high-resolution GTG banding and fluorescence in situ hybridization (FISH) with several probes, including bacterial artificial chromosomes (BACs). Kulikowski et al., *Am. J. Med. Genet. A.* 2005 Dec. 6, Epub.

Others have reported losses and gains of loci at 112 unique human genome sites using the multiplex ligation-dependent probe amplification assay (MLPA) (Worsham et al., *Breast Cancer Res Treat.* 2005 Nov. 30; 1-10, entitled "High-resolution mapping of molecular events associated with immortalization, transformation, and progression to breast cancer in the MCF10 model.") In addition, Huang et al. (*Clin. Genet.* 2005 December; 68(6):513-9) have described molecular cytogenetic characterization using high-resolution CGH and multiplex FISH analyses with various alpha-satellite DNA probes, an all-human-centromere probe (AHC), whole chromosome painting probes, and a sub-telomere probe.

MALDI-TOF mass spectrometry has also proved to be a powerful tool in SNP genotyping and can be applied to genomic profiling. See, e.g., Lechner et al., 2001, *Curr. Op. Chem. Biol.* 6:31-38. See also Hamdan et al., Mass Spec. Rev. 2002, 21:287-302; Aebersold et al., Nature 2003, 422:198-207.

In certain embodiments of the present invention, the whole genome is profiled globally. In alternative embodiments, one or more portions (e.g., regions or loci) of the genome known to be susceptible to chromosomal rearrangements are profiled.

In certain embodiments, a database or clinical annotation table is used to compare genomic profile information from a patient of interest to that of other patients for which clinical information has been gathered on the disease, the tumor or other affected tissue or cells, and the patient. One or more quantitative measures derived from the patient's genomic profile is compared to one or more of those measures in the database, and similarities are evaluated and used to assign a probabilistic measure of an outcome or a set of outcomes relating to the disease, e.g., the tumor, and/or the patient. Thus, the database or clinical annotation table may comprise clinical information that includes one or more traits including (in the case of tumors), but not limited to: tumor type, tumor stage, tumor characteristics; metastatic potential; response of tumor to a particular therapeutic agent, therapeutic composition, treatment method, or to an environmental perturbation; familial medical history or additional genetic information pertaining to the individual patient; and time after diagnosis of patient survival. Response of tumor generally refers to tumor behavior as reflected by tumor growth, size, and other measures for tumor progression, or any combination of the measures. An environmental perturbation can include previous medical treatments (including chemotherapy or radiation therapy or both) or exposure to biologically active compounds capable of eliciting a biological response in an individual. Such biologically active can include those intended for human use such as food, drug, dietary supplements, or cosmetics, or those unintended for human use such as hazardous materials, the exposure to which may be through unwanted contamination of an individual's environment.

It will be recognized that response of other diseased tissues or cells of a patient characterized by genomic rearrangements may similarly be measured, the data annotated and stored in databases for comparisons that enable similarities to be evaluated and used to assign a probabilistic measure of an outcome or a set of outcomes relating to the disease and/or the patient in other, non-cancer related disorders, conditions and diseases.

Assigning a Probabilistic Measure to Clinical Outcome

Figure 17:
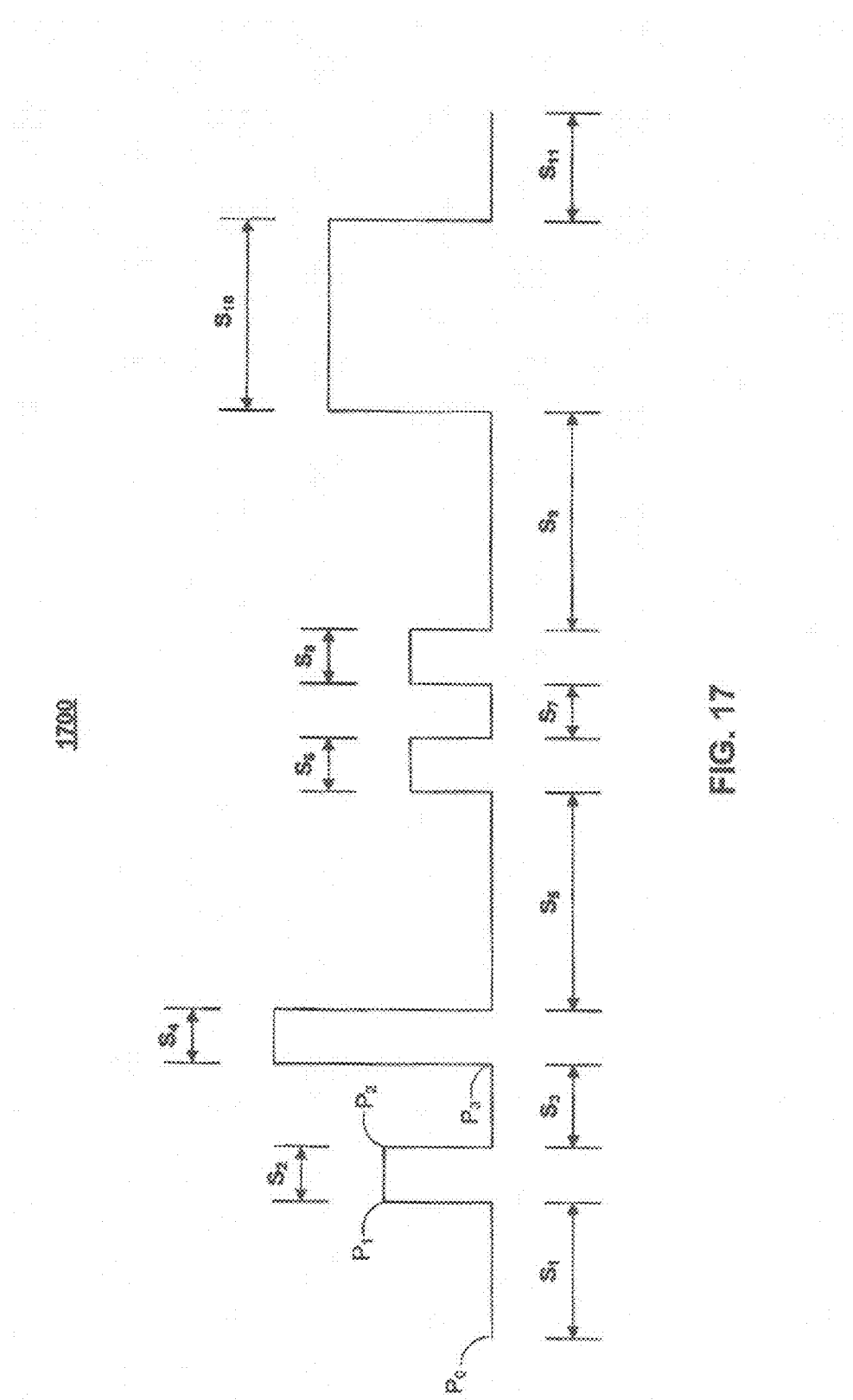
FIG. 17 shows an illustrative segmented genomic profile.

The following discusses an example of one way a segmented genomic profile can be analyzed to assign a probabilistic measure of one or more clinical outcomes for an individual patient. In particular, the following example is discussed in connection with FIGS. 17-21. Referring now to FIG. 17, an illustrative segmented genomic profile (SGP) 1700 is provided, having segments $S_{1-11}$. SGP 1700 may represent the entire genomic profile of an individual or a portion thereof (e.g., a specific location or locus of the individual's genomic profile). The vertical coordinates of SGP 1700 may represent the relative copy number of the segment, or a monotonously increasing or decreasing function thereof. For purposes of clarity, SGP 1700 shows a profile having only amplifications (which fall above the baseline), though it is understood that a segmented profile may include both amplifications and deletions (which would fall below the baseline) or have only deletions.

Generally, the process analyzes SGP 1700 to locate the breaks, or "breakpoints" which indicate where a segment begins or ends. A break occurs when the copy number in a subsequent and adjacent location changes relative to the copy number in the immediately preceding location. The copy number may change, for example, because of a local amplification or a deletion. In FIG. 17, $P_0$ and $P_1$ refer to a starting and ending location, respectively, of segment $S_1$. At $P_1$, the copy number changes relative to the copy number of the segment starting at $P_0$, thus indicating a breakpoint and the beginning of segment $S_2$. $P_2$ indicates the end of amplified segment $S_2$ and the beginning of segment $S_3$. $P_3$ indicates the end of segment $S_3$ and the beginning of segment $S_4$, and so on. Points may refer to probes, probe numbers, or genomic coordinates of these probes. Thus, for example, if a segment ends at a probe, the next segment begins at the following probe.

As SGP 1700 is processed, the length of each segment is stored in a storage device (e.g., memory, hard-drive, etc.). For example, for each segment Si, where "i" represents a particular segment, the length corresponding to the particular segment is stored. The length is a numerical value and may be based on, or derived from, for example, the number of base pairs included in the segment. Segments may include regions in the genomic profile where amplifications or deletions occur (e.g., shown by segments $S_2$, $S_4$, $S_6$, $S_8$, and $S_{10}$) and regions between two amplifications, two deletions, or an amplification and a deletion (e.g., shown by segments $S_1$, $S_3$, $S_5$, $S_7$, $S_9$, and $S_{11}$). By storing segments in this manner, the process can determine the number of segments or breaks that occur in SGP 1700. In addition, the process also determines the length between breaks (e.g., the length between $P_1$ and $P_2$, segment $S_2$) and the length between adjacent breaks (e.g., the length between $P_2$ and $P_3$, segment $S_3$). As discussed below, other information relating to segments and breakpoints, such as area under peaks defined by the length and height of individual segments, either above or below the baseline, may also be calculated and stored.

As a result of the processing, the stored data (e.g., the lengths of segments and the number of segments) may be further processed to obtain a Perturbation or Firestorm index, which index may be used to provide information pertaining to a probabilistic measure of one or more clinical outcomes of the individual. The Perturbation index may measure the degree to which particular regions of the genome have undergone local rearrangements such as amplifications and/or deletions.

The perturbation index may be found using one of many different equations that take into account one or more of the following with respect to a segmented genome (or a genomic region of interest): (a) the number of segments; (b) the length (or area) of each segment; (c) the length (or area) of one or more sets of adjacent segments; and (d) vertical coordinates of segments. Equations useful for calculating a perturbation index based on one or more of the above factors will be readily apparent to one of skill in the art. In certain embodiments of the invention, the equation is a monotonic function. The equation can be a monotonically increasing function, or a monotonically decreasing function. In certain embodiments of the invention, the equation is a monotonic function which may operate in either direction. Particular examples of such equations are equations 1-6 shown below.

Equation 1 is represented by the following equation:

$$P = \sum_i \frac{1}{S_i + S_{i+1}} \tag{1}$$

where "i" is a particular segment and $S_i$ is the length of segment "i". Equation 1, when expanded using the segments from SGP 1700, is shown below.

$$P = \sum_i \frac{1}{S_1 + S_2} + \frac{1}{S_2 + S_3} + \frac{1}{S_3 + S_4} + \ldots + \frac{1}{S_{10} + S_{11}}$$

As indicated by Equation 1, the length of all of the segments (i.e., the length of the breaks and the lengths between breaks) is used to yield a perturbation index.

Equation 2 shows how a perturbation index may be obtained using the length of the breaks (e.g., amplifications and/or deletions):

$$P = \sum_i \frac{1}{\text{Length-of-Breaks}_i} \tag{2}$$

where "i" is a segment corresponding to a particular break and Length-of-Break; is the length of an amplification or deletion at segment "i". Equation 2, when expanded using the segments from SGP 1700, is shown below.

$$P = \sum_i \frac{1}{S_2} + \frac{1}{S_4} + \frac{1}{S_6} + \frac{1}{S_8} + \frac{1}{S_{10}}$$

Equation 3 shows how a perturbation index may be obtained using the lengths between breaks.

$$P = \sum_i \frac{1}{\text{Length-Between-Breaks}_i} \tag{3}$$

where "i" is a segment corresponding to a segment between breaks (e.g., a region between two amplifications, two deletions, or an amplification and a deletion) and Length-Between-Breaks; is the length segment "i". Equation 3, when expanded using the segments from SGP 1700, is shown below.

$$P = \sum_i \frac{1}{S_1} + \frac{1}{S_3} + \frac{1}{S_5} + \frac{1}{S_7} + \frac{1}{S_9} + \frac{1}{S_{11}}$$

Equation 4 shows how a perturbation index may be obtained based on the reciprocal number of segments in the segmented genomic profile:

$$P = \frac{1}{\text{number of segments}} \tag{4}$$

When using the segments in SGP 1700, the number of segments is eleven. Alternatively, a perturbation index may be equal to the number of segments, rather than the reciprocal.

Equation 5 shows how a perturbation index may be based on the vertical coordinates of segmented genomic profile:

$$P = \sum_i \frac{|(\text{vertical coordinate}_{i+1}) - (\text{vertical coordinate}_i)|}{(S_{i+1} + S_i)} \tag{5}$$

where "i" is a particular segment, $S_i$ is the length of segment "i", and vertical_coordinate$_i$ represents the relative copy number of the segment, or a monotonously increasing or decreasing function thereof for segment "i".

Figure 18:
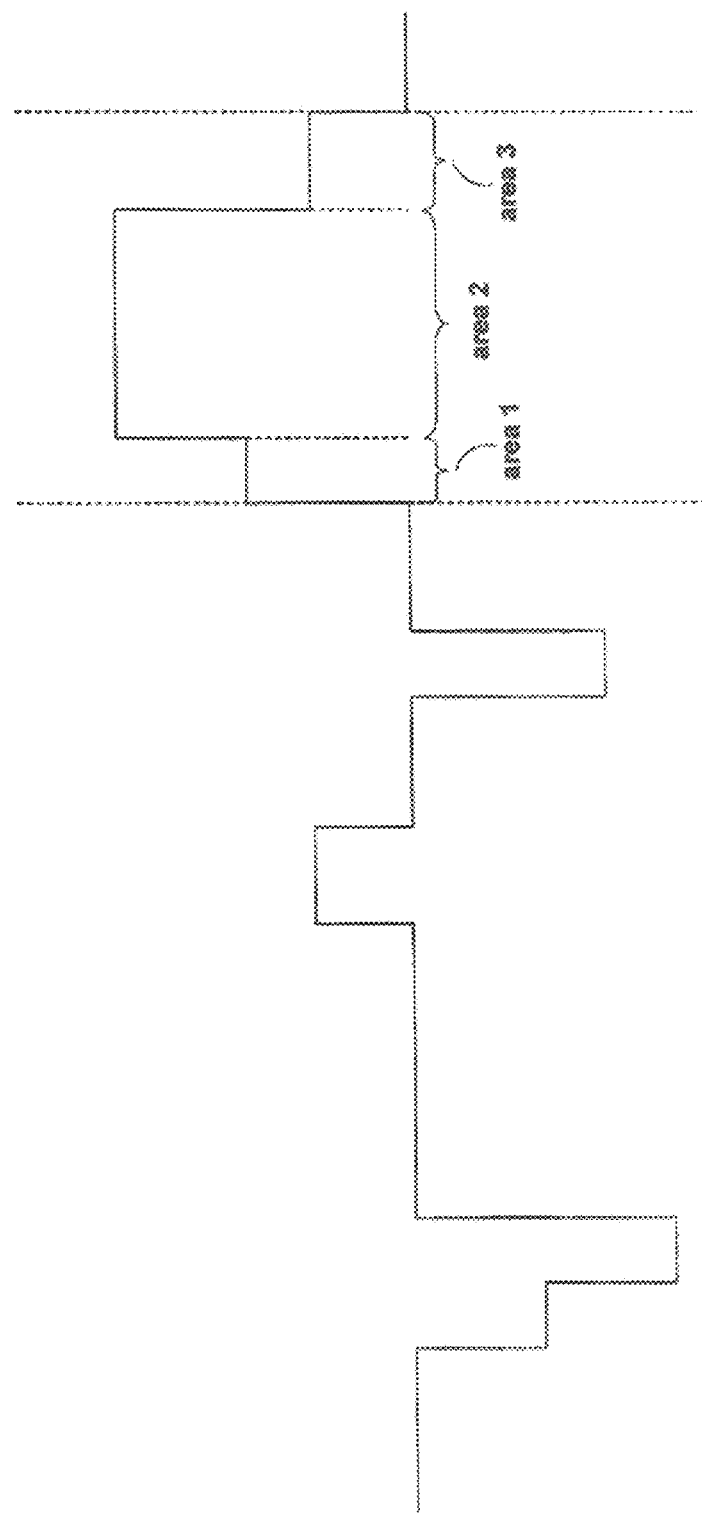
FIG. 18 shows an alternative illustrative segmented genomic profile.

Equation 6 shows how a perturbation index may be based on the sum of the areas of at least two adjacent regions. Equation 6 may be advantageous in generating perturbation indexes for situations where the segmented genomic profile has two or more adjacent amplifications or two or more adjacent deletions, especially in cases where there is no region existing between two amplifications or two deletions, as shown in FIG. 18. Equation 6 is represented by the following equation:

$$P = \sum_i \frac{1}{\text{Area}_i + \text{Area}_{i+1}} \quad (6)$$

where "i" is a particular segment and Area$_i$ is the area corresponding to that particular segment. In applying Equation 6 to the region contained with the dashed lines, Equation 6 may be expanded as follows:

$$P = \sum_i \frac{1}{\text{Area}_1 + \text{Area}_2} + \frac{1}{\text{Area}_2 + \text{Area}_3}$$

It is understood that Equations 1-6 are merely examples of a few ways perturbation indexes may be calculated based on a segmented genomic profile and the embodiments of the present invention are not intended to be limited solely to these or other of the examples described herein.

When the perturbation index is obtained it may be compared to a perturbation database or annotation table to assign a probabilistic measure of one or more clinical outcomes of the individual. The perturbation database may contain data that indicates, for example, whether a particular individual will survive or die, whether a particular treatment will be effective, or for determining any other suitable outcome. For example, the perturbation database may contain perturbation indexes of genomic profiles or portions thereof of individuals for which the survival status (e.g., individual survived or died) is known. Thus, when the genomic profiles of individuals whose survival status is known are processed to obtain perturbation indexes using, for example, the equations discussed above, those perturbation indexes may provide a baseline for determining clinical outcome of an individual whose survival status is unknown. For example, assume that the perturbation value of an individual falls within a range of perturbation values where a predetermined percentage of individuals did not survive. As such, it may be the case that this individual has the same relative predetermined percentage chance of not surviving.

It is understood that there are many known techniques for comparing a number such as the perturbation index to numbers stored in a database. It is further understood that many or all of these known techniques may be used with various embodiments of the present invention. FIG. 19 shows a table with perturbation index values illustrating how perturbation values may be compared to those in a database and may be used to assign a probabilistic measure of one or more outcomes for an individual. The data in the table may be the result of a compilation of data obtained from a set of individuals for which the clinical outcome is known (e.g., lived or died after seven years). The table shows several perturbation index values (e.g., firestorm index values) arranged in a logical order (e.g., smallest to largest). The table shows, in the second column, a p-value indicating the significance of association between an event of a genomic profile having at least the perturbation index value and an event of survival. For example, in row 1, the (p-value) is (0.00034) for perturbation index value of 0.008. In column three, a value indicative of the strength of association between the event of genomic profile having at least the perturbation index value and the event of survival is shown. In column four, a relative risk of non-survival for tumors with perturbation index higher than the one indicated in column one is shown. The relative risk here is defined as a ratio between the probability of non-survival in the patient group with perturbation indices above the given value and the probability of non-survival in all the tumors in the database. Other definitions may be used.

When a perturbation index is obtained for an individual, that index may be compared to the data in the table to assign a probabilistic measure of one or more outcomes for that individual. For example, assume that the individual has a perturbation index of 0.051. Because this value falls between the values of 0.048 and 0.056 in the table, it can be inferred that the risk of non-survival for this individual is between 2.07 and 2.09 times higher than average.

Figure 19A:
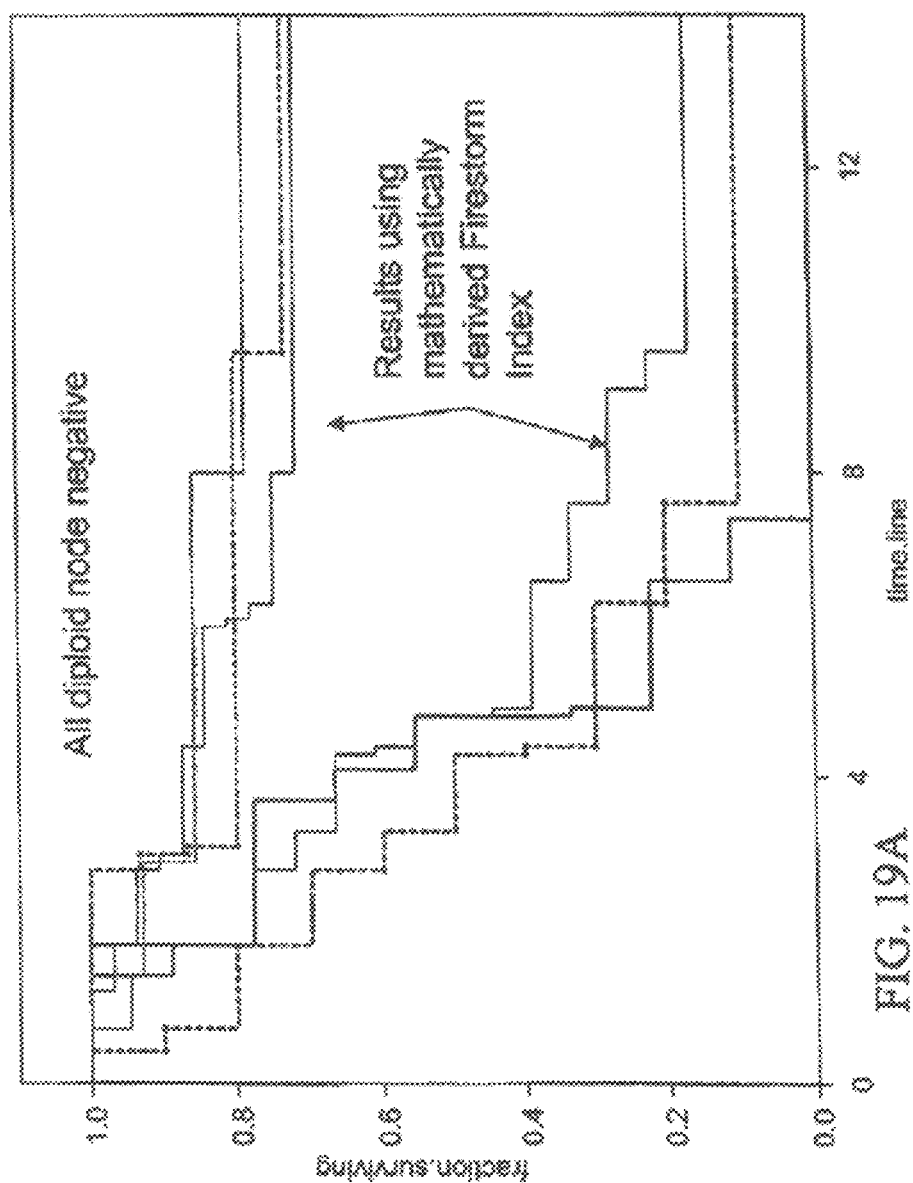
FIG. 19A shows an illustrative Kaplan-Meier plot showing results mathematically derived from a perturbation index.

FIG. 19A serves to compare a number of Kaplan-Meier plots. Each plot describes survival as a function of time in a subgroup of patients. The subgroups, generally speaking, were selected from the entire experimental group in two different ways: (a) by visually classifying their genomic profiles as belonging (or not) to the firestorm category and (b) by the criterion of their firestorm indices being above (or below) a certain value. FIG. 19A serves to illustrate the idea that survival in a subgroup that visually appears to have firestorms is close to survival in a subgroup where the firestorm index is found above a certain value. The horizontal coordinate is time since diagnosis, and the vertical one is survival. The conclusion is that the firestorm index can be used reliably to detect genomic profiles that belong to a firestorm category.

Figure 20:
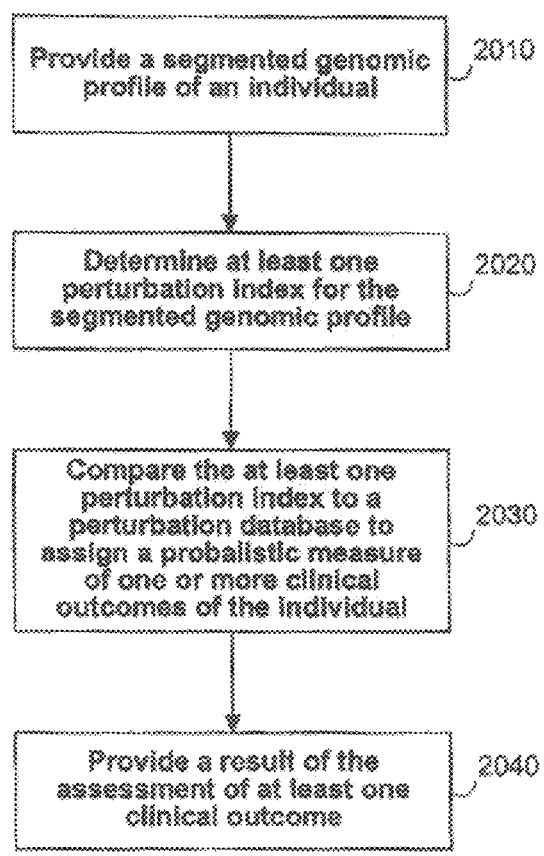
FIG. 20 shows a flowchart illustrating steps that may be taken to assign a probabilistic measure of one or more clinical outcomes for an individual patient.

FIG. 20 shows a flowchart illustrating steps that may be taken to assign a probabilistic measure of one or more clinical outcomes for an individual patient in accordance with an embodiment of the present invention. Beginning at step 2010, a segmented genomic profile of an individual may be provided. Such a profile may be provided, for example, after a biopsy of the individual (such as a tissue or tumor biopsy or blood sample, where applicable) is taken and processed. At step 2020, at least one perturbation index for the segmented genomic profile is determined. For example, one of equations 1-6 may be used to determine a perturbation index. At step 2030, the one or more perturbation indexes may be compared to a perturbation database to assign a probabilistic measure of one or more clinical outcomes of the individual. At step 2040, a result of the assessment of at least one clinical outcome is provided. For example, if the clinical outcome is an assessment of survival, the result may be a percentage of the individual's chance of survival for a particular time after harvesting of the tissue or tumor biopsy sample.

Figure 21:
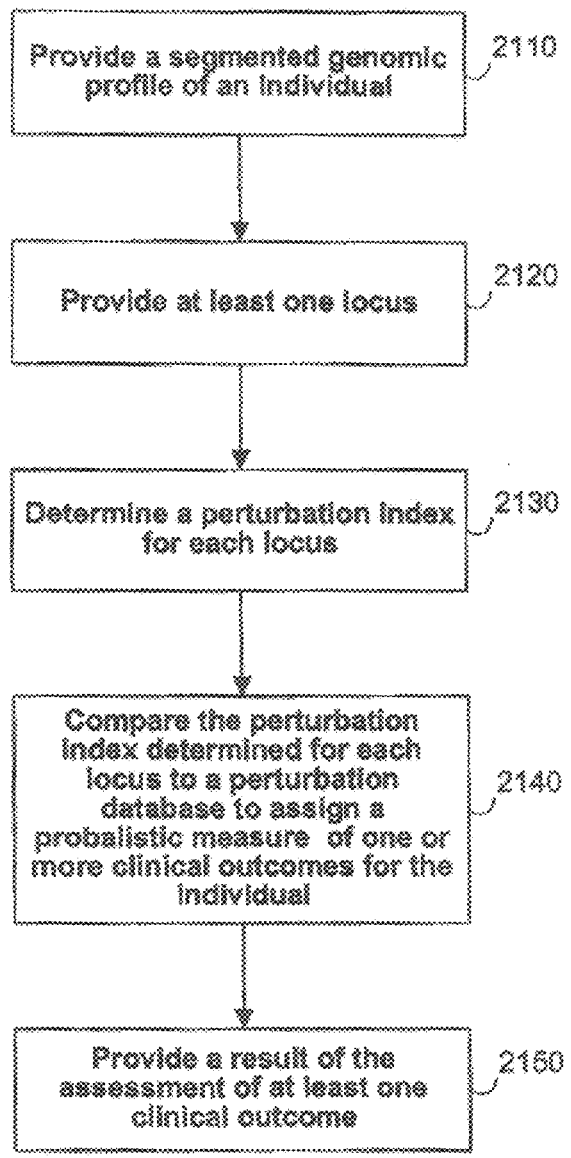
FIG. 21 shows an alternative flowchart illustrating steps that may be taken to assign a probabilistic measure of one or more clinical outcomes for an individual patient.

FIG. 21 shows an alternative flowchart illustrating steps that may be taken to assign a probabilistic measure of one or more outcomes for an individual patient in accordance with an embodiment of the present invention. FIG. 21 is similar in many respects to FIG. 20, but illustrates a method for determining a perturbation index for several predetermined locations on a genome of an individual. A predetermined location on a genome as illustrated may correspond to a particular locus. This method provides an accurate assessment of probabilistic outcome by limiting the analysis of the genome to certain regions or loci. Beginning at step 2110, a segmented genomic profile of an individual is provided. At least one locus is provided at step 2120. The locus may define coordinates of a genome known to harbor "trouble spots" or may be obtained using, for example, a loci detection method described below in connection with FIG. 22. The method as illustrated in FIG. 21 may provide a comprehensive analysis of the entire genome of an individual by analyzing a plurality of predetermined regions or loci throughout the genome.

At step 2130, a perturbation index is determined for each locus. That is, at each locus (e.g., the coordinates represented by the locus), a perturbation index is obtained. By determining the perturbation index at each locus, the process may advantageously enhance the accuracy of the assessment of the probable outcome for various individuals, even for individuals having substantially different genetic backgrounds (e.g., race, ethnic origin, etc.) than the individuals whose genomic profiles are used to construct a perturbation database.

At step 2140, the perturbation index determined for each locus may be compared to a perturbation database to assign a probabilistic measure of one or more clinical outcomes for the individual. At step 2150, the result of the assessment of at least one clinical outcome is provided.

As described and exemplified herein, by applying ROMA for measuring copy number of segments of genomic DNA extracted from tumors, and comparing the genomic profiles or patterns of chromosomal rearrangements of the tumor DNA with clinical outcome data for each tumor, statistically significant correlations were obtained between sets of chromosomal rearrangements or genomic profiles and clinical outcome for the tumor or patient. In the tumor samples studied, by considering all of the events taken together at the level of the genomic landscape, the genomic profiles can account for more than 50% correlation between survival and non-survival within a ten year period. It should be understood that this is merely an example illustrating the power of this approach, and that genomic profiles (global, regional or local) will be expected to have different % correlative values depending on the patient and/or tumor type, the type of genomic profiling performed, and the one or more clinical outcomes being monitored.

The ability to make meaningful correlations between sets of chromosomal rearrangements or genomic profiles and clinical information of diseased tissues (such as tumors) and patients has important clinical applications including, but not limited to, diagnosing a patient before the onset of disease symptoms or at the very early stage of a tumor, for example, thereby improving prognosis of that patient; accurately staging a tumor, thereby designing appropriate therapeutic regimen; and predicting or assessing a patient's likely response to a given treatment based on the patient's genomic profile. Accordingly, the methods and compositions of the invention provide important tools for disease diagnosis and treatment, and for achieving individualized medicine that accounts for interpersonal variation in responses to different treatments.

II. "The Discriminator"—Methods for Predicting Clinical Outcome of a Tumor or Individual Patient Having a Tumor by Profiling Specific Loci Another aspect of the invention relates to the discovery that individual genomic loci, alone and/or in combination, undergo rearrangements (in terms of number, size, and/or frequency) across patient subgroups and/or tumor subtype populations. These loci, individually and/or in combination, are referred to herein as "discriminators," and are diagnostically useful and highly predictive of disease, e.g., tumor, and/or patient clinical outcome. Accordingly, the invention provides a method for identifying discriminators and employing discriminators in determining a probabilistic measure of one or more clinical outcomes with relation to a patient and disease progression, such as for cancer. The invention also provides methods for obtaining and analyzing genomic profiles of particular discriminator loci, where such discriminators have been identified, thereby eliminating the need for global profiling of the entire genome but retaining the highly predictive value of the partial genomic profiles. Under certain circumstances, for example, where familial disease susceptibilities are known, such as particular tumor or cancer susceptibilities, partial genomic profiling at particular discriminator loci will be more efficient and cost-effective. Likewise, for example, particular tumor subtypes may be more quickly and efficiently identified and patients diagnosed using partial genomic profiling at particular discriminator loci, where applicable to the subtype, rather than having to create entire genomic profiles of those tumor subtypes. It is envisioned that discriminators will be identified and similarly useful in diagnosing and choosing treatment methods for a wide variety of diseases other than cancer, i.e., those in which chromosomal rearrangements at one or a combination of particular genomic loci are associated with the disease in a statistically relevant manner.

Figure 4:
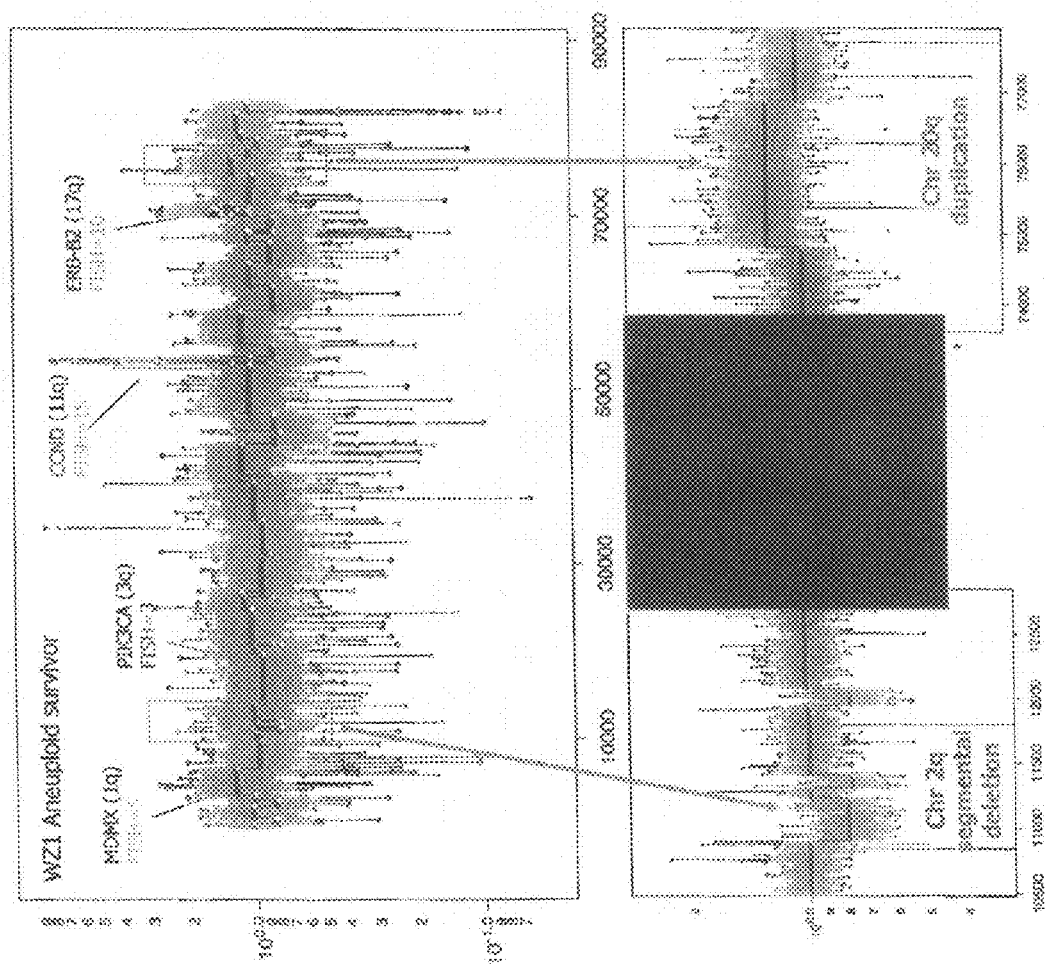
FIG. 4 compares copy number as assayed by ROMA and FISH. Tumor WZ1 is aneuploid with an average genome copy number of 3n by FACS analysis. The results using FISH probes for various loci are indicated in the top graph. The bottom panels show enlarged views of small deletions and duplications picked to demonstrate the correspondence between FISH and ROMA. The photograph shows a two color FISH experiment using probes for the deletion and duplication, respectively, depicting loss and gain, respectively, of the two probes relative to the normal genome copy number. PIK3CA on chromosome 3q yields a value of 1.0 by ROMA and 3 copies by FISH. MDMX on 1q yields a copy number of 5 by FISH, consistent with a near doubling of the copy number of the entire 1q arm as shown by ROMA.
Figure 15:
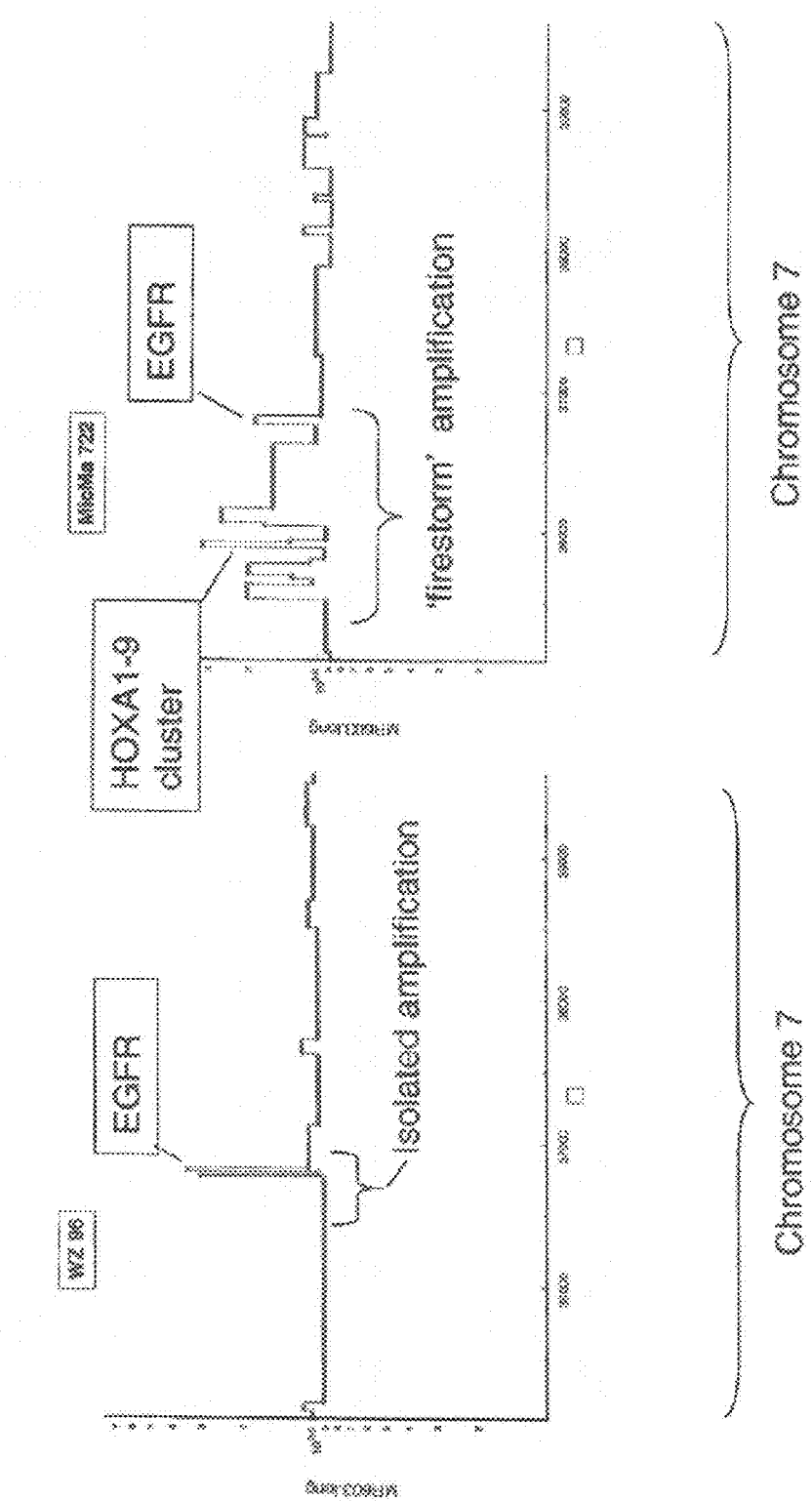
FIG. 15 shows amplification of the EGFR locus as detected by ROMA. The EGFR gene amplification, either singly or as part of a multiple clustered chromosomal rearrangement ("firestorm"), can be identified simultaneously with the HER2, TOP2A and BRCA genes by ROMA. Probes used in the studies for these loci are listed in Table 8, following the Exemplification.

In certain embodiments, a method for identifying a discriminator employs the steps described above for methods for obtaining and analyzing a genomic profile, and further comprises the step of identifying one or more specific genomic segments whose relative copy number correlates with disease, tumor or patient clinical outcome. As exemplified herein, in certain embodiments of the invention, the discriminators include, but are not limited to the following loci: Her1/EGFR (e.g., as shown in FIG. 15), Her2 (e.g., as shown in FIG. 4), and INK (INK4, at chromosome 9p21.97, included in GenBank Accession No. NT_008413).

Certain embodiments of the invention provide a method for identifying one or more specific genomic segments that, when considered alone or in combination, exhibit a degree of association with probable clinical outcome of greater than about 1%, 2%, 4%, 6%, 10%, 20%, 30%, 40%, 50%, 60% or higher.

Figure 22A:
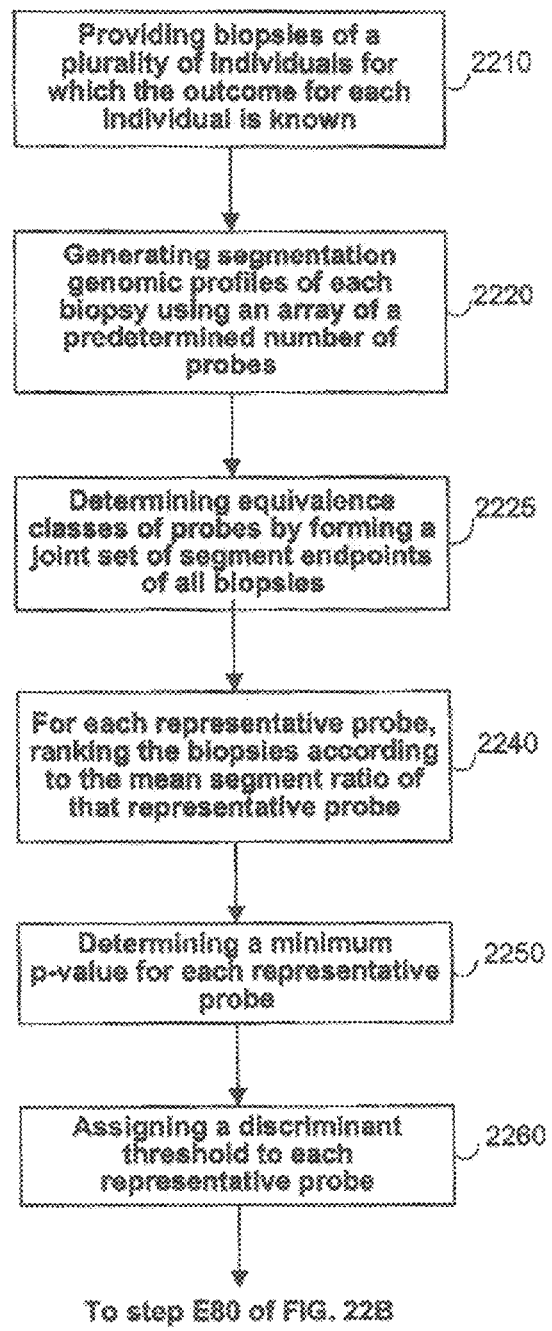
FIGS. 22 (A and B) shows a flowchart illustrating steps that may be taken to locate loci that correlate with survival.
Figure 22B:
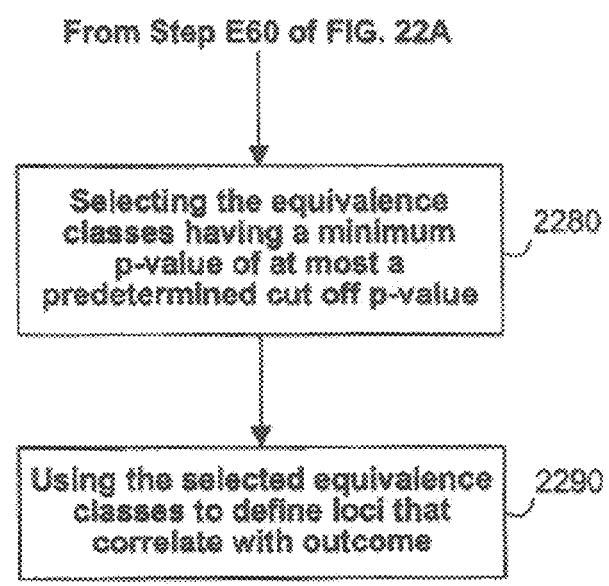
Figure 24:
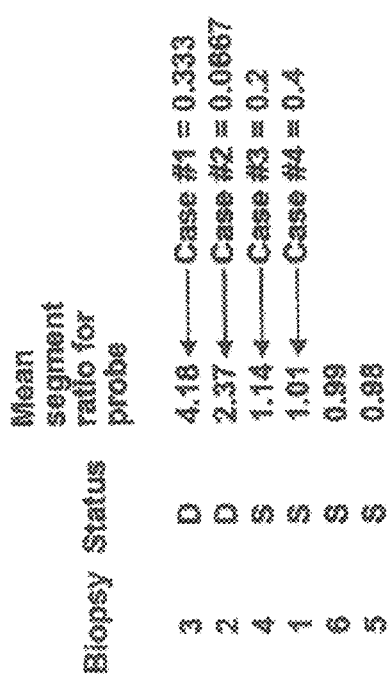
FIG. 24 shows an illustrative table in which the data in FIG. 23 is ranked by mean segment ratio.
Figure 25:
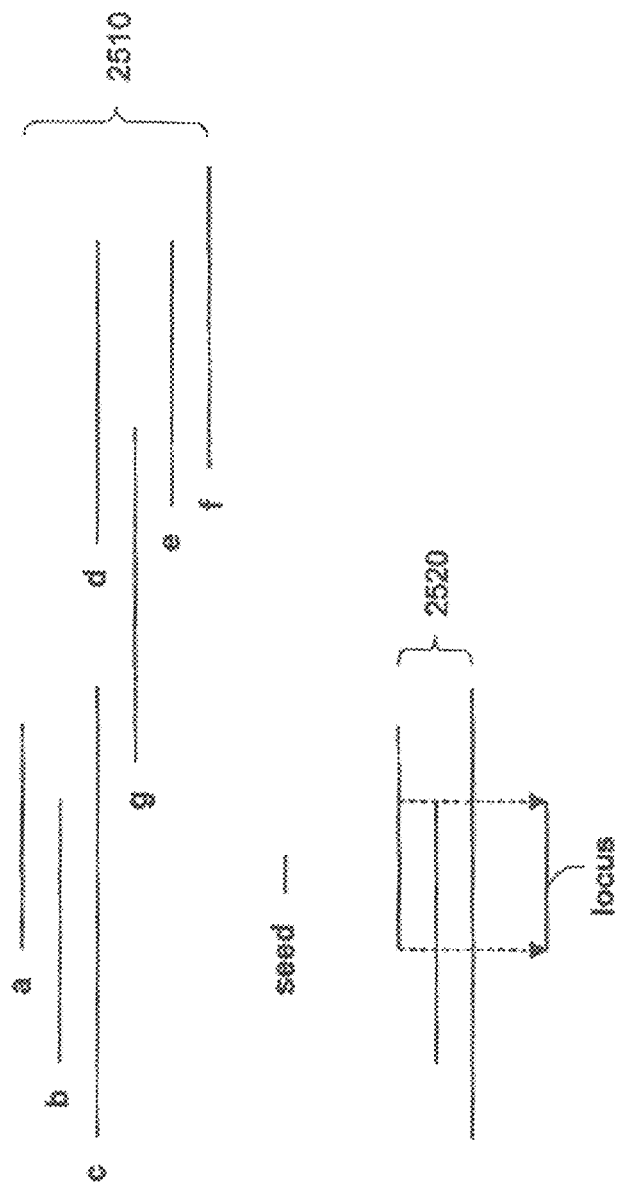
FIG. 25 graphically shows how the principle of minimum intersect may be used to locate loci that correlate with survival.

FIG. 22 shows a flowchart of illustrative steps that may be taken to locate loci that correlate with survival in accordance with an embodiment of the present invention. The loci discovered may be used as in the flowchart shown in FIG. 22. To facilitate an ease of understanding the steps shown in FIG. 22, reference will be made to FIGS. 23-25. Note that the contents of FIGS. 23-25 are by no means meant to represent actual data that have been obtained using the loci location method, but rather, represent illustrative data presented for the purpose of aiding the reader in understanding the steps shown in FIG. 22. Further note that, although FIG. 22 occurs on two separate sheets, labeled FIGS. 22A and 22B, respectively, any reference to FIG. 22 refers collectively to either FIG. 22A or 22B.

Beginning at step 2210, biopsies of several individuals are provided. For example, the biopsies may be samplings of tumor cells (e.g., breast cancer cells) from different patients whose survival status is known. That is, for each patient, it is known whether the patient died or survived at the expiration of a predetermined period of time (e.g., seven years) after the samples were taken from the individuals.

At step 2220, a segmentation genomic profile of each biopsy may be generated using an array of a predetermined number of probes. For example, an array of 85,000 probes may be used to obtain data that may be used to generate a segmentation genomic profile of each biopsy. The data may be obtained using one of many different approaches, including, for example, ROMA an optical mapping method, cytogenetic analysis, PCR, mass spectral analysis, NMR, random PCR, any technique that can detect amplifications or deletions, or any combination thereof to obtain data for generating a segmentation profile. Each of these approaches are understood by those skilled in the art and need not be discussed in more detail to facilitate an understanding of the embodiments of the invention.

When the data are obtained, they may be processed by a segmentation algorithm that converts the raw data (e.g., obtained using ROMA) into data representing a segmented genomic profile. The segmentation algorithm may apply a statistical procedure to raw data (e.g., ROMA data) that yields a consecutive set of segments that are considered amplified or deleted as a group in the genome or portion thereof of the individual, relative to a normal standard genome. In one embodiment, the segmentation algorithm may use the Kolmogorov-Smirnov test and minimum variance (e.g., a process to reduce noise) to process the raw data.

A mean segment ratio is determined for each probe of the array for each biopsy. The mean segment ratio of a particular probe may be based on the mean ratio of the segment (obtained using the segmentation algorithm or algorithms) containing that particular probe. The mean ratio of a segment is the mean ratio of the probes that are grouped by one or more (segmentation) algorithms into a single segment. The consecutive set of segments may be represented by a series of endpoints, each endpoint marking either a beginning or ending of a segment. Thus, two adjacent endpoints may define a segment. After all biopsies are processed, the endpoints for all biopsies may be stored as a set of endpoints in a database, referred to herein as an endpoint set or endpoint database. The endpoint set does represents a union of all endpoints of all biopsies. All the probes bracketed by two consecutive endpoints form an equivalence class. Any probe within a given equivalence class may be selected for use as a representative of that class. At step 2225, the equivalence classes of probes may be determined by forming a joint set of segment endpoints of all biopsies. Within each equivalence class, a representative probe may be selected to represent that equivalence class.

For purposes of facilitating an understanding of how loci correlating to outcome may be discovered in accordance with an embodiment of the invention, FIG. 23 is provided. FIG. 23 shows a table of six biopsies for which the survival status is known and for which the mean segment ratio for representative probe, probe$_i$, of each biopsy has been determined (from step 2230). The data provided in FIG. 23 is illustrative and pertains to only one selected probe.

At step 2240 of FIG. 22, for each representative probe, probe$_i$, the biopsies are ranked according to the mean segment ratio of that probe. The probes may be ranked in order from highest-to-lowest or lowest-to-highest. The result of the ranking of biopsies for the representative probe, probe$_i$, according to the mean segment ratio is shown on the right-hand side of the table of FIG. 24.

Referring back to FIG. 22, at step 2250, a minimum p-value is determined for each selected probe. A p-value is a value representing the likelihood of a particular set of circumstances occurring by chance, and a minimum p-value represents the largest or most unlikely particular set of circumstances to occur by chance. In this approach, the particular set of circumstances is the likelihood of the occurrence of a ratio of survivor to non-survivor for a given mean segment ratio. The p-value may be calculated as follows. For each mean segment ratio of a particular probe, it is determined how many survivors and non-survivors were found for probes having a mean segment ratio equal to, or greater than, the mean segment ratio of the particular probe. This survivor to non-survivor determination for a given mean segment ratio may be referred to as the survivor to non-survivor ratio. Then, a binomial distribution test is used to determine the likelihood of the survivor to non-survivor ratio occurring by chance. The result of the binomial distribution test yields a p-value.

Referring to FIG. 24, the ranking results from FIG. 23 are shown. In addition, four case numbers are shown to illustrate results of a calculated p-value for a given mean segment ratio. Beginning with case 1, which is shown pointing to a mean segment ratio of 4.18, the number of survivors and non-survivors is determined by examining the survival status of probes having a mean segment ratio equal to, or greater than, 4.18. In case 1, there is only one probe having a mean segment ratio having a mean segment ratio equal to, or greater than, 4.18. Thus, out of the four survivors, none correspond with a probe having at least a mean segment ratio of 4.18 and out of the two non-survivors, only one probe has a mean segment ratio of at least 4.18. The chance of such an occurrence (of survivors and non-survivors), as calculated by a binomial distribution test, is 0.333.

In case number 2, there are no survivors associated with probes having a mean segment ratio equal to, or greater than, 2.37. There are two non-survivors associated with probes having a mean segment ratio equal to, or greater than, 2.37. The chance of such an occurrence (of survivors and non-survivors), as calculated by a binomial distribution test, is 0.0667. This process may be repeated for each mean segment ratio. After the p-values are calculated for all probes, a minimum p-value is determined, which in this example is 0.0667, for selected probes.

Referring to FIG. 22, at step 2260, a discriminant threshold is assigned to each selected probe. The discriminant threshold is the mean segment ratio that gives the minimum p-value for a given probe. In the FIG. 23 example, the discriminant threshold is 2.37. The discriminant thresholds for each selected probe may be compiled and stored in a database.

At step 2280, the equivalence classes having a minimum p-value of at most a predetermined cutoff p-value are selected. Note that for any given equivalence class, the mean segment ratio of the probes in that class is the same. These selected equivalence classes may be called "seeds" and may be used to locate loci correlating with outcome, as indicated by step 2290. The loci correlating with outcome may be determined using the principle of minimum intersect. Use of the principle of minimum intersect to locate loci correlating with outcome is discussed in connection with FIG. 24, which shows how a locus may be discovered graphically. Though it is understood that in practice, the locus may be discovered using mathematical methods, the concept of finding the minimum intersect is discussed graphically to facilitate an understanding of the invention. For a given seed or equivalence class, all segments from the segmented genomic profiles of all biopsies having a mean segment ratio above the discriminant threshold for the given seed (if an amplification seed) or below 1 (if a deletion seed) are selected. An example of all segments falling into this category is illustrated graphically in FIG. 25, particularly denoted by bracket 2510. For all segments shown in bracket 2510, only the segments that completely overlap the seed are selected for inclusion into a subset, delimited by bracket 2520. In this example, only segments a, b, c overlap the seed. The intersect of the segments in the subset define the locus that correlates with outcome. The intersect of the segments is shown graphically by the dashed lines, resulting in the locus.

Figure 26:
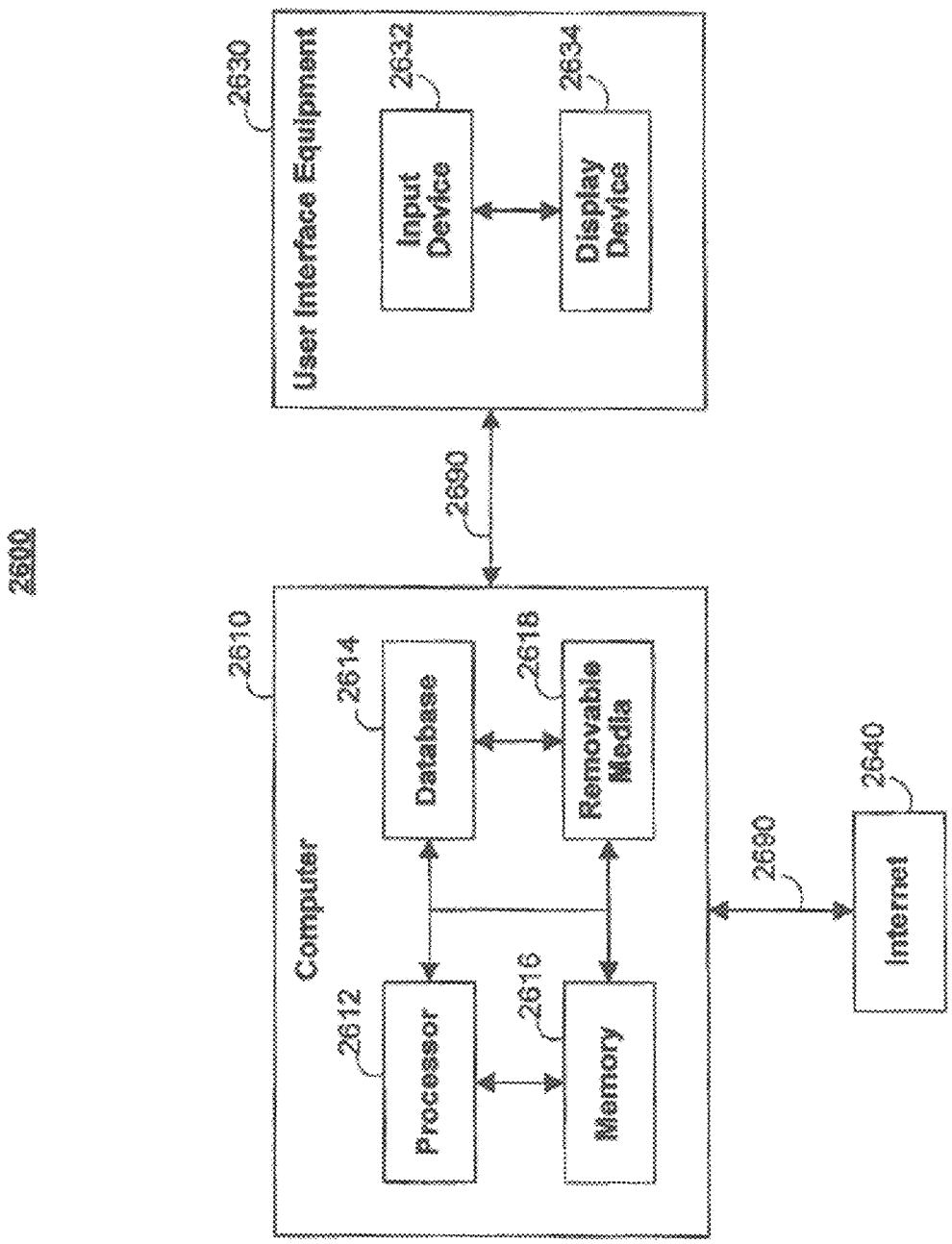
FIG. 26 shows a block diagram of a system that may be used to implement embodiment in accordance with the invention.
Figure 27:
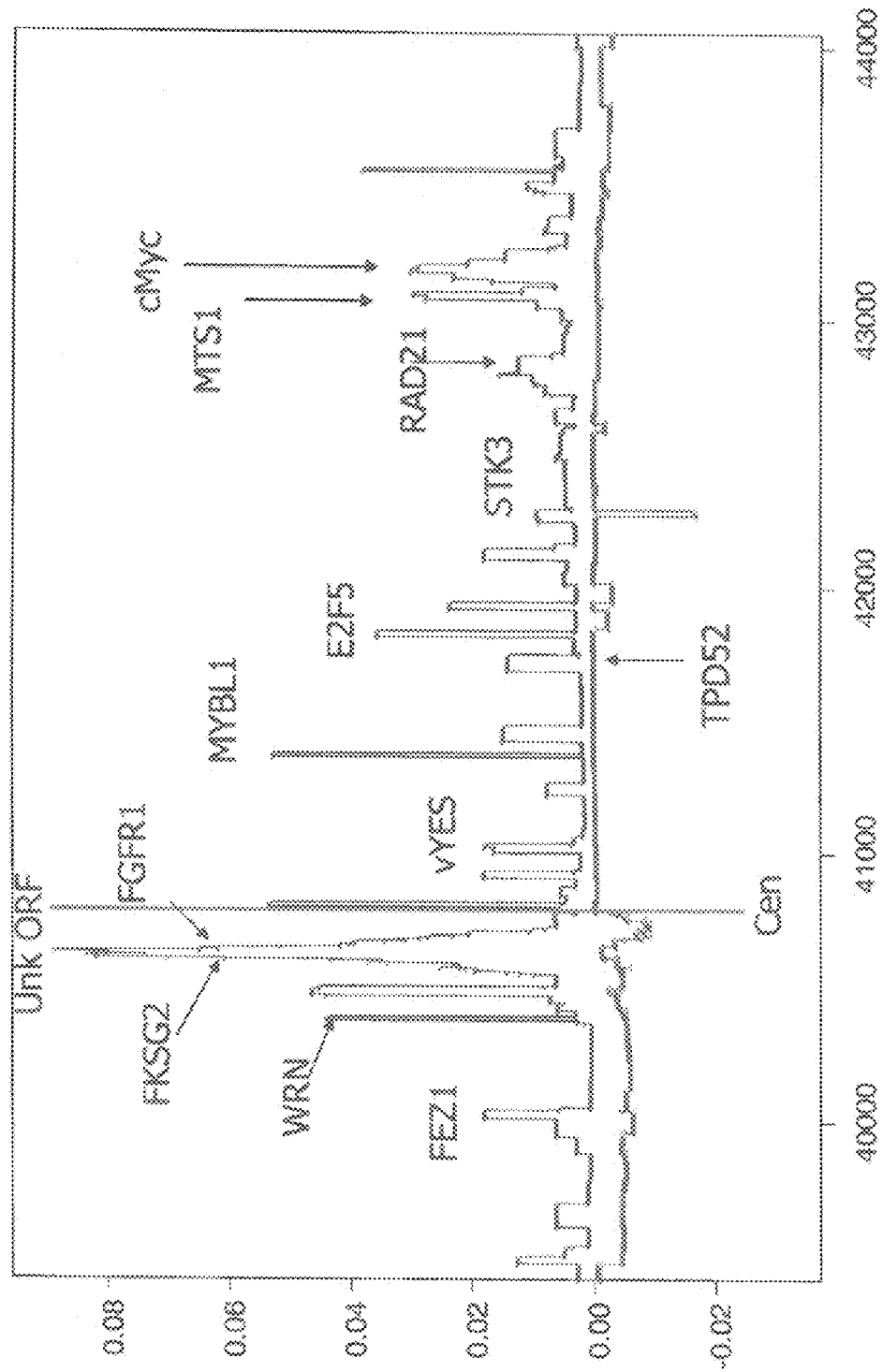
FIG. 27 shows a plot of fractional lengths of chromosome 8 as an illustrative example of a segmented genomic profile. Amplification of certain loci is observed, in particular, the UNK ORF.

The process for determining clinical outcome can be performed in accordance with the present invention using illustrative system 2600 shown in FIG. 26. System 2600 may include computer 2610, user interface equipment 2630, Internet 2640, and optional laboratory equipment (not shown). System 2600 may include multiple computers 2610 and user interface equipment 2630, but only one of each is illustrated in FIG. 26 to avoid complicating the drawing. Computer 2610 is shown connected to user interface equipment 2630, and Internet 2640 via communication paths 2690.

Computer 2610 may include circuitry such as a processor 2612, database 2614 (e.g., a hard-drive), memory 2616 (e.g., random-access-memory), and removable-media drive 2618 (e.g., a floppy disk drive, a CD-ROM drive, or a DVD drive). This circuitry can be used to transmit data to, from, and/or between user interface equipment 2630 and the Internet 2640. Computer 2610 may execute applications of the invention by responding to user input from user interface equipment 2630. Computer 2610 may also provide information to the user at user interface equipment 2630 with respect to results obtained from execution of a clinical outcome prognosis process according to embodiments of the invention. Database 2614 may store information such as, for example, a perturbation database.

User interface equipment 2630 enables a user to input commands to computer 2630 via input device 2632. Input device 2632 may be any suitable device such as a conventional keyboard, a wireless keyboard, a mouse, a touch pad, a trackball, a voice activated console, or any combination of such devices. Input device 2632 may, for example, enable a user to enter commands to generated, for example, a segmented genomic profile of an individual and to process profile to assign a probabilistic measure of one or more clinical outcomes of that individual. A user may view the results of processes operating on system 2600 on display device 2634. Display device 2634 may be a computer monitor, a television, a flat panel display, a liquid crystal display, a cathode-ray tube (CRT), or any other suitable display device.

Communication paths 2690 may be any suitable communications path such as a cable link, a hard-wired link, a fiber-optic link, an infrared link, a ribbon-wire link, a blue-tooth link, an analog communications link, a digital communications link, or any combination of such links. Communications paths 2690 are configured to enable data transfer between computer 2610, user interface equipment 2630, and Internet 2640.

Laboratory equipment may be provided in system 2600 so that biopsies may be processed and converted into data that can be analyzed using processed of the invention.

III. Methods for Identifying New Disease-Linked Genes that Contribute to Disease Phenotype and Clinical Outcome In certain embodiments, the invention relates to a method for identifying one or more potential disease-linked genetic loci, such as, for example, oncogenic loci in cancer, associated with a particular disease or, e.g., tumor type, comprising the steps of comparing genomic profiles generated according to one or more methods described herein, and identifying as disease-related oncogenic loci segments of the genome that correlate with high probability, alone or in combination, to probable clinical outcome for an individual patient having the particular tumor type or disease. In particular embodiments, the method includes obtaining and analyzing a genomic profile of a discriminator locus and identifying an oncogenic locus therein.

Similar to the discriminator loci, the disease-linked loci of the invention, such as oncogenic loci, are also useful diagnostic tools. Such disease-linked or oncogenic loci can further serve as targets for assessing existing therapy, or designing and identifying new therapies. It is envisioned that this discriminator method will be broadly applicable to identifying genetic loci, alone and in combination, that will be useful in diagnosing and choosing treatment methods for a wide variety of diseases other than cancer, i.e., those in which chromosomal rearrangements at one or a combination of particular genomic loci are associated with a condition, disorder or disease in a statistically relevant manner.

IV. Methods for Tumor Fingerprinting by Genomic Profiling Based on Relative Copy Number In certain embodiments, the invention relates to a method for determining whether two or more tumors present in an individual patient at the same time are related to each other, the method comprising the steps of:

(a) obtaining a segmented genomic profile, $GP_{(Ti)}$, of DNA extracted from one or more cells of each respective tumor, each $GP_{(Ti)}$ representing chromosome rearrangements present in the extracted DNA derived by measuring relative copy number of a plurality of discrete segments of the genome or one or more portions of the genome;

(b) comparing each $GP_{(Ti)}$ to each other $GP_{(Ti)}$;

wherein a match in one or more chromosomal rearrangements present in two or more $GP_{(Ti)}$s used to determine that one tumor is related to the other tumor.

In certain other embodiments, the invention relates to a method for determining the origin of one or more tumors, wherein said one or more tumors are present in a patient or in a biological sample, the method comprising the steps of:

(a) obtaining a segmented genomic profile, $GP_{(Ti)}$, of DNA extracted from one or more cells of each respective tumor, each $GP_{(Ti)}$ representing chromosome rearrangements present in the extracted DNA derived by measuring relative copy number of a plurality of discrete segments of the genome or a portion of the genome;

(b) comparing each $GP_{(Ti)}$ to one or more segmented genomic profiles in a database or clinical annotation table for tumors of known origin;

wherein a match in one or more chromosomal rearrangements present in one or more $GP_{(Ti)}$ is used to determine the origin of said one or more tumors.

The disclosure now being generally described, it will be more readily understood by reference to the following examples, which are included merely for purposes of illustration of certain aspects and embodiments of the present disclosure, and are not intended to limit the disclosure.

EXAMPLE 1

Breast Cancer Study and Respective Patient Populations

One goal of this study was to determine whether there were features in the genomes of tumor cells that correlated with clinical outcome in a uniform population of women with "diploid" breast cancers. This population was chosen because a significant number of cases culminate in death despite their clinical and histo-pathological parameters that would predict a favorable outcome. The subject population of 99 diploid cancers drew from a bank at the Karolinska Institute (KI), and was comprised of long term and short term survivors that were similar for node status, grade and size. For part of the analysis, additional studies in progress have been drawn upon, one using 41 aneuploid (defined as >2n DNA content, see Materials and Methods) cancers from KI, and the other using an additional 103 cancers from the Oslo Micrometastasis Study, Oslo, Norway (OMS). The latter set was not scored for ploidy and has only an average of eight years follow-up and is included in this study only for comparison of overall frequency of events. The individual genome profiles from the KI dataset but not the OMS dataset have been made available to the public on ROMA website (ROMA@cshl.edu). The OMS dataset will be posted as part of a second paper specifically dealing with that group. The clinical make-up of these sample sets with respect to clinical parameters is summarized in Table 1A.

The KI tumor dataset was assembled from a collection of over 10,000 fresh frozen surgical tumor samples with detailed pathology profiles and long term follow-up. The patients in this study underwent surgery between 1987 and 1992 yielding follow-up data for survival of 15-18 years. The sample set was assembled with the goal of studying a statistically significant population of otherwise rare outcomes, particularly diploid tumors that led to death within seven years, and aneuploid tumors with long term survival (described in Example 2: "Materials and Methods"). At the same time the sample was balanced with respect to tumor size, grade, node involvement and hormone receptor status. Treatment information is also available in the clinical table available for public access, however the sample set was not stratified according to treatment because the treatment groups are too fragmented to be significant. The Norwegian tumor set was selected from a trial previously described by Wiedsvang et al (Wiedswang et al., 2003) designed to identify markers associated with micrometastasis at the time of diagnosis (i.e. disseminating tumor cells in blood and bone marrow). The patients included in the study were recruited between 1995 and 1998, and fresh frozen tumors were available for a subset that was not selected for particular characteristics.

tumors at an unprecedented level of detail. At this resolution, narrow and closely spaced amplifications and deletions, some as narrow as 100 kbp, are clearly distinguished, and can be validated as discrete events by interphase FISH.

Cataloguing the events observed in these tumor sets has allowed us to create a high resolution map of the regions most frequently affected in this collection of tumors as compiled in Table 3. Further, examination of the ROMA patterns has led us to discern three distinct profile types, described as simplex, sawtooth and firestorm, that provide insights into the natural history of tumor development and moreover, provide prognostic and predictive information that may eventually be of use in clinical practice.

EXAMPLE 2

Breast Cancer Study: Materials and Methods

Patient Samples

A total of 140 frozen tumor specimens was selected from archives at the Cancer Center of the Karolinska Institute, Stockholm Sweden. Samples in this particular dataset were selected to represent several distinct diagnostic categories in order to populate groups for comparison by FISH and ROMA. Samples were grouped according to ploidy, tumor size, grade and 7-year patient survival. From a total of 5782

TABLE 1A

Distribution of patients and clinical parameters in the Swedish and Norwegian datasets. Numbers will not add up exactly because of partial information on certain individual cases.

| Karolinska Inst. Sweden | Total | Node (pos/neg) | Median Age At Diag. | Grade I/II/III | Size (mm) <20/>20 | PR* (+/−) | ER* (+/−) | ERBB2[+] amp/norm |
|---|---|---|---|---|---|---|---|---|
| Diploid (Survival >7 yr) | 60 | 28/31 | 52 | 8/11/33 | 19/41 | 41/9 | 43/7 | 3/57 |
| Diploid (Survival <7 yr) | 39 | 14/25 | 57 | 3/12/16 | 11/25 | 20/13 | 24/8 | 9/30 |
| Aneuploid | 41 | 28/13 | 49 | 0/2/22 | 21/20 | 14/19 | 25/10 | 15/26 |
| Oslo Micrometastasis Study (OMS) | 103 | 52/46 | 63 | 10/50/41 | 44/55 | 43/57 | 58/44 | 27/76 |

*progesterone (PR) and estrogen (ER) receptors measured by ligand binding; pos => 0.5 fg/μg protein
[+]ERBB2 amplification scored by ROMA as segmented ratio greater than 0.1 above baseline.

The study results described herein demonstrate a striking similarity of genome profiles from two different study populations, as well as the commonality of affected loci in aneuploid and diploid cancers. Significantly, a different genome profile was observed between diploid tumors with good and poor outcome. The complexity and the number of events, captured in a mathematical measure, suggest that genomic profiling may be useful for the molecular staging of breast cancer, and when validated by further studies, may prove useful for clinical practice.

The breast cancer study described herein is considered as the first large sample set of primary breast tumors profiled for copy number at a resolution of <50 kbp, and using a set of probes designed specifically to cover the genome evenly without regard to gene position. Coupled with a segmentation algorithm that accurately reflects event boundaries, this design has allowed us to examine genome rearrangements in cases, analysed for ploidy at the division for Cellular and Molecular Pathology at the Karolinska Hospital at the time of primary diagnosis (1987-1991), 1601 pseudo-diploids were available with complete clinical information including ploidy, grade, node status and clinical followup for 14 to 18 years. Of these, 4.0% or 64 cases were node-negative, non-survivors at 7 years and 8.0% or 127 cases were node positive non-survivors. Of these, 47 cases were locally available as frozen tissue and made up the group of node-negative and node-positive non-survivors. The diploid survivor group was selected from the remainder of the samples in order to match tumor size and grade. From the Oslo Micrometastasis study (OMS) (Wiedswang et al., 2003) fresh frozen samples from the primary tumor from 103 cases were available for analyses by ROMA.

The various groups and the numbers examined are show in the table that immediately follows:

TABLE 1B

| Group | No. in Sample | Sample # | Ploidy | Size (mm) | Node | Diff. | Grade | Outcome | Dist. Mets |
|---|---|---|---|---|---|---|---|---|---|
| 1 | 10 | WZ1-WZ10 | Aneu | >30 | neg | | IV | Living | No |
| 2a | 18 | WZ21-WZ38 | Aneu | 1.1-2.0 | +/peri | | IV | Dead | Yes |
| 2b | 12 | WZ65-WZ76 | Aneu | | neg | | III/IV | Dead | Yes |
| 3a | 10 | WZ11-WZ20 | Diploid | 0.7-2.4 | neg | | II/III | Dead | Yes |
| 3b | 9 | WZ77-WZ85 | Diploid | | + | | III | Dead | Yes |
| 3c | 16 | WZ86-WZ101 | Diploid | | | | | Dead | |
| 4a | 6 | WZ39-WZ44 | Diploid | 21-30 | neg | HiDif | I/II | Living | No |
| 4b | 7 | WZ45-WZ51 | Diploid | 21-30 | neg | LoDif | III | Living | No |
| 4c | 4 | WZ52-WZ55 | Diploid | 21-30 | + | HiDif | I/II | Living | No |
| 4d | 9 | WZ56-WZ64 | Diploid | 21-30 | +/peri | LoDif | III | Living | No |

Clinical Parameters

Status of the estrogen and progesterone receptors (ER, PR) was determined by ligand binding with a threshold value of >0.05 fg/µg DNA for classification as receptor positive for the Swedish samples. For the Norwegian samples automatic immunostaining was performed using mouse monoclonal antibodies against ER and PgR (clones 6F11 and 1A6, respectively, Novocastra, Newcastle upon Tyne, UK). Immunopositivity was recorded if ≥10% of the tumor cell nuclei were immunostained. Amplification of the HER2 gene was assessed by FISH (fluorescence in situ hybridization) on tissue microarray sections using the PathVysion HER-2 DNA Probe kit (Vysis Inc., Downers Grove, Ill. 60515, USA).

ROMA DNA Microarray Analysis

ROMA was performed on a high density oligonucleotide array containing approximately 85,000 features, manufactured by Nimblegen (Reykjavik, Iceleand). Hybridization conditions and statistical analysis have been described previously (Lucito et al., 2003).

Sample preparation, microarray hybridization and image analysis. The preparation of genomic representations, labeling and hybridization were performed as described previously. Briefly, the complexity of the samples was reduced by making Bgl II genomic representations, consisting of small (200-1200 bp) fragments amplified by adaptor-mediated PCR of genomic DNA. For each experiment, two different samples were prepared in parallel. DNA samples (10 µg) were then labeled differentially with Cy5-dCTP or Cy3-dCTP using Amersham-Pharmacia Megaprime labeling Kit, and hybridized in comparison to each other. Each experiment was hybridized in duplicate, where in one replicate, the Cy5 and Cy3 dyes were swapped (i.e. "color reversal"). Hybridizations consisted of 25 µL of hybridization solution (50% formamide, 5×SSC, and 0.1% SDS) and 10 µL of labeled DNA. Samples were denatured in an MJ Research Tetrad at 95° C. for 5 min, and then pre-annealed at 37° C. for 30 min. This solution was then applied to the microarray and hybridized under a coverslip at 42° C. for 14 to 16 h. After hybridization, slides were washed 1 min in 0.2% SDS/0.2×SSC, 30 sec in 0.2×SSC, and 30 sec in 0.05×SSC. Slides were dried by centrifugation and scanned immediately. An Axon GenePix 4000B scanner was used setting the pixel size to 5 µm. GenePix Pro 4.0 software was used for quantitation of intensity for the arrays.

Data Processing

Array data were imported into S-PLUS for further analysis. Measured intensities without background subtraction were used to calculate ratios. Data were normalized using an intensity-based lowess curve fitting algorithm. Log ratio values obtained from color reversal experiments were averaged and displayed as presented in the figures.

Statistics and Segmentation Algorithm

Segmentation views the probe ratio distribution as an ordered series of probe log ratios, placed in genome order, and breaks it into intervals each with a mean and a standard deviation. At the end of this process, the probe data, in genome order, is divided into segments (long and certain intervals), each segment and feature with its own mean and standard deviation, and each feature associated with a likelihood that the feature is not the result of chance clustering of probes with deviant ratios.

The ratio data was processed in three phases. In the first phase, the log ratio data was iteratively segmented by minimizing variance, then test the segment boundaries by setting a very stringent Kolmogorov-Smirnov (K-S) p-value statistic for each segment relative to its neighboring segment (p=$10^{-5}$). No segment smaller than 6 probes in length is considered. In the second phase, the "residual string" of segmented log ratio data was computed by adjusting the mean and standard deviation of each segment so that the residual string has a mean of 0 and a standard deviation of 1. "Outliers" were defined based on deviance within the population, and features are defined as clusters of outliers (at least two). In the third phase the features are assigned likelihood. A "deviance measure" was determined for each feature that reflects its deviance from the remainder of the data string. The residual string was then, in effect, either randomized or subjected to model randomization (i.e. look at the residual data in a randomized order) many times, and deviance measures of all features generated by purely random processes were collected. After binning the features by their length and their deviance measure, the likelihood was determined as to whether a given feature with a given length and deviance measure would have been generated by random processes if the probe data were noise.

Statistical analysis of segmented data was performed using R and S+ statistical languages. In particular, R Survival package was used for survival analysis.

Masking of Frequent CNPs

A large fraction the collection of genome profiles described herein are of a self-nonself type, i.e., a cancer genome and a reference genome originate in different individuals. As a result, not all of the relative copy number variation in the cancer genome is due to cancer: some of it reflects copy number polymorphisms (CNPs) present in the healthy genome of the affected individual. This non-cancerous signal can potentially contaminate subsequent analysis and must be filtered out. To this end, the collection of ROMA profiles derived from cancer-free genomes (about 500 cases in a most recent study) were examined. From that collection, the contiguous regions (here to be understood as series of consecutive ROMA probes) in the genome were determined where CNP frequencies satisfy two conditions: (a) these frequencies are higher than certain $f_e$ everywhere in the region; (b) these frequencies are higher than certain $f_s \geq f_e$ somewhere in the region. This determination was done separately for the amplification and for the deletion CNPs. With the present cancer-free collection the optimal values are $f_e=0.006$, $f_s=0.03$. Once the mask, i.e., the set of CNP-prone regions of the genome, was known, it was used for masking likely non-cancerous CNPs in cancer genome profiles. The masking algorithm for amplifications is described herein; the algorithm for deletions is completely analogous. If an amplified segment in a cancer genome profile falls entirely within a mask, a point (a probe) is selected at random in the segment, and the neighboring segments on the right and on the left are extended to that point. If one of the segment's endpoints is at a chromosome boundary, the neighboring segment is extended from the other endpoint to the boundary. In effect, the CNPs are excised from the profile in a minimally intrusive fashion.

Frequently Amplified and Deleted Loci

For the purpose of compiling a list of frequently amplified loci, amplification events are defined as follows. First, the logarithm of the relative copy number was computed for every segment in the genome (the segmentation method is described earlier in this section). Denote the resulting piecewise constant function $L(x)$, where x is the genome position. Next, (a) the values of $L(x)$ below a threshold t were replaced by 0. Then (b) event blocks, i.e., contiguous intervals of the genome such that $L(x)>0$ everywhere within the interval, were identified. For every block (c) an event extending over the entire block was added to the list of events. Next (d) a minimal nonzero value of $L(x)$ was found in each block, and that value is subtracted form $L(x)$ within that block. The steps (a) through (d) were iterated as long as $L(x)>0$ anywhere in the genome. The event counting rule for deletions was completely analogous, with obvious sign changes made throughout the description. A value of 0.1 was used for t in the present study. Once the events have been identified, every position in the genome was computed for an event density measure, defined as the sum of inverse lengths of all the events containing that position. Positions with the highest event density in every chromosome arm were then identified.

Fluorescence In-Situ Hybridization

FISH analysis was performed using interphase cells, and probes were prepared either from BACs or amplified from specific genomic regions by PCR. Based on the human genome sequence, primers (1-2 Kb in length) were designed from the repeat-masked sequence of each CNP interval, and limited to an interval no larger than 100 Kb. For each probe, a total of 20-25 different fragments were amplified, then pooled, and purified by ethanol precipitation. Probe DNA was then labeled by nick translation with SpectrumOrange™ or SpectrumGreen™ (Vysis Inc., Downers Grove, Ill.). Denaturation of probe and target DNA was performed at 90° C. for 5 minutes, followed by hybridization in a humidity chamber at 47° C. over night. The cover glasses were then removed and the slides were washed in 2×SSC for 10 minutes at 72° C., and slides were dehydrated in graded alcohol. The slides were mounted with anti fade mounting medium containing DAPI (4',6-diamino-2-phenylindole, Vectashield) as a counter-stain for the nuclei. Evaluation of signals was carried out in an epifluorescence microscope. Selected cells were photographed in a Zeiss Axioplan 2 microscope equipped with Axio Cam MRM CCD camera and Axio Vision software.

Probe Design for FISH

Hybridization probes for FISH were constructed in one of two methods. For the interdigitation analysis, probes were created from bacterial artificial chromosomes (BAC) selected using the UCSD genome browser. For the determination of copy number in the deletions and amplifications of the aneuploid tumors, probes were made PCR amplification of primers identified through the PROBER algorithm designed in this laboratory (Navin et al., 2006). Genomic Sequences of 100 kb containing target amplifications were tiled with 50 probes (800-1400 bp) selected with PROBER Probe Design Software created in our laboratory. PROBER uses a Distributed Annotated Sequence Retrieval request (Stein L, et al.) to request a genomic sequence and the Mer-Engine (Healy J, et. al.) to mask the sequence for repeats. Mer lengths of 18 that occur more then twice in the human genome (UCSC Goldenpath Apr. 10, 2004) with a geometric mean greater then 2 were masked with (N). Probes were selected from the remaining unmasked regions according to an algorithm to be published elsewhere.

Oligonucleotide Primers were ordered in 96-well Plates from Sigma Genosys and resuspended to 25 uM. Probes were amplified with the PCR Mastermix kit from Eppendorf (Cat. 0032002.447) from EBV immortalized cell line DNA (Chp-Skn-1) DNA (100 ng) with 55° C. annealing, 72° C. extension, 2 min extension time and 23 cycles. Probes were purified with Qiagen PCR purification columns (Cat. 28104) and combined into a single probe cocktail (10-25 ug total Probes) for dye labeling and Metaphase/Interphase FISH.

Measurement of DNA Content

The ploidy of each tumor was determined by measurement of DNA content using Feulgen photocyometry (Forsslund and Zetterberg, 1990; Forsslund et al., 1996). The optical densities of the nuclei in a sample are measured and a DNA index was calculated and displayed as a histogram (Kronenwett et al., 2004) Normal cells and diploid tumors display a major peak at 2c DNA content with a smaller peak of G2 phase replicating cells that corresponds to the mitotic index. Highly aneuploid tumors display broad peaks that often center on 4c copy number but may include cells from 2c to 6c or above.

Patient Consent

KI samples were collected from patients undergoing radical mastectormy at the Karolinska Insitutet between 1984 and 1991. This project was approved by the Ethical Committee of the Karolinska Institute, Stockholm, Sweden (approvalxx 2003). Samples in the OMS set were collected during 1995-98 after informed written consent and analysis protocols approved by the Regional Committee for Research Ethics, Health Region II, Oslo, Norway (approval S97103).

EXAMPLE 3

Processing Individual Cancer Genomes

All breast cancer genomes of the present study were examined with ROMA an array based hybridization method that utilizes genomic complexity reduction based on representations. In the present case, comparative hybridization using BglII representations were performed and arrays of 85,000 oligonucleotide (50-mer) probes with a Poisson distribution throughout the genome and a mean inter-probe distance of 35 kb (Lucito et al., 2003). In all cases, tumor DNA from a patient was compared to a standard unrelated male human genome. Hybridizations were performed in duplicate with color-reversal, and data was rendered as normalized ratios of probe hybridization intensity of tumor to normal.

The normalized ratios are influenced by many factors, including the signal-to-noise characteristics that differ for each probe, sequence polymorphisms in the genomes that affect the BglII representation, DNA degradation of the sample, and other variation in reagents and protocols during the hybridization and scan. Statistical processing called "segmentation" identifies the most likely state for each block of probes thus reducing the noise in the graphical presentation of the profile.

Within each raw ROMA profile segmentation places consecutive probe intensity ratios into a series of distinct distributions, reflecting the alterations that occur when blocks of the genome are amplified, duplicated or deleted. Several methods for segmentation have been published by us and others (Olshen et al., 2004; Daruwala et al., 2004), but in the present case, and in the interest of having very solid findings, a simplified method was utilized that recognizes distinct distributions of ratio based on minimization of variance and a Kolmogorov-Smirnov test with p-values set at $10^{-5}$ (see "Materials and Methods"). All methods converge on roughly the same segmentation pattern, especially at the boundaries, or edges, of events, but the simplified method used herein does not consider short segments (sets of probes less than six). On average, the resolution of the edges of a gene copy number alteration event is about 50 kb under our present conditions. Each probe ratio is reported herein as the mean of the medians of the ratios within the segment to which that probe belongs, producing a "segmented profile" of each cancer. Both raw ratios and segmented ratios have been made available to the public. Events less than six probes in length are, of course, visible in the unsegmented data and can be segmented by other methods, such as Hidden Markov Models (HMM), however these very narrow events do not affect the conclusions of this report and are excluded from the statistical analysis for simplicity.

Single nucleotide polymorphisms (SNPs), found in all profiles, are present only in methods that utilize restriction endonuclease-based representations. These are most often the result of sequence differences between sample and reference that alter the restriction sites employed in the representation process. For purposes of this report they merely contribute to noise and do not significantly affect segmentation. However, both rare copy number variants (CNVs) and more prevalent copy number polymorphisms (CNPs) (Sebat et al., 2004), will be present in any high-resolution copy number scan, regardless of method, when comparing one person to another. All of our tumor profiles are obtained by comparison to an unrelated standard normal male. If these CNPs and CNVs are not masked, analysis could mistake either for a cancer lesion. A list of common CNPs and rare CNVs has been compiled by profiling healthy cells from 482 individuals, and these were used to mask the "normal" CNPs in the tumor profiles herein as described in "Materials and Methods," which yielded a "masked segmented profile." The masked segmented profiles have been made available to the public. The collection of CNPs used for masking includes but is not limited to Scandinavian individuals and represents at most a few hundred probes being removed from consideration for segmentation in any sample. A CNP falling under a larger (cancer-related) event does not affect the segmentation of that event. Both the Kolmogorov-Smirnov segmentation software and the CNP masking algorithms will also be made available to the public in the forms of scripts interpretable by R or Splus statistical analysis software.

The mean ratios within segments are not directly proportional to true copy number. The unknown proportion of "normal" stroma in the surgical biopsies, the potential for clonal variation, and nonspecific hybridization background signal all contribute to a measured segment ratio below the actual copy number. Although ratios do not directly measure copy number, differences between the median ratios of segments do reflect differences in gene copy within a given experiment. This has been extensively validated by interphase fluorescent-in-situ-hybridization (see for example FIGS. 6A-6E).

EXAMPLE 4

Event Frequency Plots in Breast Cancer and their Correlation with Outcome

Figure 2A:
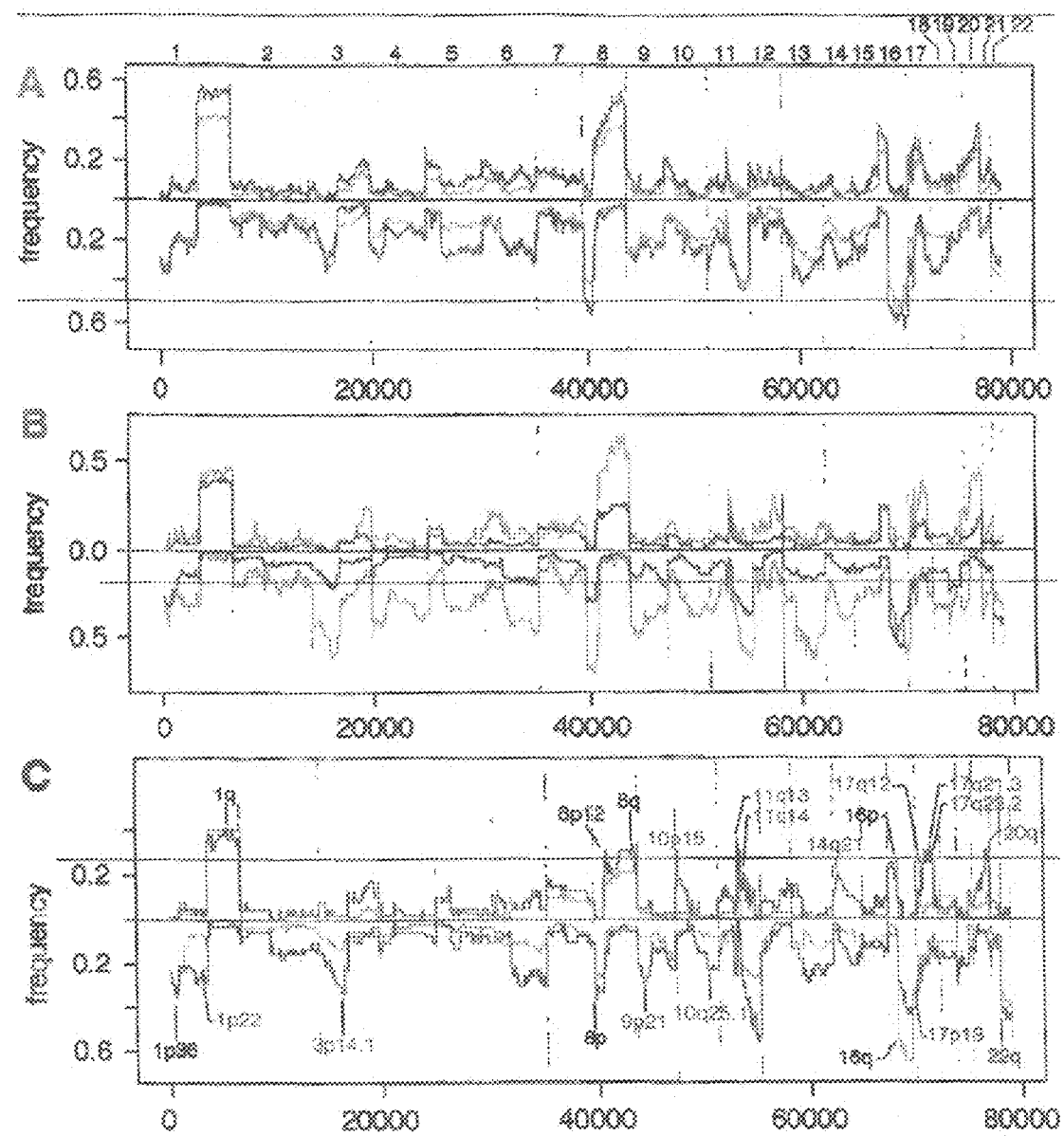
FIG. 2A shows the comparative frequency plots of amplification (up) and deletion (down) in various datasets. Frequency calculated on normalized, segmented ROMA profiles using a minimum of six consecutive probes identifying a segment with a minimum mean of 0.1 above (amplification) or below (deletion) baseline. Frequencies are plotted only for chromosomes 1-22. Panel A. Total Swedish dataset (red) vs. total Norwegian dataset (blue). Panel B. Swedish diploid subset (blue) vs. total Swedish aneuploid subset (red). Panel C. Swedish diploid 7 year survivors (red) vx. Swedish diploid 7 year non-survivors (blue).
Figure 2B:
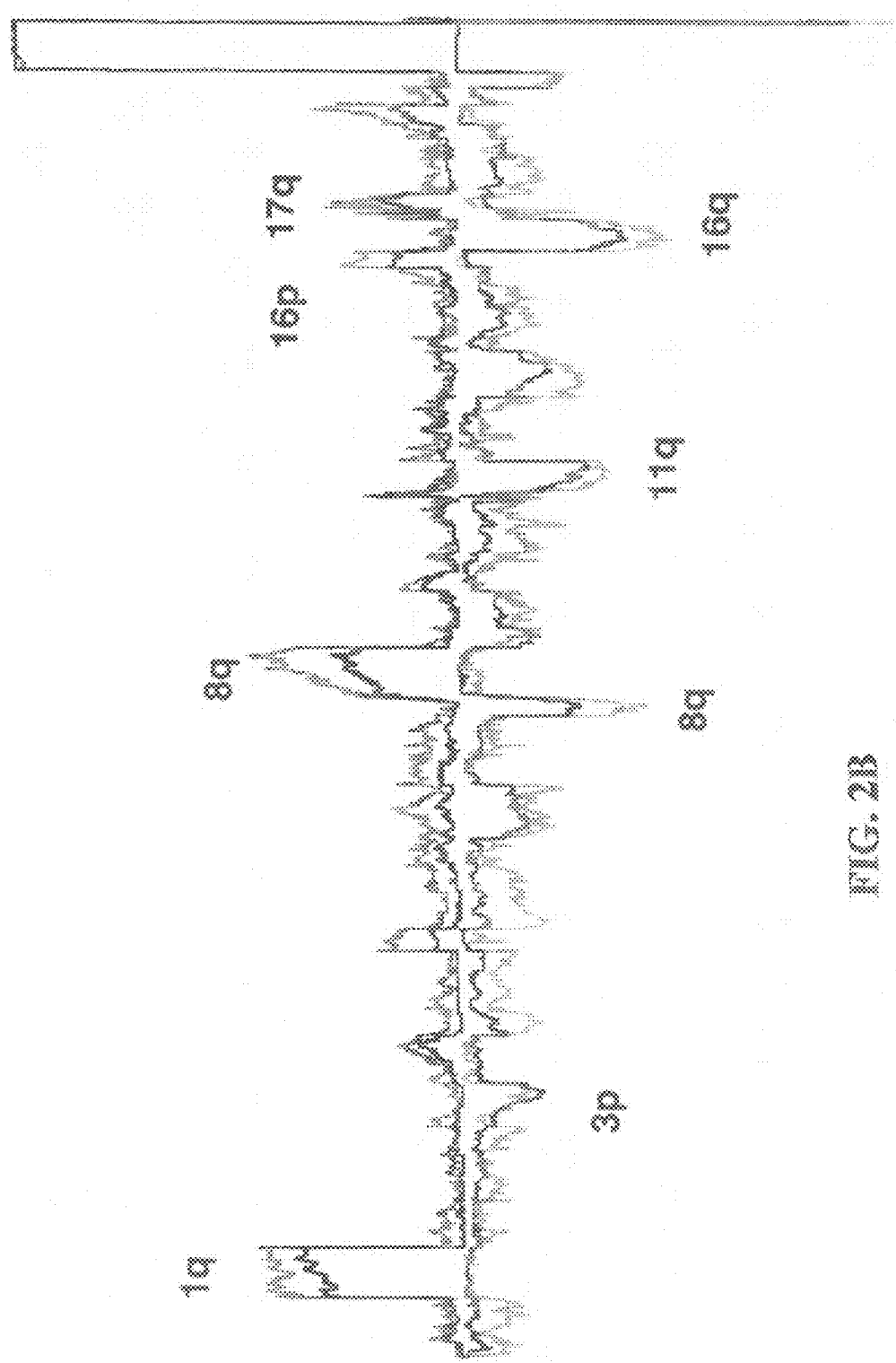
FIG. 2B shows combined frequency plots of all Sweden and all Norway tumors.

Once all the individual profiles are accumulated, they can be examined and compared as subpopulations. A straightforward, albeit simplistic, view of genome alterations is the frequency plot, a measure at each probe of the frequency with which the probe is amplified or deleted above a threshold in the genome profiles of a set of cancers. To obtain an overview of breast cancer lesions, plots from the Swedish group are shown, the Norwegian group, and for the combined set, plotting amplification frequencies as above the line and deletions below (FIG. 2A, panel A). Even at this crude view, it is evident that amplifications and deletions do not occur at random throughout the genome, and regions which are amplified tend not to be deleted, and vice-versa. Many of the well-known loci known to be deleted or amplified, such p53, CDKN2A, MYC, CCND1, and ERBB2, are at or near the centers of frequently altered regions. Additionally, there are frequent "peaks" and "valleys" where none of the familiar suspects are found. The data has been made available to the public, e.g., at the ROMA website, for the detailed inspection by the interested reader.

The Swedish (combined aneuploid and diploid) and Norwegian breast cancers display similar frequency profiles, with slightly higher frequencies in the Norwegian set. This discrepancy is most likely explained by the high proportion of diploid cancers in the Swedish set. While the Norwegian set is sequential and unselected, the Swedish set is over 70% pseudo-diploid, selected according to our working hypothesis that diploids would provide the most information about tumor development. When comparing the diploid to aneuploid Swedish cancers (FIG. 2A, panel B), similar profiles can be observed along with a similar difference in overall frequencies. This difference is not apparent when Swedish aneuploids are compared to the Norwegian group (data not shown). Thus the two cancer types, diploid and aneuploid, share the same loci of amplification and deletion.

The decreased frequency observed in the diploid set relative to the aneuploid set can be attributed to presence of long-term survivors in the former group. Frequency plots comparing 7-year ("long-lived") survivors to those that do not survive as long ("short-lived"), are shown in FIG. 2A, panel C. Clearly, designating a patient as a "survivor" or "non-survivor" at a specific time is not accurate in terms of the real progression of the disease. However, it is useful for understanding the relationship of disease progression to molecular events. "Seven years" is used as a demarcation because it reflects the point at which rate of death from cancer in the worst prognosis group drops to near zero. For the studies described herein demarcation values between 7 years and 10 years can be employed without changing the basic conclusions. It is quite apparent that there are fewer overall events, both amplifications and deletions, in the diploid survivors. Using 25 events as a divider, we obtain the most significant association of the long-lived versus the short-lived cancer patients, with a p-value of $4.2 \times 10^{-4}$ by Fisher's exact test.

EXAMPLE 5

Patterns of Genome Profiles

Visual inspection of segmented profiles suggests they come in three basic patterns (FIG. 3A), presented as qualitative heuristic tools for distinguishing apparently distinct processes of genomic rearrangement. The first profile pattern (FIG. 3A, left panel), called "simplex", has broad segments of duplication and deletion, usually comprising entire chromosomes or chromosome arms, with occasional isolated narrow peaks of amplification. Simplex tumors make up about 60% of the diploid dataset, while the rest fall into two distinct categories of "complex" patterns. One of these complex patterns is the "sawtooth," (FIG. 3A, middle panel) characterized by many narrow segments of duplication and deletion, often alternating, more or less affecting all the chromosomes. Little of the genome remains at normal copy number, yet the events typically do not involve high copy number amplification. Note that the scale of the Y-axis in FIG. 3A, middle panel is identical to that in FIG. 3A, left panel. It should be further noted that the X chromosome peak is often low in sawtooth profiles (e.g. WZ15 in FIG. 3A, middle panel) indicating that the X chromosome is not exempt from frequent loss in these tumors.

The third pattern (FIG. 3A, right panel) resembles the simplex type except that the cancers contain at least one localized region of clustered, relatively narrow peaks of amplification, often to very high copy number, with each cluster confined to a single chromosome arm. These clusters are denoted by the descriptive term "firestorms" because the clustering of multiple amplicons on single chromosome arms may reflect a concerted mechanism of repeated recombination on that arm rather than a series of independent amplification events. The high copy number of these amplicons is reflected in the scale of the Y-axis in FIG. 3A, right panel.

The two complex patterns, firestorm (25%) and sawtooth (5%), make up about 30% of the diploid tumors in this dataset. All profiles cannot be perfectly classified with this system, but the patterns appear to represent genomic lesions resulting from distinctly different mechanisms, and more than one mechanism may be operant to varying degrees within any given tumor.

A fourth type is the "flat" profile, in which no clear amplifications or deletions were observed other than copy number polymorphisms and single probe events, as discussed above, and the expected difference in the sex chromosomes. These examples are few in number (14/140) and are not presented graphically here. Some may result from the analysis of biopsies comprised mostly of stroma, or some may comprise a clinically relevant set of cancers with no detectable amplifications or deletions. Performing the analyses described in this paper with or without these flat profiles does not alter the conclusions drawn herein, hence they are included in the analyses presented here.

Figure 3A:
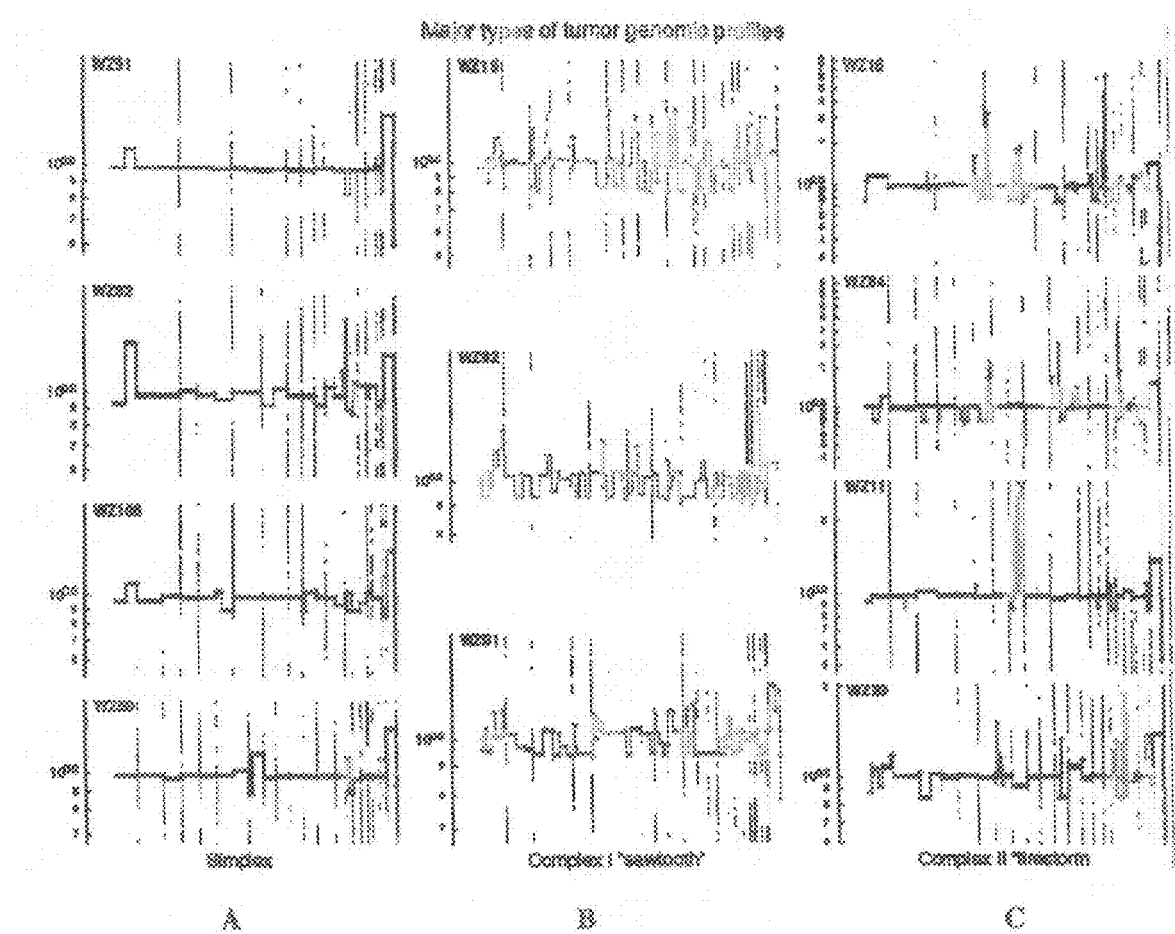
FIG. 3A shows the segmentation profiles for individual tumors representing each category: A. simplex; B. complex type I or 'sawtooth'; C. complex type II or 'firestorm.' Scored events consist of a minimum of six consecutive probes in the same state. Y-axis displays the geometric mean value of two experiments on log scale. Note that the scale of the amplifications in panel C is compressed relative to panels A and B due to the high levels of amplification in firestorms. Chromosomes 1-22 plus X and Y are displayed in order from left to right according to probe position.
Figure 3B:
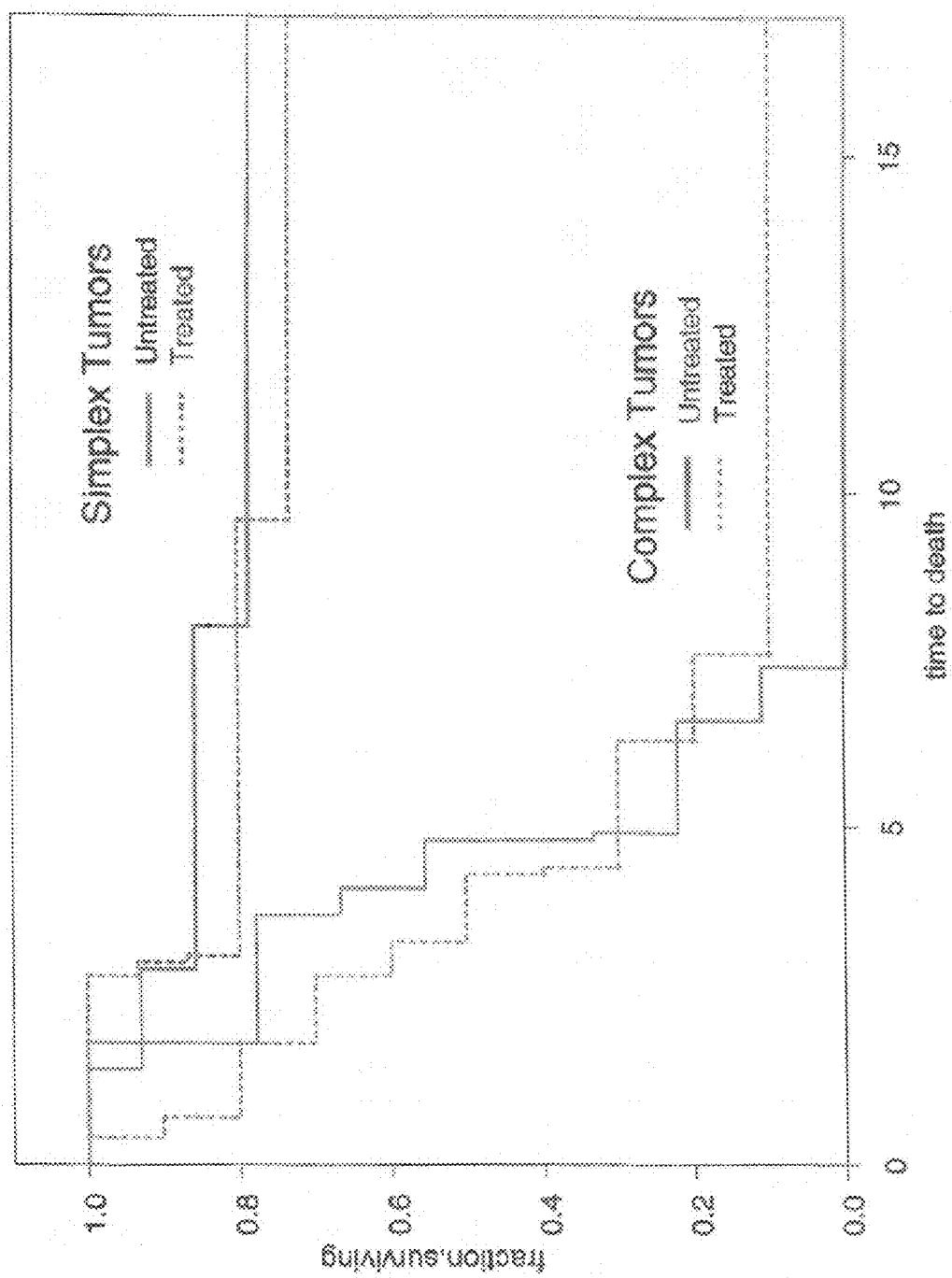
FIG. 3B compares tumors having complex (firestorm) genomic profiles against those having simplex genomic profiles, which demonstrates the correlation of a simplex genomic profile with survival and the correlation of a complex genomic profile with non-survival. The data were obtained from 47 node negative patients diagnosed in 1985-1989.
Figure 36:
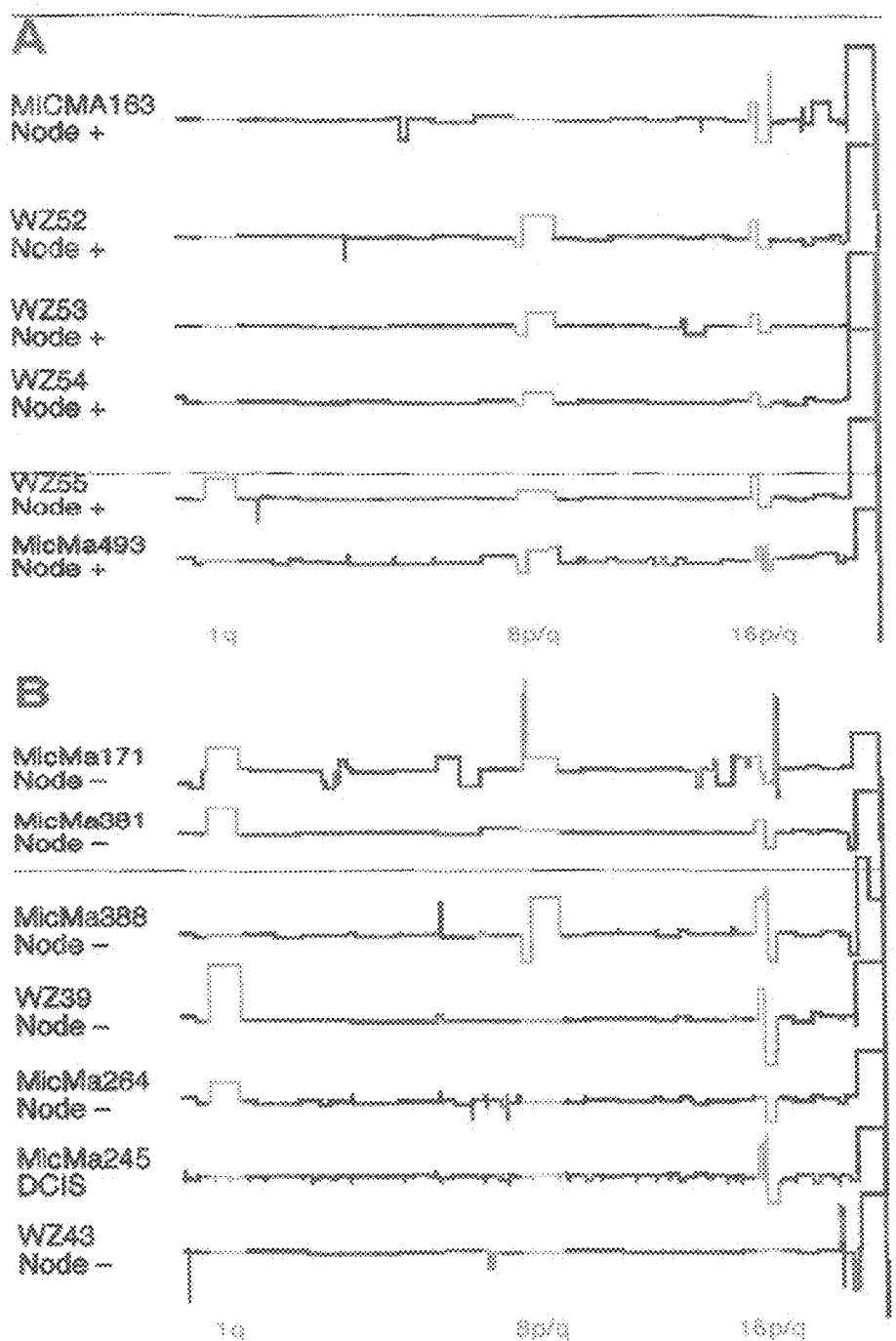
FIG. 36 shows a comparison of Grade I and DCIS tumors by ROMA. Segmented ROMA profiles of six node positive (panel A) and seven node negative (panel B) Grade I or DCIS tumors, representing of a total of 24 examples from the combined Swedish and Norwegian collections. Most frequent rearrangements are depicted in red.

Each of the three characteristic profiles shown by example in FIG. 3A provides a different insight into the biology of primary breast tumors. Simplex profiles are characterized by multiple duplications and deletions of whole chromosomes or chromosome arms. Moreover, certain specific chromosome arm gains and losses are highly favored and at least a subset appear in nearly all simplex tumors even those low grade tumors with less than three total events (FIG. 36). These lesions, all of which have been reported elsewhere by various methods (Kallioniemi et al., 1994; Nessling et al., 2005; Pollack et al., 2002; Ried et al., 1995; Tirkkonen et al., 1998), are: duplication of 1q, 8q and 16p; and deletion of 8p, 16q and 22q. Each of these shows high frequency in the set of diploid tumors (FIG. 2A, panel B). Not all of the events occur together in the same tumor, and there is not enough data as yet to test whether there is any intrinsic order to the timing of their appearance. However, the frequency of these specific changes remains constant when tumors from surviving patients (or those with few events) were compared with subsets of tumors that have poor survival (and many more total events) (FIG. 2A, panel B). One interpretation of these results is that in the early stages of tumor development cells undergo a subset of these specific gain or loss events as they give rise to proliferating clones. Subsequently, as these clones become less differentiated and gain potential to spread in the host, additional events accumulate. Thus it is reasonable to speculate that there are early and late genomic events that can be separated according to the degree of progression exhibited by the cancer.

Comparing FIG. 3A, left and right panels, it is apparent that the complex "firestorm" profiles display a spectrum of whole arm events reminiscent of the simplex profiles, but with the notable difference that certain chromosomes are covered almost completely with high copy number, closely-spaced amplicons. These features are called herein "firestorms" because they must be the result of violent disruptions of at least one homolog probably involving multiple rounds of breakage, copying, and rejoining to form chains of many copies (up to 30 copies in some cases, as measured by FISH). The copies apparently remain contiguous since in all cases tested, FISH results indicate that the copies fall in tight clusters within the nucleus.

Firestorms might arise through one or more previously characterized genetic mechanisms that have been previously characterized in cultured cells, such as breaks at fragile sites (Hellman et al., 2002; Coquelle et al., 1997) or recombination at pre-existing palindromic sites (Tanaka et al., 2005) perhaps by shortened telomeres. Initial joining of chromatids or chromosomes can lead to breakage-fusion-bridge (BFB) processes first described by McClintock (McClintock, 1938; McClintock, 1941). The process of chromatid fusion and bridge formation is often seen in tumor cells (Gisselsson et al., 2000; Shuster et al., 2000), and has the potential to result in repeated rounds of segmental amplification while remaining limited to a single arm as we have documented for firestorm events. This in itself might be a mechanism for genetic instability that augurs poor outcome, for example by enabling the cancer cell to "search" locally for combinations of genes that by amplification or deletion promote resistance to natural controls on cell growth, invasion or metastasis.

Finally, the alternative complex pattern, called "sawtooth," demonstrates the operation of a path to complex genomic alteration distinct from that leading to firestorms. In contrast to firestorms, the sawtooth pattern consists up to thirty duplication or deletion events, mostly involving chromosomal segments significantly broader than firestorm amplicons and distributed nearly evenly across the genome. Sawtooth profiles seldom show high copy number amplification as noted by the difference in the Y axis scale between FIG. 3A middle and right panels. Sawtooth profiles, like firestorms, are associated with a poor prognosis but their relatively high F index comes from the sheer number of events rather than the close spacing of the amplicons in firestorms. Taken together, these differences indicate that a genome-wide instability has been established in these tumors perhaps distinguishing a distinct ontogeny and pathway toward metastasis.

EXAMPLE 6

Firestorms

Interphase FISH was used to validate that segmentation is not an artifact of ROMA or statistical processing of ROMA data. Either BAC clones or probes created by primer amplification were labeled and hybridized to touch preparations of the same frozen tumor specimens profiled by ROMA ("Materials and Methods"). Probes were selected from 33 loci representing both peaks and valleys in the ROMA profile. In each case the segmentation values were confirmed by FISH. Representative instances of this data are shown herein for the complex pattern of amplification called "firestorms."

Firestorms are represented in ROMA profiles as clustered narrow peaks of elevated copy number. The pattern is limited to one or a few chromosome arms in each tumor with the remainder of the genome remaining more or less quiet, often indistinguishable from the simplex pattern. The individual amplicons in these firestorms are separated by segments that are not amplified, and are, in fact, often deleted, yielding a pattern of interdigitated amplification and LOH as shown for chromosome 8 (WZ11) in FIG. 6D and chromosome 11q (WZ17) in FIG. 6E. The phenomenon may be a result of sequential replication and recombination events or breakage and rejoining events that occur on a particular chromosome arm rather than a general tendency towards amplification throughout the genome.

Figure 6B:
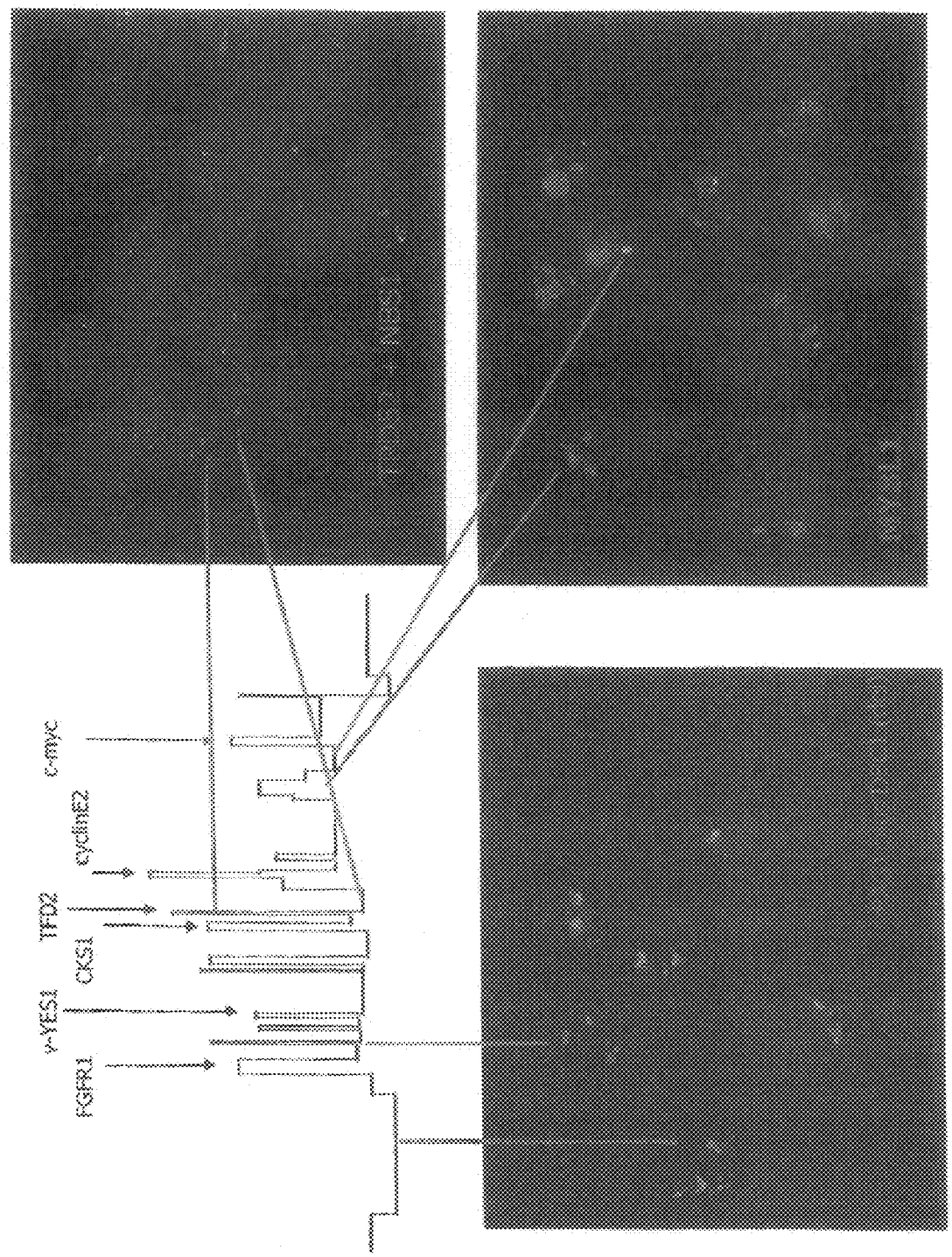
FIG. 6B is a duplicate of panel B of FIG. 6A, except that the lines between the ROMA genomic profile and the FISH photographs indicate corresponding genetic loci.
Figure 6C:
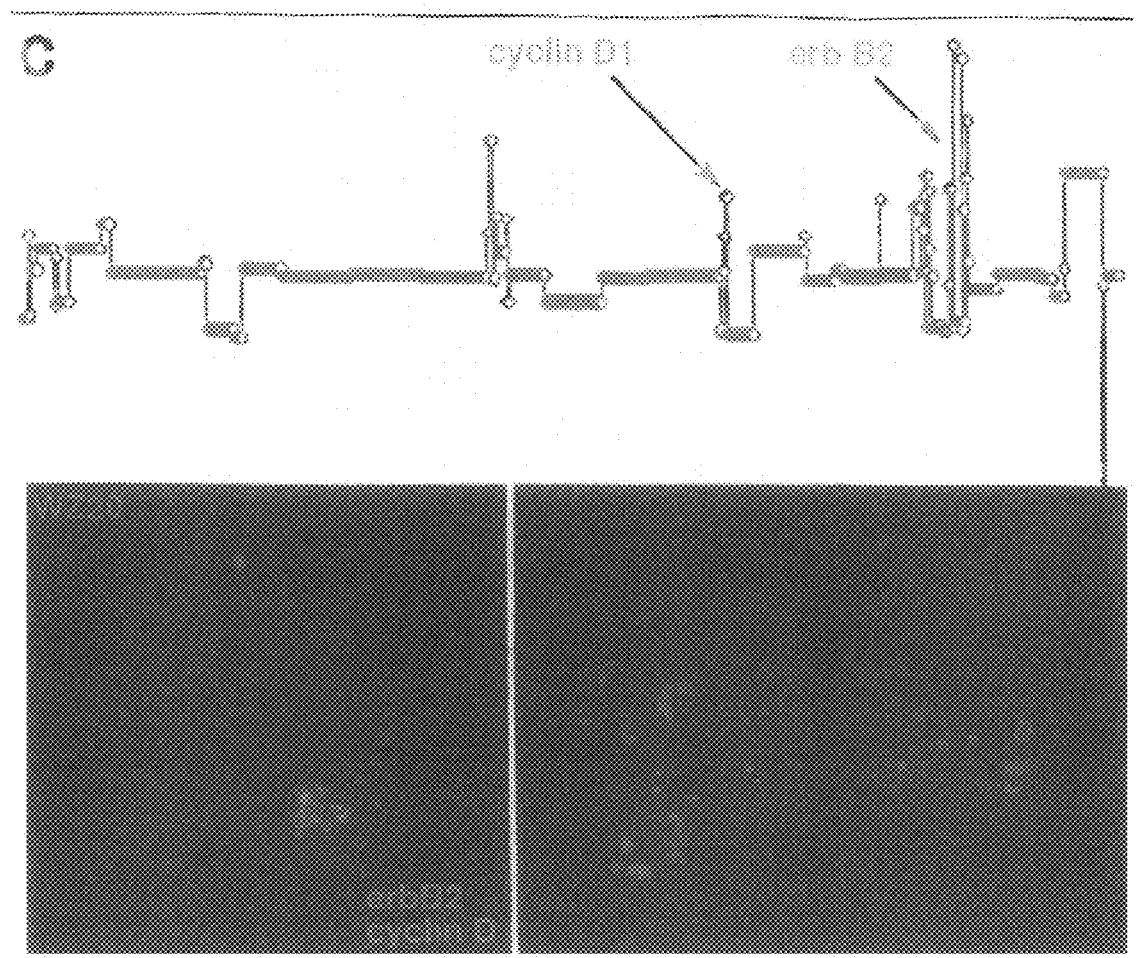
Figure 6D:
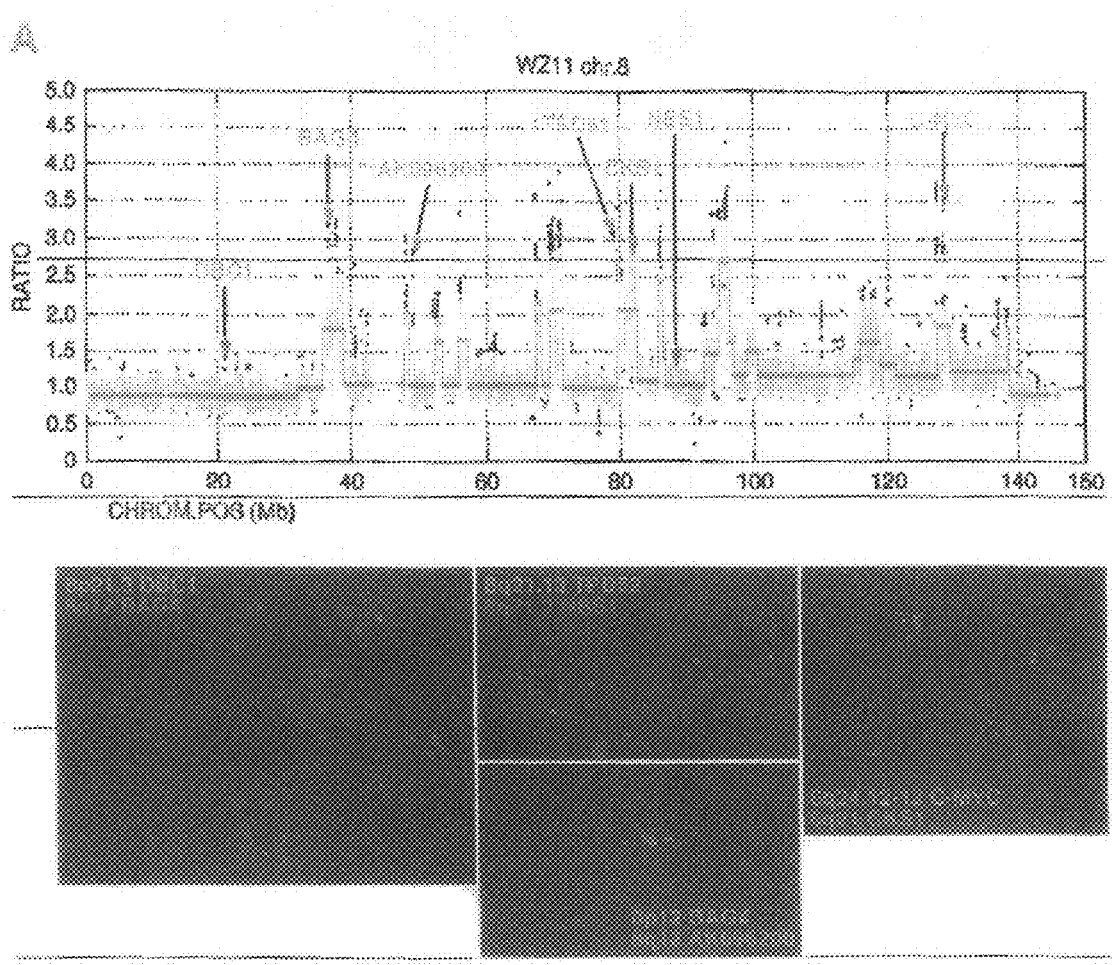
Figure 7:
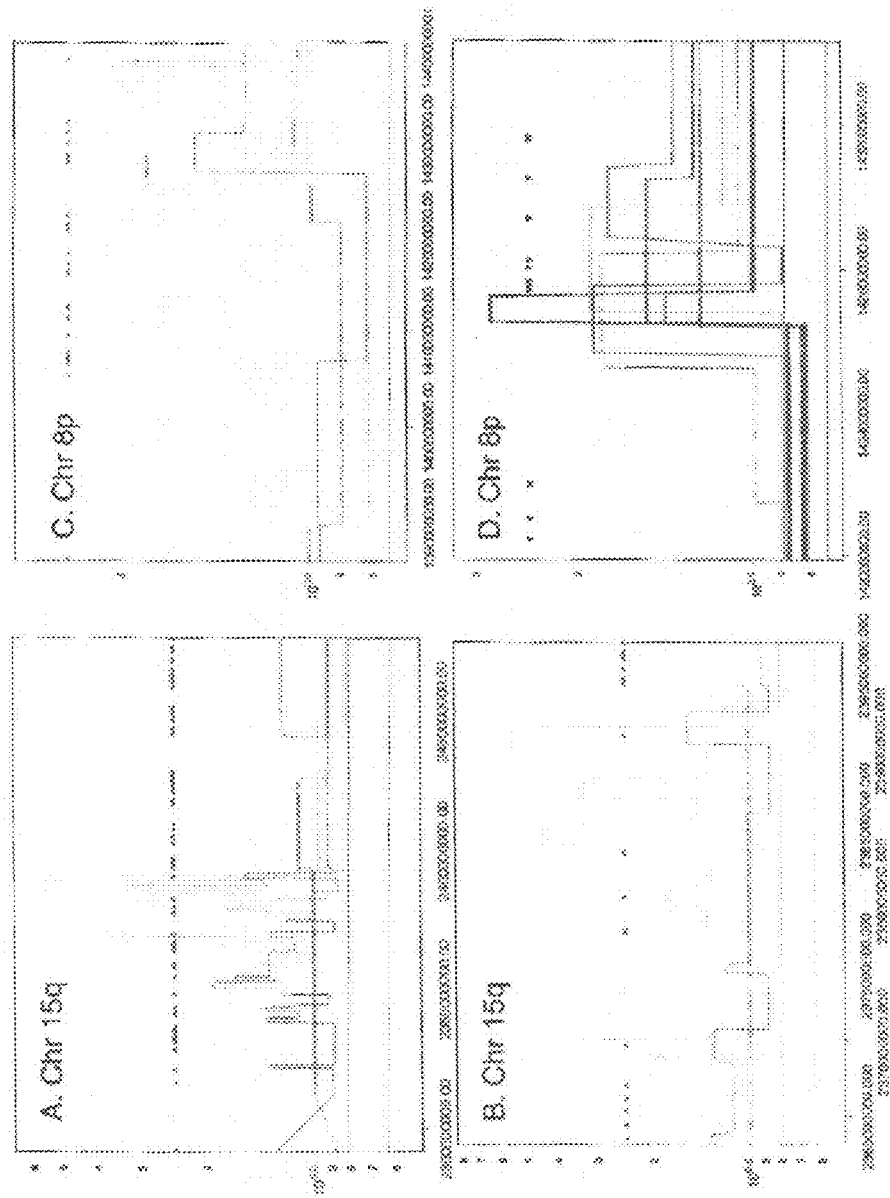
FIG. 7 shows that firestorms often amplify the same regions in separate tumors. A and B: Chromosome 15q from WZ16 (orange) and WZ30 (red). C and D: Centromere proximal region of chromosome 8p from WZ11 (green), WZ80 (red) and WZ16 (orange). Small triangles denote positions of putative oncogenes.
Figure 8:
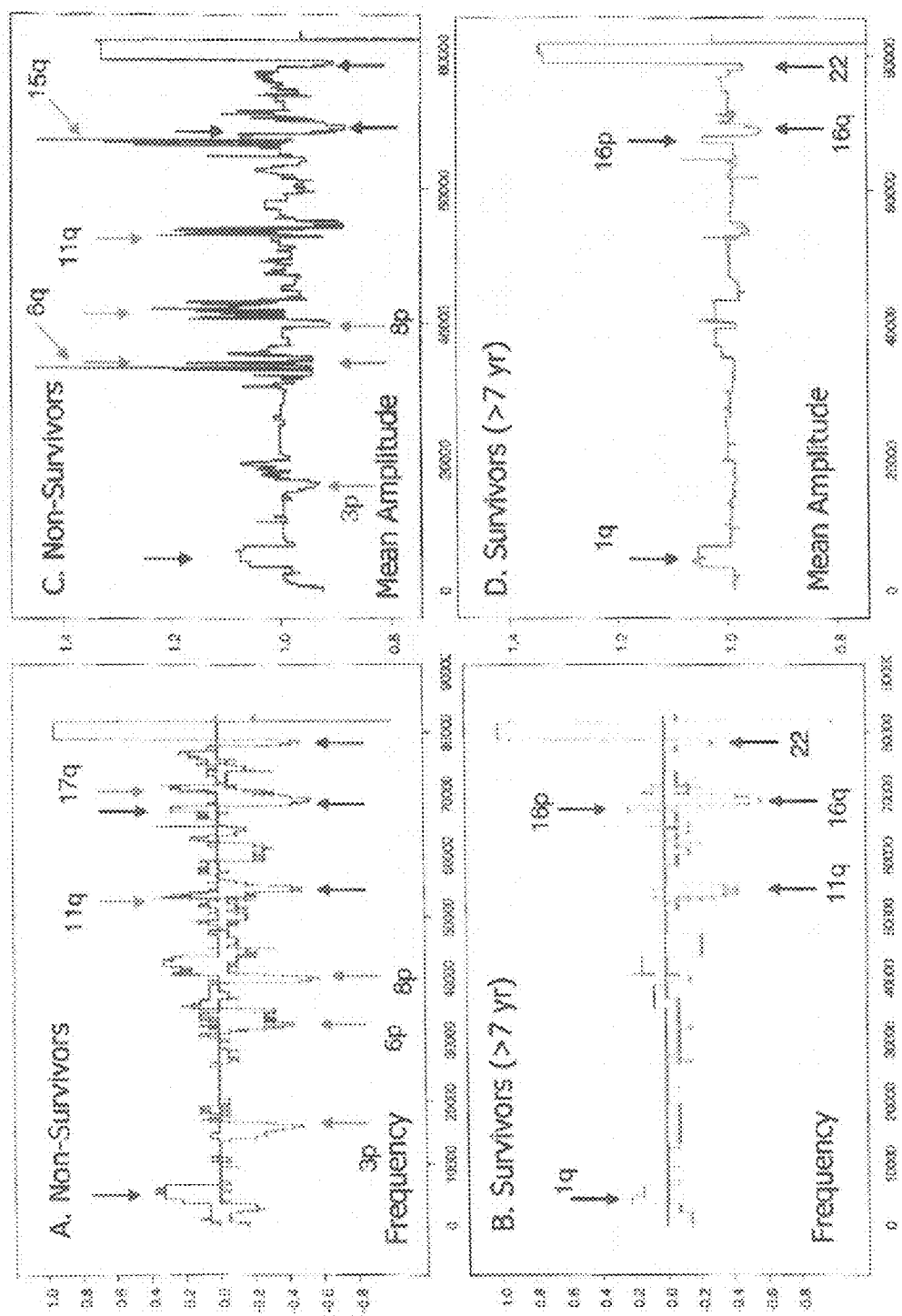
FIG. 8 shows a comparison of forty Grade III diploid tumors from eventual survivors vs. non-survivors. A and B: Frequency plots; C and D: Mean amplitude plots. Black arrows indicate events common to both classes. Red arrows indicate events enriched in the non-survivor class.
Figure 9:
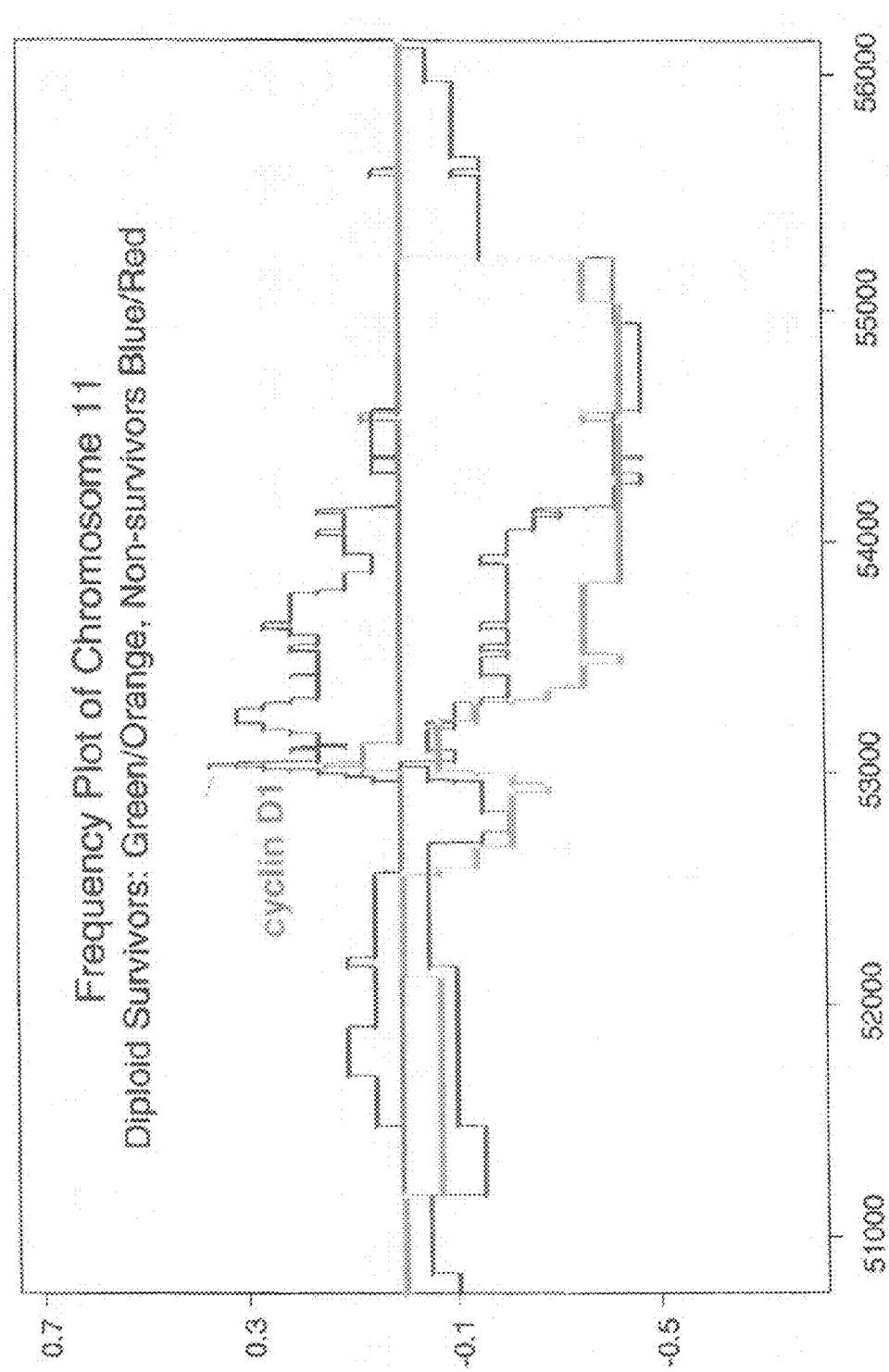
FIG. 9 shows the detailed frequency plot of chromosome 11 from the same samples shown in FIG. 8, showing the difference between survivors and non-survivors. Blue and red: Non-survivors; green and orange: Survivors.
Figure 10:
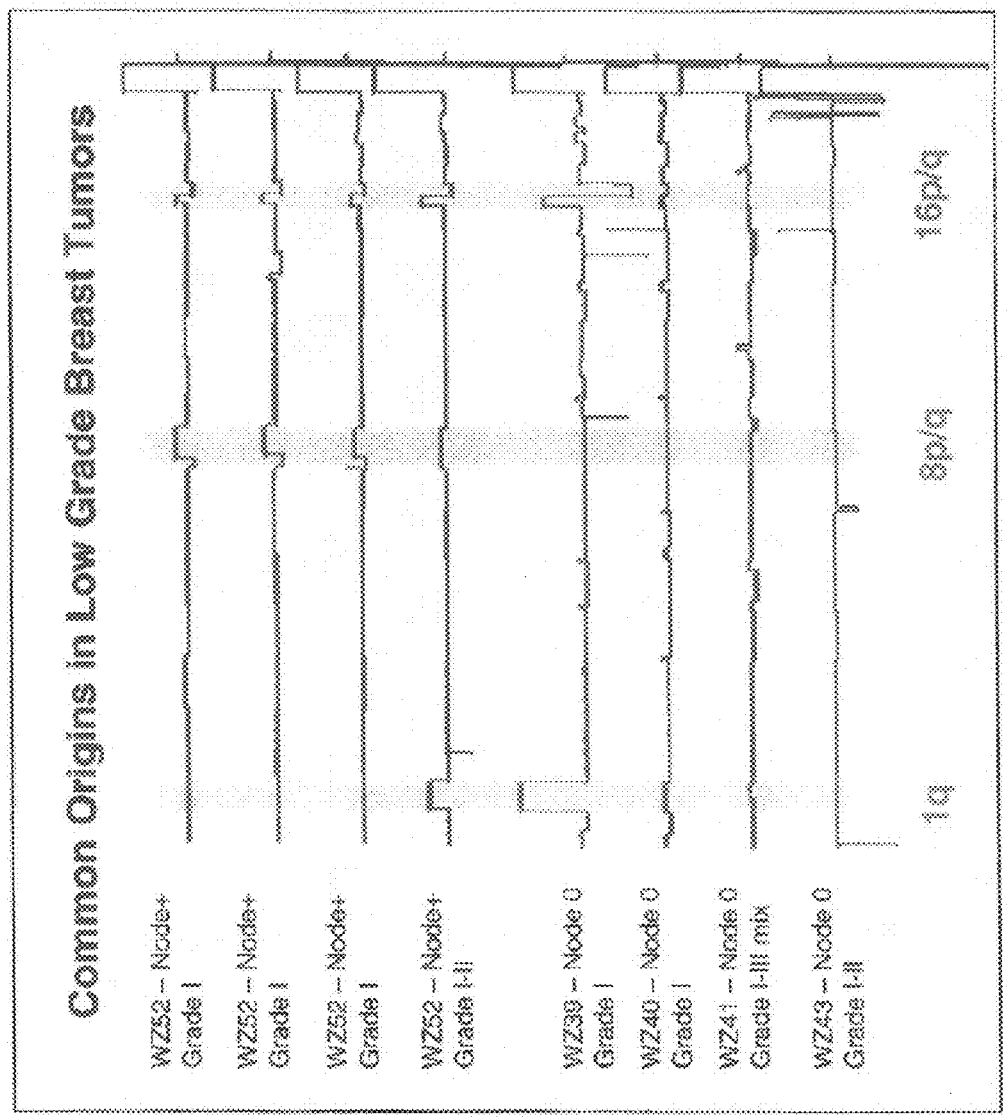
FIG. 10 shows a comparison of Grade I/II diploid tumors by ROMA. A total of ten low grade tumors were included in the dataset. The two samples not shown exhibited no detectable events. Regions of common chromosomal rearrangements are shaded. All of the shaded areas are among the most common sites of rearrangement in all breast tumors, collectively.
Figure 11:
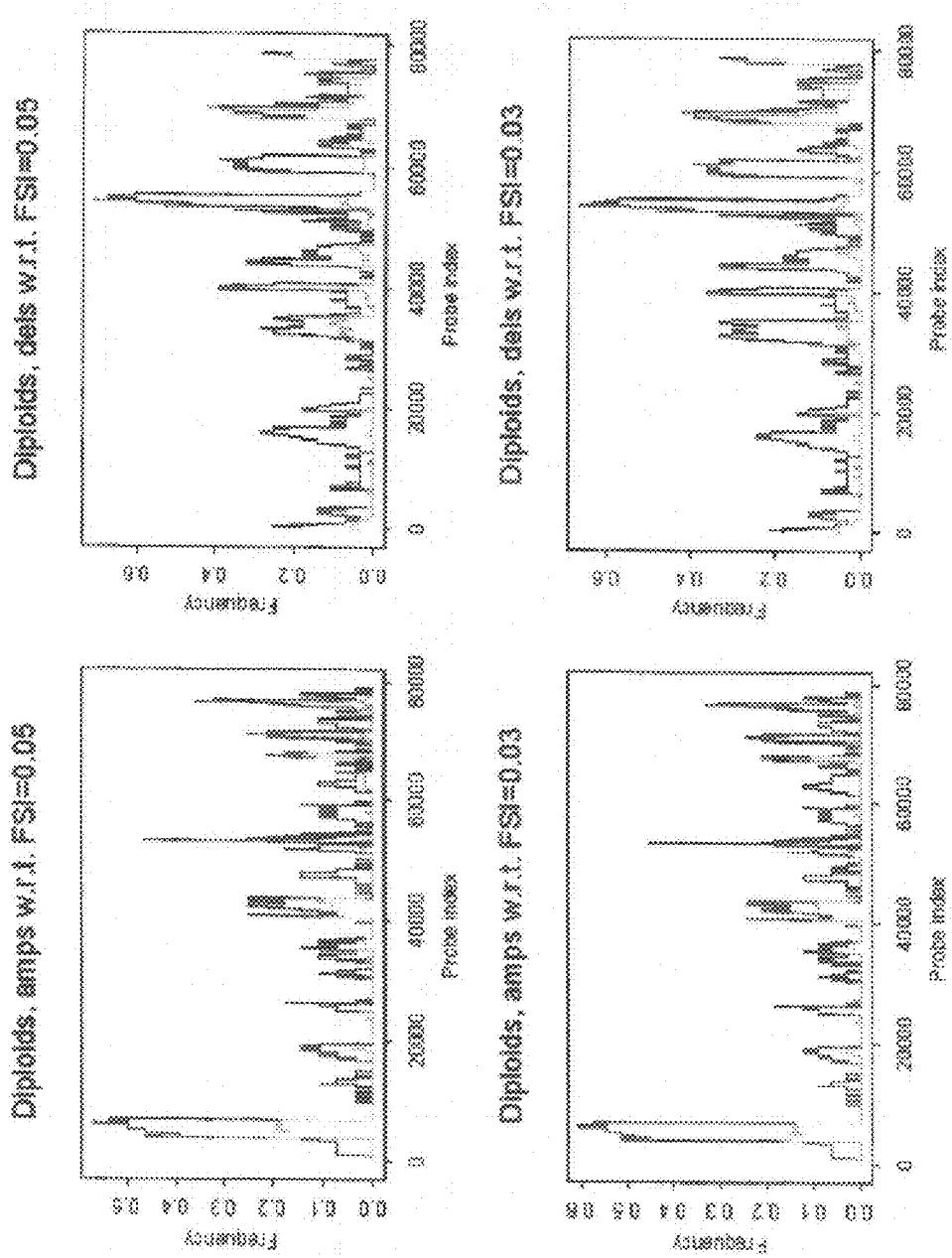
FIG. 11 shows frequencies of events in the Swedish diploid set divided into groups with high (black) and low (orange) values of the adjacent segment length measure.
Figure 12:
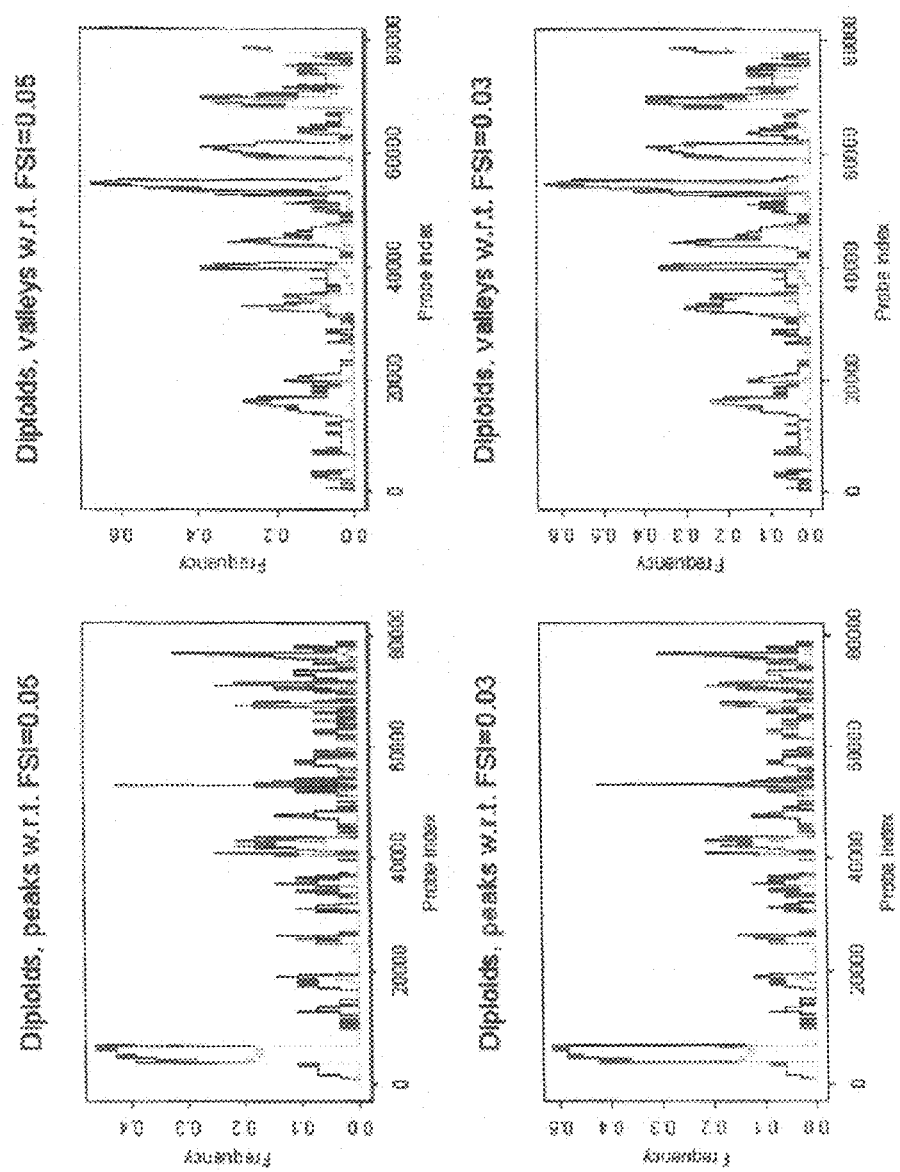
FIG. 12 shows frequencies of maxima and of minima in the Swedish diploid set divided into groups with high (black) and low (orange) values of the adjacent segment length measure.
Figure 13:
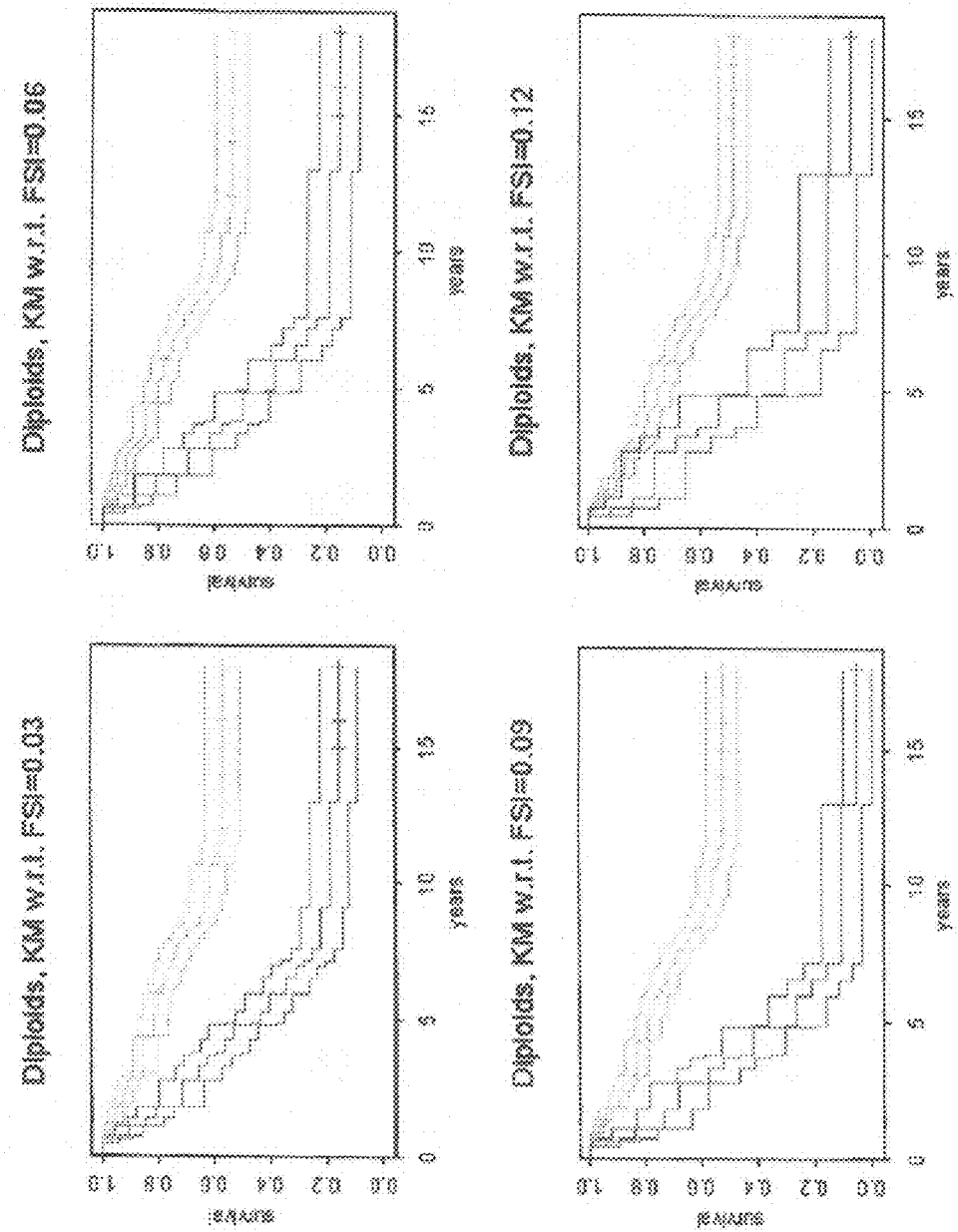
FIG. 13 shows Kaplan-Meier plots of the Swedish diploid subset divided into groups with high (blue) and low (orange) values of the adjacent segment length measure. The width of a strip reflects a 68.3% confidence interval.
Figure 14:
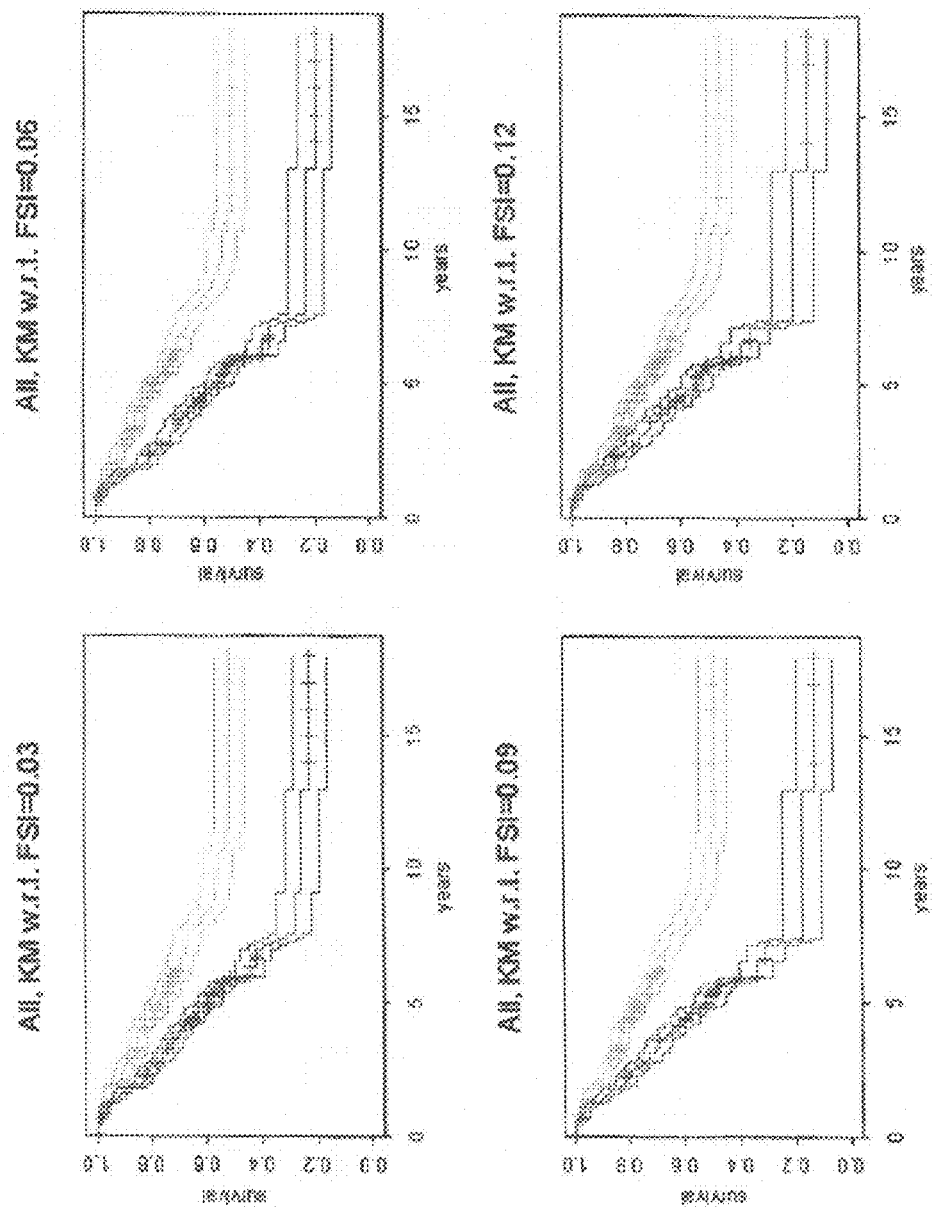
FIG. 14 shows Kaplan-Meier plots of the Scandinavian set divided into groups with high (blue) and low (orange) values of the adjacent segment length measure. The width of a strip reflects a 68.3% confidence interval.

One might imagine that the individual peaks in a cluster arise from clonal subpopulations within the tumor. They do not. The FISH images of FIGS. 6A-6E clearly indicate that amplifications at neighboring peaks of a cluster occur in the same cell. Moreover, they co-localize in the nucleus. In those cases where a cell harbors two firestorms, each on different chromosomes, these too occur in the same cell, but individually segregate within the nucleus by chromosome arm, as shown in FIG. 6C for CCND1 (cyclin D1) on chromosome 11q and ERBB2 (HER2neu) on 17q. A total of 18 BAC probes representing amplicons and intervening spaces were used in verifying the structure of chromosome 8 in WZ11 and 15 primer amplified probes were used for chromosome 11 in WZ17. Summary data for all probes has been made available to the public.

Figure 16:
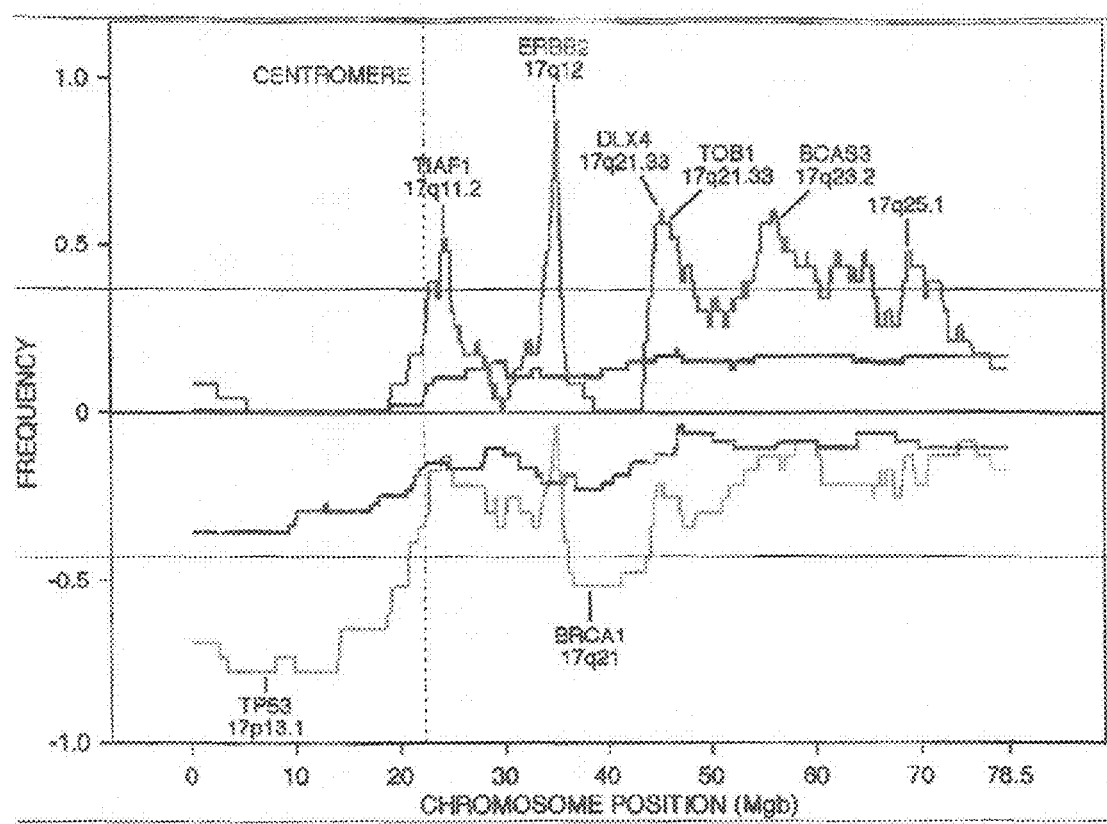
FIG. 16 shows the frequency plots of amplification and deletions in tumors containing clustered amplifications (firestorms) on chromosome 17. Lines represent histograms of the number of events for each probe in segmented ROMA profiles over threshold as in FIG. 3A for two subsets extracted from the combined Scandinavian dataset. Blue and red lines represent amplifications and deletions respectively in the subset of 23 tumors containing firestorms on chromosome 17, each showing clear peaks (valleys) of activity. Black and gray lines represent equivalent events in a set of 53 tumors in which firestorms are not observed on chromosome 17.

Firestorms have been observed at least once on most chromosomes in the tumors analyzed herein, but certain arms clearly undergo this process more frequently (see Table 2). In particular, chromosomes 6, 8, 11, 17 and 20 are often affected with 11q and 17q being the most frequently subject to these dramatic rearrangements. Within the latter, the loci containing CCND1 on 11q and ERBB2 on 17q are most frequently amplified and may "drive" the selection of the events. Chromosomes 6, 8 and 20 have comparable frequency of firestorms but the "drivers" for these events are less obvious. However, these potential "driver" genes are likely not to be the sole reason for the complex amplification patterns seen in firestorms. The other peaks in the firestorms are not randomly distributed. Each chromosome appears to undergo selective pressure to gain or lose specific regions as exemplified by the frequency plot of chromosome 17 shown in FIG. 16. The histogram of amplification (blue) or deletion (red) for 27 grade 2 and grade 3 tumors exhibiting firestorms on chromosome 17 from both Scandinavian datasets shows distinct peaks and valleys when compared to the equivalent histogram for a set of tumors of equivalent grade but without chromosome 17 firestorms (black and gray histograms). As shown in FIG. 16 there is a strong tendency for deletion of the distal p arm including TP53 and for deletion of 17q21 including BRCA1. Conversely, there are at least four distinct peaks of high frequency amplification on the long arm of 17 in addition to the peak containing ERBB2. As noted in the figure, several genes of interest for breast cancer are located near the epicenters of these peaks, including TOB1 ("transducer of ERBB2") and BCAS3 ("breast cancer amplified sequence"). Furthermore, in contrast to accepted dogma (Jarvinen and Liu, 2003) a fraction of firestorms on 17q, (5-10%) do not include amplification of ERBB2, giving weight to the notion that other loci in the region may contribute to oncogenesis. In contrast, broad duplications and deletions are detectable in the non-firestorm subset but they do not form clear peaks.

TABLE 2

Occurrence of firestorms in the complete Swedish tumor set including both aneuploids and diploids, by chromosome arm, excluding X and Y. Firestorms defined as three segmented events of any width over a threshold ratio of 0.1 on a single arm.

| | Chrom. Arm | | | | | | | | | | |
|---|---|---|---|---|---|---|---|---|---|---|---|
| | 1p/q | 2p/q | 3p/q | 4p/q | 5p/q | 6p/q | 7p/q | 8p/q | 9p/q | 10p/q | 11p/q |
| Firestorms | 2/3 | 0/3 | 0/1 | 0/0 | 2/0 | 3/8 | 1/1 | 6/8 | 0/0 | 0/3 | 1/16 |

| | Chrom. Arm | | | | | | | | | |
|---|---|---|---|---|---|---|---|---|---|---|
| | 12p/q | 13q | 14q | 15q | 16p/q | 17p/q | 18p/q | 19p/q | 20p/q | 21q | 22q |
| Firestorms | 3/3 | 4 | 2 | 4 | 0/1 | 0/16 | 0/0 | 3/3 | 1/7 | 0 | 0 |

EXAMPLE 7

Frequently Amplified and Deleted Loci

It is of interest to note the regions that are most frequently amplified or deleted in a large dataset such as the one presented here. There is no single accepted algorithm for deciding which regions are of most interest and the parameters used will depend on the goals of the individual researcher. In Table 4 the results of one such algorithm were presented (see "Frequently Amplified and Deleted Loci" in "Materials and Methods") that reflects a component of frequency at any locus plus a factor that gives weight to the inverse of the width of any given event. The latter is based on the rationale that narrow events centered on a given locus should carry more weight than a broad event that happens to encompass that locus. In the table, the relative value for each locus is shown in the Index column. Representative genes that have some potential relation to breast cancer are included for reference purposes. While a number of specific amplicons have been reported previously for specific chromosomes, such as 11q (Ormandy et al., 2003) and the ERBB2 region of 17q (Jarvinen and Liu, 2003), no other report appears to have catalogued a dataset of comparable size and resolution permitting this level of detailed analysis. For example, Ormandy et al (Ormandy et al., 2003) report three narrow (<2 Mb) "core" amplicons in the 11q13 bands along with an independent 17 Mb amplicon covering spanning the other three. The analysis described herein yields roughly equivalent peaks of high significance (index value) at 11q13.3 and 13.4 in agreement with their data, along with at least 11 additional distinct peaks where repeated amplification events have occurred on that arm. A graphical version of this analysis will be made available to the public along with the other ROMA data on the ROMA website.

TABLE 3

Loci that undergo frequent amplification or deletion among members of the Swedish diploid tumor set.

| Chromosome position | Band | Gene symbol | Index | miRNA |
|---|---|---|---|---|
| Amplifications | | | | |
| Chr1: 142,883,026-145,311,463 | q21.1 | Various | 0.05 | |
| Chr3: 157,052,165-157,422,481 | q25.1 | GMPS | 0.11 | |
| Chr3: 197,059,401-199,326,099 | q29 | Various | 0.03 | |
| Chr4: 9,799,463-10,002,778 | p16.1 | None | 0.06 | |
| Chr5: 142,399-980,973 | p15.33 | Various | 0.05 | |
| Chr6: 15,331,503-16,100,229 | p22.3 | JARID2 | 0.07 | |
| Chr6: 116,304,898-116,752,141 | q22.1 | FRK | 0.14 | |
| Chr6: 144,141,338-144,778,980 | q24.2 | PLAGL1 | 0.07 | |
| Chr6: 151,805,890-152,531,243 | q25.1 | ESR1 | 0.07 | |
| Chr7: 54,880,176-56,021,876 | p11.2 | EGFR | 0.07 | |
| Chr7: 81,363,861-81,906,266 | q21.11 | CACNA2D1 | 0.065 | |
| Chr8: 31,389,288-32,073,293 | p12 | NRG1 | 0.06 | |
| Chr8: 37,655,817-38,111,519 | p12 | GPR124 | 0.17 | |
| Chr8: 48,351,903-48,797,073 | q11.21 | Unknown | 0.10 | |
| Chr8: 56,119,985-57,277,665 | q11.21 | LYN | 0.08 | |
| Chr8: 67,551,628-68,252,014 | q13.1 | Various | 0.08 | |
| Chr8: 95,078,426-96,623,917 | q22.1 | CCNE2 | 0.08 | |
| Chr8: 127,391,153-127,771,453 | q24.21 | FAM84B | 0.07 | |
| Chr8: 128,345,346-129,528,851 | q24.21 | MYC | 0.06 | |
| Chr8: 138,413,221-138,669,893 | q24.23 | None | 0.10 | |
| Chr11: 50,335,199-56,087,807 | p11.2 | Olfactory receptors | 0.05 | |
| Chr11: 56,481,254-56,801,992 | q11.2 | AGTRL1 | 0.08 | |
| Chr11: 57,968,971-58,155,437 | q12.1 | LPXN | 0.13 | |
| Chr11: 68,970,345-69,253,791 | q13.3 | CCND1 | 0.35 | |
| Chr11: 69,301,635-69,776,764 | q13.3 | FGF3 | 0.40 | |
| Chr11: 73,028,223-73,740,133 | q13.4 | RAB6A | 0.10 | |
| Chr11: 77,019,036-77,608,921 | q13.5 | RSF1 | 0.19 | |
| Chr11: 78,852,218-79,294,501 | q14.1 | None | 0.09 | |
| Chr11: 82,552,236-83,111,027 | q14.1 | DLG2 | 0.07 | |
| Chr11: 89,502,943-90,173,207 | q14.3 | Various | 0.09 | |
| Chr11: 92,206,944-92,432,032 | q21 | FAT3 | 0.14 | |
| Chr11: 101,466,054-101,665,638 | q22.2 | YAP1 | 0.10 | |
| Chr11: 105,134,747-105,674,579 | q22.3 | Various | 0.10 | |
| Chr11: 115,891,412-116,980,657 | q23.3 | Various | 0.05 | |
| Chr16: 15,064,442-16,759,687 | p13.11 | Various | 0.10 | mir-484 |
| Chr16: 32,082,910-33,715,287 | p11.2 | Various | 0.12 | |
| Chr16: 59,205,171-59,350,595 | q21 | None | 0.10 | |
| Chr17: 14,364,446-14,766,493 | p12 | Unknown | 0.09 | |
| Chr17: 20,559,616-21,208,425 | p11.2 | MAP2K3 | 0.11 | |
| Chr17: 26,949,618-27,884,440 | q11.2 | Various | 0.10 | |
| Chr17: 34,786,206-35,245,713 | q21.1 | ERBB2 | 0.18 | |
| Chr17: 44,669,729-45,499,914 | q21.32 | Various | 0.08 | |
| Chr17: 55,947,700-56,583,137 | q23.2 | BCAS3 | 0.10 | |
| Chr20: 51,026,986-51,790,932 | q13.2 | C20orf17 | 0.09 | |
| Chr20: 53,727,067-54,179,752 | q13.31 | CBLN4 | 0.10 | |
| Chr20: 59,642,719-60,188,470 | q13.33 | TAF4 | 0.14 | |
| Chr20: 60,787,319-62,306,895 | q13.33 | Various | 0.14 | mir-124a-3 |
| Chr21: 44,323,591-46,865,905 | q22.3 | Various | 0.06 | |
| Deletions | | | | |
| Chr1: 13,706,706-14,067,130 | p36.21 | PRDM2 | 0.09 | |
| Chr1: 117,882,599-118,416,501 | p12 | WDR3 | 0.06 | |
| Chr1: 145,686,817-146,572,267 | q21.1 | Various | 0.17 | |
| Chr3: 63,833,723-69,246,170 | p14.1 | Various | 0.02 | |
| Chr3: 112,531,083-113,299,667 | q13.3 | Various | 0.07 | |
| Chr4: 4,307-2,356,621 | p16.3 | Various | 0.07 | |
| Chr5: 105,121,999-105,651,166 | q21.3 | None | 0.07 | |
| Chr6: 108,995,171-109,511,112 | q21 | FOXO3A | 0.08 | |
| Chr7: 153,286-2,760,544 | p22.3 | Various | 0.08 | |
| Chr8: 6,644,897-7,789,182 | p23.1 | Various | 0.07 | |
| Chr9: 21,534,743-22,602,390 | p21.3 | CDKN2A | 0.07 | |
| Chr11: 56,865,377-57,532,499 | q12.1 | CTNND1 | 0.08 | mir-130a |
| Chr11: 71,383,633-71,895,665 | q13.5 | Various | 0.07 | |
| Chr11: 84,354,772-84,783,036 | q14.1 | Unknown | 0.07 | |
| Chr11: 117,818,491-119,647,340 | q23.3 | Various | 0.05 | |
| Chr12: 129,600,721-132,216,957 | q24.33 | Various | 0.04 | |

TABLE 3-continued

Loci that undergo frequent amplification or deletion
among members of the Swedish diploid tumor set.

| Chromosome position | Band | Gene symbol | Index | miRNA |
|---|---|---|---|---|
| Chr13: 31,797,266-33,180,891 | q13.1 | BRCA2 | 0.04 | |
| Chr13: 87,304,169-88,578,303 | q31.2 | None | 0.04 | |
| Chr14: 18,212,915-19,603,016 | q11.1 | ACTBL1 | 0.07 | |
| Chr14: 93,367,136-94,452,890 | q32.13 | Various | 0.05 | |
| Chr15: 89,220,113-89,661,514 | q26.1 | Various | 0.06 | |
| Chr15: 99,340,489-100,206,128 | q26.3 | Various | 0.05 | |
| Chr16: 59,364,195-60,612,397 | q21 | CDH8 | 0.07 | |
| Chr17: 6,584,338-9,759,236 | p13.1 | TP53 | 0.04 | mir-195, 497, 324 |
| Chr17: 11,490,353-12,494,377 | p12 | MAP2K4 | 0.06 | |
| Chr17: 14,864,271-16,460,839 | p12 | Various | 0.06 | |
| Chr17: 56,600,423-57,012,081 | q23.2 | TBX2/TBX4 | 0.08 | |
| Chr17: 76,951,018-78,569,870 | q25.3 | Various | 0.10 | |
| Chr18: 20,839,509-21,648,403 | p11.2 | Unknown | 0.04 | |
| Chr19: 226,336-4,793,685 | p13.3 | Various | 0.08 | mir-7-3 |
| Chr20: 14,024,068-15,010,799 | q12.1 | FLRT3 | 0.04 | |
| Chr22: 14,858,033-20,363,383 | q11.1 | Various | 0.05 | mir-185, 130b |
| Chr22: 25,251,830-27,941,420 | q12.1 | CHEK2 | 0.05 | |
| Chr22: 31,255,407-32,147,191 | q12.3 | TIMP3 | 0.05 | |
| Chr22: 41,881,035-42,584,718 | q13.2 | SCUBE1 | 0.11 | |

The Index represents a relative measure that combines frequency and the inverse width of the amplicon or deletion ("Materials and Methods"). Loci in the table were selected to have an index of 0.05 or greater.

EXAMPLE 8

Rearrangements in Grade I Tumors

Tumors in which the cells maintain their differentiation as shown by histological examination are generally considered to be less aggressive and to have a good prognosis irrespective of migration to the lymph nodes. Ten examples of these so-called Grade I tumors were available from the Swedish samples and thirteen from the Norwegian collection, including eight in which one or more nodes were affected. A single non-invasive DCIS (ductal carcinoma in situ) sample (MicMa245) was also present in the Norwegian set. All of the Swedish samples were medium to large tumors between 20 and 30 mm in size while the Norwegian samples ranged from 0.5-25 mm.

Although the number of samples is small, the similarity in ROMA profiles among the thirteen representative samples depicted in FIG. 36 is dramatic and may provide insight into some of the earliest events leading to invasive breast cancer. Four of the twenty-three Grade I samples yielded no detectable events (not shown). Eighteen of the nineteen tumors with any detectable events showed a characteristic rearrangement in chromosome 16 in which one copy of 16q appears to be deleted (assuming diploidy) and 16p is concomitantly duplicated. This rearrangement was also present in the DCIS sample (MicMa245 in FIG. 36, panel B). The rearrangement of 16 is often coupled with either a converse rearrangement of the arms of chromosome 8 (8p deleted and 8q duplicated) or a duplication of the q arm of chromosome 1. All three of these events are seen in more highly rearranged breast cancer genomes such as those in FIG. 3A, right panel, and in fact are among the most common events by frequency in all samples (see FIG. 2A, panel B).

Grade I tumors generally display relatively few genomic events but rarely show more complex patterns of advanced simplex tumors (see MicMa171 in FIG. 36, panel B) indicating that despite a strong correspondence, there is not a strict relation between genomic state and histological grade. MicMa171 has progressed to the point of achieving the common amplicons at 8p12 (Garcia, et al, 2005) and 17q11.2, both of which are noted in Table 3. The sole Grade I tumor not showing rearrangement of 16p/q (WZ43 in FIG. 36, panel B) exhibits a different pattern with rearrangements of chromosome 20q and deletion of 22q indicating that the 16p/q rearrangement is not the only pathway to tumorogenesis. Although certain of these rearrangements contain obvious candidate driver genes such as the duplication of MYC on 8q24 or the loss of the cadherin (CDH) complex on 16q, the actual target genes remain the target of further study.

EXAMPLE 9

Relation of Patterns to Clinical Outcome

On first inspection, the highly rearranged "sawtooth" and "firestorm" patterns appeared to correlate with shorter survival in the diploid tumors, presumably due to selection of novel genetic combinations afforded the cancer cells by the opportunity for accelerated recombination. This observation was confirmed by rigorous mathematical and statistical analysis. Using the total number of segments, or events, as a measure does not clearly distinguish a sample with a single firestorm from the simplex pattern with a similar number of events, but the effects of the firestorm are much more deleterious to survival. A mathematical measure was chosen that would separate the sawtooth and firestorm patterns from the flat and simplex patterns by scoring the close-packed spacing of the firestorm events, while at the same time incorporating the total number of events. The sum of the reciprocals of the mean of lengths of all adjacent segment pairs accomplishes this goal:

$$F = \sum_i \frac{2}{l_i^L + l_i^R} \quad (1)$$

where i enumerates all the discontinuities with a magnitude above a numerical threshold of 0.1 in the segmented profile, and where 0 denotes the number of probes in the closest neighboring discontinuity on the right (left), or to a chromosome boundary, whichever is $_R$lul closer. This is called the "inverse adjacent segment length measure." This calculation is performed after masking for CNPs, and does not include the X- or Y-chromosome. The measure works equally well if absolute position in the genome is substituted for probe number. Using this algorithm the sawtooth patterns achieve a high F because of the sheer number of distributed events, while the firestorm patterns achieve high F values even if only a single arm is affected because of the contribution of proximity (see WZ11 in FIG. 3A, right panel).

F is a robust measure separating the diploid cancers into two populations that have different survival rates. F ranges in value from zero to a maximum of about 0.86 for the Swedish diploid group. For a range of values of F, from 0.08 to 0.1 both a significant and strong association was found between the discriminant value and survival beyond 7 years. The optimum value for F separating by survival does not change appreciably when calculated for survival at ten years. As shown in Table 4, 0.08 and 0.09 yield the lowest p-values ($2.8 \times 10^{-7}$ and $5.9 \times 10^{-7}$ by Fisher's exact test) with 0.09 showing the strongest association with the long-lived versus the short-lived cancer patients, with a an odds ratio of 0.07. Analysis was performed using the 'fisher test' function in the R data analysis software which computes an estimate of the odds ratio for a 2×2 contingency table using the conditional maximum likelihood estimate. By contrast, the divider based solely on the number of events without regard to size or proximity has a lower significance, with a p-value of $4.2 \times 10^{-4}$.

Figures 37A, 37B:
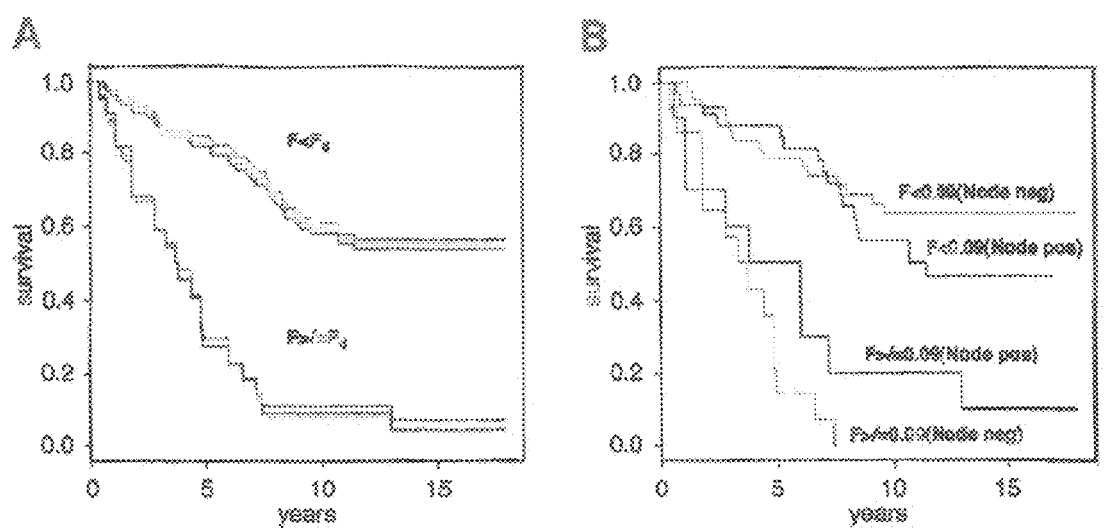
FIGS. 37A and 37B show the Kaplan-Meier plots of the Swedish diploid subset grouped according to Firestorm index (F).

A strong association between F and survival is also found using an alternative statistical procedure that makes no explicit reference either to a particular discriminant value of F or to a particular survival time threshold: the Swedish diploid set was divided into quartiles with respect to F, then a log-rank test was applied for differences in survival in these four groups. The four groups are found to have different survival properties, with a p-value of $10^{-7}$. In FIGS. 37A and 37B, the Kaplan-Meier plots of survival for all Swedish diploids were displayed, with a range of discriminant values for F from 0.08 to 0.1. These plots show dramatically different rates of survival for tumors above or below the F-discriminant ($F_d$). The discriminatory power of F with respect to survival is even more dramatic when node positive and node negative cases are plotted separately as in FIG. 36, panel B, using F=0.09.

Although association between F and survival was found, no significant association between F and either tumor size, lymph node status, grade, expression of the estrogen (ER) and progesterone (PR) receptors was identified (see Table 4, also "Materials and Methods"). In other words, F is an independent clinical parameter. This result does not imply that these other parameters do not predict disease recurrence, or that in a random accrual that F would not associate with them. Rather, it reflects that our two groups of diploids, short-term and long-term survivors, were picked to be balanced for lymph node status, tumor size, and so forth, and that F has predictive value independent of these traditional clinical measures. A significant association was found between F on one hand and age at diagnosis, and amplifications of the CCND1, MYC and ERBB2 loci on the other hand. However, as shown in the following, F retains its predictive value for survival after adjustment for the effects of these four factors.

TABLE 4

Association of clinical parameters with the F measure in the Swedish diploid subset.

| $F_d$ value | Clinical parameter | Discriminating principle | p-value from Fisher's exact test | Odds ratio |
|---|---|---|---|---|
| 0.08 | Survival | Above or below 7 yr | $2.8 \times 10^{-7}$ | 0.073 |
| 0.09 | Survival | Above or below 7 yr | $5.9 \times 10^{-7}$ | 0.070 |
| 0.1 | Survival | Above or below 7 yr | $8.2 \times 10^{-6}$ | 0.073 |
| 0.09 | Grade | 2 vs 3 | 0.39 | 0.58 |
| 0.09 | Node condition | Negative or positive | 1.0 | 0.96 |
| 0.09 | Size | Smaller or larger than 29 mm | 0.40 (0.38 for 29) | 0.62 (0.62 for 29) |
| 0.09 | ER status | Above or below 0.05 fg/µg prot. | 0.73 | 0.77 |
| 0.09 | PR status | Above or below 0.05 fg/µg prot. | 0.75 | 0.70 |
| 0.09 | HER2 amplification | Above or below segment threshold | 0.0010 | 0.12 |
| 0.09 | CCND1 amplification | Above or below segment threshold | $8.3 \times 10^{-4}$ | 0.11 |
| 0.09 | MYC amplification | Above or below segment threshold | 0.0020 | 0.20 |
| 0.09 | Age at diagnosis | Above or below 57 years | 0.0066 | 0.26 |
| 0.09 | Adjuvant therapy | −/+ | 0.44 | 0.64 |
| 0.09 | Radiation therapy | −/+ | 1.0 | 1.1 |

To further study the effect of F on survival the data was fit to a Cox proportional hazards model, starting with a 63-case subset of the Swedish diploid data set for which we have complete information on all the clinical parameters listed in Table 4. A clinical parameter is considered significant for survival if the corresponding p-value is below 0.05. As shown in Table 5, several rounds of analysis were performed, each time removing from consideration clinical parameters not found significant in the previous round. This reduction in the number of parameters in turn allows us to increase the data set for which the information on the remaining parameters is complete. As a result, F and the age at diagnosis were found to be the only covariates that remain statistically significant through all the rounds of analysis. A fit to the entire Swedish diploid data set gives 4.4 as a hazard ratio for F, adjusted for the age at diagnosis.

Table 5. Multivariate analysis of clinical parameters shown in Table 3. Discriminating values for AD and size were chosen to maximize their association with survival. Abbreviations: HR=Hazard Ratio; CI=95% confidence interval for HR.

TABLE 5

Multivariate analysis of clinical parameters shown in Table 3

| Clinical parameter | Discriminating principle | (P) | HR | CI | (P) | HR | CI | (P) | HR | CI | (P) | HR | CI |
|---|---|---|---|---|---|---|---|---|---|---|---|---|---|
| F | Above or below 0.09 | $5 \times 10^{-6}$ | 9.5 | 3.6:25.0 | $2 \times 10^{-6}$ | 8.4 | 3.5:20.3 | 6e−5 | 5.3 | 2.4:12.1 | 9e−7 | 4.4 | 2.4:7.8 |
| AD | Above or below 57 yr | $6 \times 10^{-3}$ | 3.0 | 1.4:6.7 | 0.02 | 2.3 | 1.2:4.5 | 0.04 | 2.3 | 1.1:5.0 | 7e−3 | 2.2 | 1.2:3.8 |
| MYC amp. | Above or below segment threshold | 0.02 | 0.26 | 0.08−0.8 | NS | | | | | | | | |

TABLE 5-continued

Multivariate analysis of clinical parameters shown in Table 3

| Clinical parameter | Discriminating principle | (P) | HR | CI | (P) | HR | CI | (P) | HR | CI | (P) | HR | CI |
|---|---|---|---|---|---|---|---|---|---|---|---|---|---|
| ER status | +/− | NS | | | | | | | | | | | |
| PR status | +/− | NS | | | | | | | | | | | |
| Size | Above or below 29 mm | NS | | | | | | | | | | | |
| Node condition | +/− | NS | | | | | | | | | | | |
| Grade | I, II, or III | NS | | | | | | | | | | | |
| ERBB2 amp. | Above or below segment threshold | NS | | | | | | | | | | | |
| CCND1 amp. | Above or below segment threshold | NS | | | | | | | | | | | |

Discriminating values for AD and size were chosen to maximize their association with survival.
(HR) Hazard Ratio;
(CI) 95% confidence interval for HR;
(NS) not significant.
Columns 3 through 5: all the clinical parameters listed were used in the fit;
columns 6 through 8: F, AD and MYC amp. were used in the fit;
columns 9 through 14: F and AD were used in the fit.
Results in columns 3 through 11 are based on a 63-case subset of the Swedish diploid set for which all the clinical parameters used were available.
Results in columns 12 through 14 are based on the entire Swedish diploid set.

EXAMPLE 10

The "Firestorm Index"

The high resolution of the ROMA technique along with our segmentation algorithm has enable us to visualize narrow and closely spaced chromosomal rearrangements, in particular those that make up the complex "firestorm" patterns. The validity of the amplicon assignments, and hence of the Kalmogorov-Smirnov methodology, has been validated by FISH in all cases tested. Coupled with the long term survival and ploidy data available for the Swedish dataset we derived a working hypothesis consistent with previously reported work (Al-Kuraya, et al 2004, (Loo et al., 2004) that complexity of rearrangement is a negative prognostic factor, but with the novel addition that the closely spaced events in firestorms make a disproportionally large contribution to that prognosis.

Therefore, a molecular signature, F, has been derived that correlates with survival in a subset of tumors, namely pseudo-diploid tumors of patients from Scandinavia. The signature is a simply defined mathematical measure that incorporates two features of the genome copy number profile, namely the number of distinguishable amplification and deletion segments, and the close packing of these segments. It is easy to imagine that the number of distinguishable events can serve as a marker for malignant "progression." A large number of events might reflect either an unstable genome, a cancer that has been growing for a longer time within the patient and hence has had more opportunity to metastasize, or a cancer that has undergone more selective events than cancers with fewer "scars" in its genomes. It is worth noting that even a single case of the clustered amplifications ("firestorms") appears to be a prognostic indicator of poor outcome.

The analyses of this selected sample set described herein indicate that prognoses in primary breast cancer, measured by the probability of overall survival, are correlated with the morphology of the gene copy number signature. Within the balanced group of our samples, the magnitude of the signature is independent of such established clinical markers as node status, histologic grade and primary tumor size. Hence it is reasonable to expect that the signature will contribute to the prediction of outcome, perhaps—as suggested by our data— in combination with other known factors. A clear potential application of such a measure is in the determination of prognosis, with a focus on the identification of patients with such excellent prognoses that systemic therapy is not required or, conversely, such poor prognoses—in spite of clinical measurements that might be misleading in this regard—that systemic treatment is absolutely indicated. For example, a patient with a small, estrogen-receptor positive, node-negative primary breast cancer—all factors that usually indicate a good prognosis—might have an especially poor prognosis as predicted by our method. Further work with unselected sample sets will, of course, be required to extend these findings beyond the working hypothesis stage.

EXAMPLE 11

Event Mapping

Further gains in outcome prediction are expected by utilizing knowledge of which individual loci are amplified or deleted in a specific cancer. Indeed, there are clearly loci, such as 1q, 8p and 8q, 16p and 16q and 22q that are present in both outcome groups with almost equal frequency, and others, such as 1p12-13, 11q12 and 11q13, 9p, 10q, 17q and 20q that are present predominantly in the cancers from patients with poor outcomes. The separation of the two groups in the dataset herein can be improved by adding rules that proscribe amplification or deletion at specific loci or combinations of loci. However, despite exhaustive attempts, additional improvement in outcome prediction based on knowledge of specific loci might not be more than one would expect by chance, given overall event frequencies. The literature does contain many reports that specific amplifications or deletions correlate with poor prognosis (Al Kuraya et al., 2004; Knoop et al., 2005; Chunder et al., 2004; Berns et al., 1995; Madjd et al., 2005; Jarvinen and Liu, 2003). While these reports may indeed be correct, they may also be a consequence of the larger picture, namely that there are more lesions in "progressed" cancers. The copy numbers of specific genes may also be useful in clinical decision-making, following the clear demonstration that ERBB2 (used interchangeably with HER-2 herein) amplification—now determined by FISH— conveys both prognostic and therapeutic information. For example, patients with amplified ERBB2, as determined by FISH, are now treated with Herceptin®. This determination can be made as well by ROMA or other methods for genome profiling, and such profiling may be more informative about which patients have amplifications and which benefit from such treatment. Other events in the genome can also indicate different choices of therapy. For example, two of the patients in the present study exhibit amplification at the EGFR locus rather than ERBB2 and such patients might benefit from treatment with drugs targeted to that oncogene such as Tarceva™. There are other such examples in the data set. More data than we now have will be needed to fully test a better outcome predictor model based on specific loci.

EXAMPLE 12

Scandinavian Tumor Sets

In the course of this study, and to gain a perspective, ROMA profiles were compared between two independent sets of tumors from Sweden and Norway, which showed a basic similarity in the profiles independent of source or collection method. It is noteworthy that the diploid tumors with poor outcome show a very similar overall profile to the aneuploid tumors. Thus, whether or not the two classes of tumors, diploid and aneuploid, have different mechanisms for malignant genome evolution, a subset of loci recurred in amplifications and deletions in both types.

It is perhaps not surprising that the tumors from Swedish and Norwegian populations selected for this study have very similar frequency profiles, given the ethnic and environmental homogeneity in Scandinavia. These populations may also show similarity to other breast tumor sample sets. In any event, the ability to profile cancers from populations of restricted ethnicity and environment adds a new tool for those who wish to study the effects of genetics and environment on cancer. It will be of great interest to assess genome profiles of other geographically-defined groups, with particular attention to the possibility of inherited patterns of disease susceptibility or gene-environment interactions.

EXAMPLE 13

Future Breast Cancer Studies

The studies described herein focused on a restricted question, the relationship between complex genomic rearrangements and tumor progression as determined by eventual outcome in breast cancer. The related question of genomic and molecular markers for survival among aneuploid cancers has not been examined. It is evident from even superficial inspection that many recurrent events encompass known oncogenes (such as ERBB2, CCND1, MYC) and tumor suppressors (such as CDKN2A and TP53), but many do not, such as a commonly amplified and very narrow region at 8p12, for which the driver gene has not been definitively identified (marked with a probe for BAG4 in FIG. 3A) (Garcia et al., 2005). Whether certain lesions show covariance is being analyzed. Using the techniques and methods of the present invention, it is expected that such genomic and molecular markers for survival among aneuploid cancers will also be elucidated.

Finally, it is becoming clear through the identification of gene copy number alterations in tumors in numerous CGH studies that there is likely to be a genetic pathway, albeit a complex one, at work in the evolution of tumors. As the collection of tumor genomic profiles increases and can be compared with treatment regimes as well as patient outcome, that prognostic information regarding clinical outcome is expected to become apparent. Thus existence of some systematic organization to the genomic events in these tumors raises the intriguing possibility that allows the dissection of the pathways that determine the bridge from non-invasive to invasive to metastatic cancer.

EXAMPLE 14

Comparison of Aneuploid and Diploid Tumors

As described herein, ROMA provides a high-resolution genome-wide survey of the events in a given tumor but it does not yield a direct copy number value in a given cell. Once events are identified by ROMA specific FISH probes can be constructed where desired and used to provide an accurate cell by cell copy number and in many cases, to assess the structure of the chromosome event. Interphase FISH on ten diploid and 10 aneuploid tumors from Groups 1 and 3a (Table 1B above) was performed.

The PROBER algorithm ("Materials and Methods") was used to produce PCR based probes for a series of specific deletions and duplications identified by ROMA. BAC probes were also used to quantify the copy numbers of a set of known oncogenes frequently amplified in breast tumors. Two sets of FISH experiments were performed. The first set used ten probes for known or suspected oncogenes that had some history of amplification in the literature. Typical results are shown in Table 6. In each case, the average of at least 30 cells was taken for determining the FISH copy number. It is clear that the ROMA segmentation value does not correspond exactly with the copy number as measured by FISH, but it is also clear that amplicons identified by FISH show up as strong peaks in ROMA profiles.

TABLE 6

| Probe/Gene | Loc. | Tumor Sample | ROMA segment | ROMA normalized | FISH | FISH/ genome | Interp. |
|---|---|---|---|---|---|---|---|
| c-Myc | 8q24 | WZ11 | 1.85 | | 15 | 7.5 | clustered |
| c-Myc | | WZ16 | 1.8 | | 5 | 2.5 | |
| CKS1B | 8q22 | WZ11 | 2.1 | | 15 | 7.5 | clustered |
| CCND | 11q13 | WZ12 | 1.64 | | 7 | 3.5 | clustered |
| CCND | | WZ17 | 1.68 | | 9 | 4.5 | clustered |
| CDND | | WZ18 | 1.85 | | 9 | 4.5 | clustered |
| ERBB2 | 17q12 | WZ20 | 1.9 | | 15 | 7.5 | clustered |
| MDMX | 1q32 | WZ18 | 1.2 | | 4 | 2.0 | |

The second set of FISH experiments was done in reverse, where probes were made from regions identified by ROMA, especially those experiencing less dramatic copy number changes than the large amplicons reported in Table 6. Examples of both of these sets of experiments are shown graphically in FIG. 4. WZ1 is an aneuploid tumor sample that includes multiple elements demonstrating the utility of ROMA and validation of subtle ROMA features by FISH. In the top panel, a segmentation profile of WZ1 shows multiple amplifications as well as whole deletions and duplications, and finally smaller segmental deletions and duplications. The FISH results for the oncogenes tested in the first set of experiments described above are shown by locus in the top panel. These include several amplicons and at least one whole arm duplication at 1q. The three small panels below are an example of the probes made specifically for this tumor using the PROBER software ("Materials and Methods") to regions that had undergone less obvious events. The image shows a two-color FISH result for probes made to the two regions of deletion and duplication identified in the flanking panels. The result clearly shows that this tumor, with a genomic equivalent of 3c has lost at least two copies of the chromosome 2 locus and gained one copy of the chromosome 20 locus.

ROMA was run using 85K BglII Version 4 chip design manufactured to our specifications by Nimblegen, Inc. which displays 82,972 separate features each consisting of single stranded DNA, 60 bases in length. After hybridization, the basic dataset consists of ratios calculated by taking the geometric mean of normalized hybridization data from two separate color-reversed chips, each comparing a tumor sample to the laboratory standard male fibroblast cell line. This geometric mean of ratios is displayed on the Y axis and the points are arranged in genome order according to chromosome and chromosome position. The general format of the data output is shown in FIG. 1.

Panel A of FIG. 1 depicts the standard ROMA profile for a normal female compared to a normal male. This is the arrangement used all of the breast cancer samples presented in this study. The figure shows the feature by feature variation, known as the geomean ratio, in gray. This "raw:geomean ratio data must be further refined in order to reliably identify specific amplifications, duplications and deletions and determine their amplitudes and, most importantly determine their boundaries. This refinement is achieved through a series of statistical methods that comprise the Bridge 5 segmentation algorithm, described in Materials and Methods. Segmentation is central to the intelligent use of the array data as it parses the data and defines intervals of "genomic events" which makes them more perceivable to the human eye. It insures a consistent and reliable interpretation of data by associating each data feature with a likelihood measure that the feature is not the result of the chance clustering of random noise in probe ratios. In FIG. 1, panel A, the geomean ratio data is overlayed with the results of the segmentation algorithm in red. The expected ratio differences for the X and Y chromosomes for female versus male DNA are clearly visible, while the rest of the genome is centered a ratio of 1.0. Even in these normal genomes, differences are visible. These copy number polymorphisms have been described previously (Sebat et al., 2004) and are particularly useful in ROMA studies as markers for heterozygosity and for experimental quality control.

For convenience in data graphing, the events identified by Bridge 5 were arbitrarily segregated into two categories: "Broads" are events spanning 6 sequential probes or more and include all of the major chromosome rearrangements. "Fines" make up events spanning 2-6 probes and most likely result from intrachromosomal deletions and amplifications. The results of segmentation for a single tumor sample ("Broad Means") are superimposed on the geomean ratio data for that tumor in FIG. 4.

Figure 5:
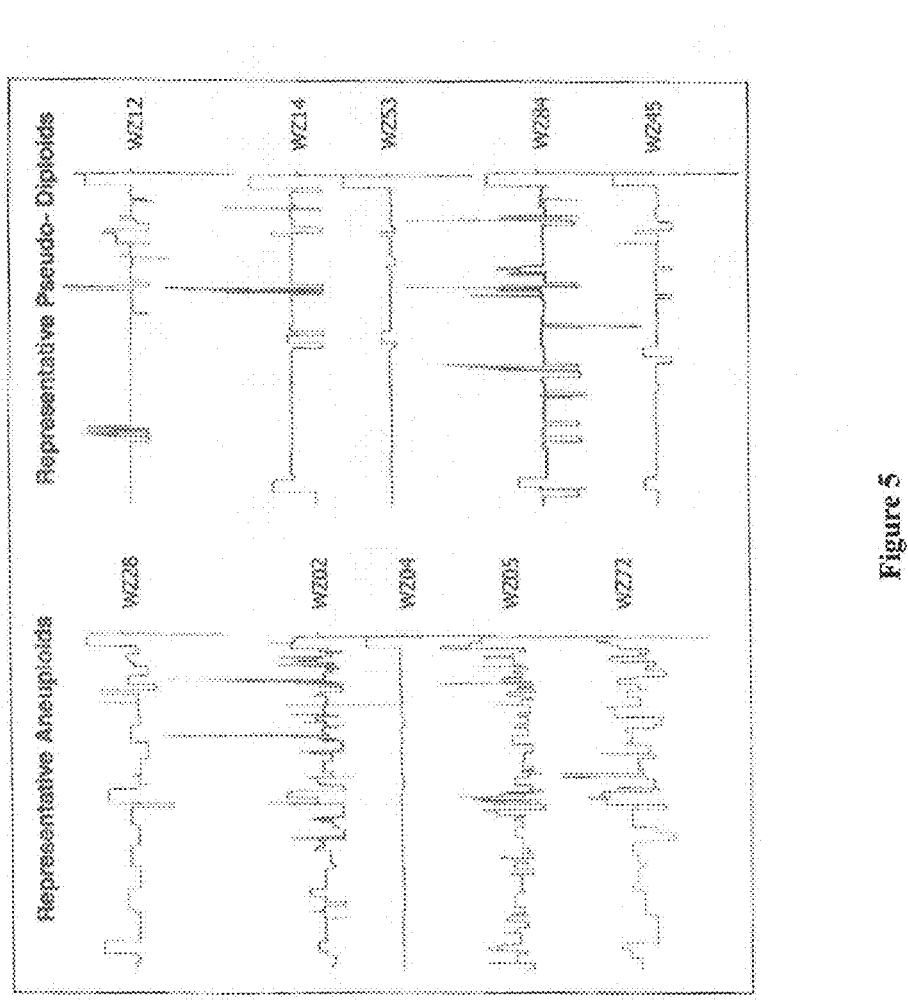
FIG. 5 shows examples of aneuploid and pseudo-diploid tumors described in the text. Note that aneuploid tumors in general exhibit an overall greater frequency of chromosome rearrangements than do pseudo-diploid tumors.

FIG. 5 display the segmentation profile for representative aneuploid and pseudo-diploid tumor samples. Several features are obvious from a visual inspection of the graphical data in these figures. First, it clear that there are at least two major classes of events, large segmental deletions and duplications of one or two copies of chromosome arms and narrow, high copy number amplifications, both of which have been observed previously by other methods. The advantage for ROMA over techniques used in previous studies in analyzing these events is in the resolution provided by the large number of features on the ROMA chip. Of the 101 tumor samples profiled by ROMA, only three samples failed to exhibit significant genome copy number alterations. Two of these were from Group 4a containing Grade I and II tumors that as a group show fewer detectable alterations. The third, WZ4, is a rare aneuploid, Grade III tumor and be an example of the rare exception where the genetic events underlying the cancer are not reflected in copy number alterations. The alternative explanation, that there were relatively few tumor cells in the sample from which the DNA was made is always a possibility, but in this case FISH results, described below, indicate that the most of the cells from this sample are, in fact, aneuploid.

Finally, the Broad Mean value for the X chromosome in a typical diploid female/diploid male experiment ranges from 1.3 to 1.5. A theoretical peak Broad Mean value was established for the X chromosome that is 1.65. This is significantly higher than values reported for an expected 2:1 ratio in non-representational microarray CGH methods, but still less than the expected value of 2. This ratio, which averages about 1.45 sets a rough benchmark for other events, particularly duplications or deletions of chromosome arms or segments. Most other broad events, particularly in diploids show amplitudes less than that of the X as would be expected since all tumor samples contain a certain fraction of normal cells and also because not all chromosomal events would have occurred at the same time in the development of the tumor and therefore will have a characteristic fractional representation in the ROMA profile. Using FISH to confirm copy numbers we have determined that while ROMA values underestimate copy number, they are very sensitive to the existence of events and can accurately detect events with a deviation from the baseline segmentation as little as 0.02.

Due to the huge amount of data accumulated in CGH experiments, it is usually necessary to process multiple experiments together and to analyze the aggregate by statistical methods. The drawback of such methods is that they obscure the potential for identifying unique patterns and phenotypes among individual tumors. FIG. 5 therefore illustrates a representative set of ROMA profiles for tumors to demonstrate the variety of forms that samples in this study can take. Some of these profiles are also specifically referenced in later sections of the text.

Since the reference genome used in this study is from a male fibroblast cell line, breast cancer genomes analyzed in this study appear to have "lost" the Y chromosome and "duplicated" the X. These artifacts actually provide reference points as duplication and homozygous loss for estimation of copy number of other loci in genome. One important point to note is that this has limitations due to the fact that ROMA measures average of copy number of cells in tumors and that some tumor cells have lost one of their X chromosomes. Furthermore, the presence of a variable number of normal cells in any tumor cells complicates the estimates of copy number based purely on ROMA.

In addition, it is clear that diploids, in general, exhibit fewer events, with exception of isolated amplifications, than aneuploids. This observation has been made before and it is logical to assume that aneuploids, having multiple copies of most chromosomes, have more degrees of freedom to gain or lose copies without deleterious effects on proliferation that might be caused by wholesale gene imbalances as would be the case in diploids. Yet, on a case by case basis, diploid tumors can exhibit the same pathogenic potential for proliferation and for local and distant metastasis as aneuploids. This combination of fewer overall events coupled with the frequent narrow, high copy number amplicons makes it particularly advantageous to focus on diploid tumors for CGH analysis in general, and ROMA in particular. For most users, CGH will point to certain loci, which must then be subject to more detailed molecular studies. The lower frequency of observable events in diploids reduces background "chatter" and reduces the number of events and loci that must be considered. Conversely, the apparent restriction on gain or loss in diploids leads to the generation of smaller, more discrete events, particularly amplifications, that can point directly to oncogenes. The insights gained from the increased resolution of ROMA combined with FISH for both of these aspects of CGH are described below.

EXAMPLE 15

Analysis of a Chromosome Arm by FISH and the Respective Probes

The prediction that the amplification events were taking place on a chromosome arm was tested by a series of FISH experiments. In addition to the BAC probes for c-MYC and CKS1B already available, BACs from each narrow amplicon and each of the "spacer" regions in between were identified. Two-color FISH experiments were performed on cell prints made from a section of tumor sample WZ11. The results of the FISH experiments (Table 1B) showed perfect correspondence with the ROMA profile shown in FIG. 6A, panel B. Probes from each amplicon yielded 8-15 spots in the FISH exposures while probes for the intervening regions showed only the two spots expected for a diploid genome. Moreover, as shown previously for the aneuploid amplicons in WZ1 the spots corresponding to amplicons were clustered, suggesting that they a co-localized on a single chromosome arm rather than being distributed throughout the genome as is the case for supernumerary or double minute chromosomes that are sometimes observed in cell culture. More notable, however, was the observation that when cells were exposed to probes from two different amplified peaks from the same firestorm in a two color FISH experiment, the resulting sets of spots were co-localized in a single cluster. FIG. 6A, panel B shows two examples using one pair of probes corresponding to c-myc and CKS1 and another pair carrying FGFR1 on the p arm of chromosome 8 and an unknown locus AK096200 (on the 8q arm). These results suggest that at least for the firestorm in WZ11, all of the amplified DNA regions are being carried on the same region of a single chromosome as would be expected if the chromosome had entered into a Breakage-Fusion-Bridge (BFB) or Break Induced Replication (BIR) models that have been invoked to explain chromosome instability in cancer cell lines.

TABLE 7

BAC PROBES FOR CHROMOSOME 8 OF WZ11

| | BAC | Band | Chrom Pos Start | Chrom Pos End | Representative Gene | ROMA | FISH |
|---|---|---|---|---|---|---|---|
| RP11 | 138G3 | 8p21.3 | 22180711 | 22331959 | DBC1 | − | 2N − 1 |
| | 90P5 | 8p12 | 37712838 | 37848200 | BAG1 | | AMP |
| | 357D8 | 8p12 | 37967861 | 38129590 | FGFR1 | | AMP |
| | 805C22 | 8q11.21 | 48978882 | 49165556 | AK096200 | | AMP |
| | 478E11 | 8q11.21 | 49778799 | 49948501 | SPACE | | 2N |
| | 259F14 | 8q11.23 | 52731303 | 52924831 | STK18 | + | 4N+ |
| | 799C18 | 8q12.1 | 56469902 | 56653271 | V-YES (LYN) | − | 4N+ |
| | 706D13 | 8q12.1 | 60372548 | 60557407 | SPACE | | 2N |
| | 692N8 | 8q13.1 | 67069873 | 67257589 | MYBL1 | − | AMP |
| | RP11-55P7 | 8q21.11 | 75121470 | 75228411 | SPACE | | 2N |
| | 639F19 | 8Q21.13 | 80679488 | 80836846 | TPD52 | + | AMP |
| Gene | | | | | CKS1A | | AMP |
| Seq. | 115L19 | 8q21.3 | 90543288 | 90700141 | NBS1 | + | 2N |
| PCR | 347C18 | 8Q22.1 | 95516238 | 95681155 | CCNE | | AMP |
| | 465K6 | 8Q22.2 | 99124277 | 99293287 | STK3 | − | 4N |
| | 352F19 | 8q22.3 | 101553889 | 101756635 | YWHAZ | + | 2N + 1 |
| | 307H2 | 8q24.11 | 117473502 | 117646608 | RAD21 | + | 4N |
| | 775B15 | 8q24.12 | 120005605 | 120163931 | NOV | − | 2N + 1 |
| Gene | | 8q24.1 | | | MYC | | AMP |
| Seq. PCR | 644H23 | 8q24.3 | 140245802 | 140419024 | KCNK9 | + | 2N − 1 |

The localization of the amplicons was also tested from two different multiply amplified chromosome arms occurring in the same tumor sample. A chromosome localization model would predict that the spots from amplicons on different chromosomes would cluster separately from each other. This is what was observed in two color FISH experiments using probes for erbB2 on 17p and cyclin D1 on 11q in three tumor samples where both genes had been previously shown to be amplified by both FISH and ROMA. An example of this result is shown in FIG. 6c using cells from sample WZ20 where earlier FISH experiments had shown erbB2 to be present in >>15 copies per cell and cyclin D1 to be present in 6 copies per cell. Two separate clusters are clearly visible, one containing only the red spots corresponding to cyclin D1 and the large cluster of green spots corresponding to erbB2/Her2.

EXAMPLE 16

Other Disease Models

Figure 28:
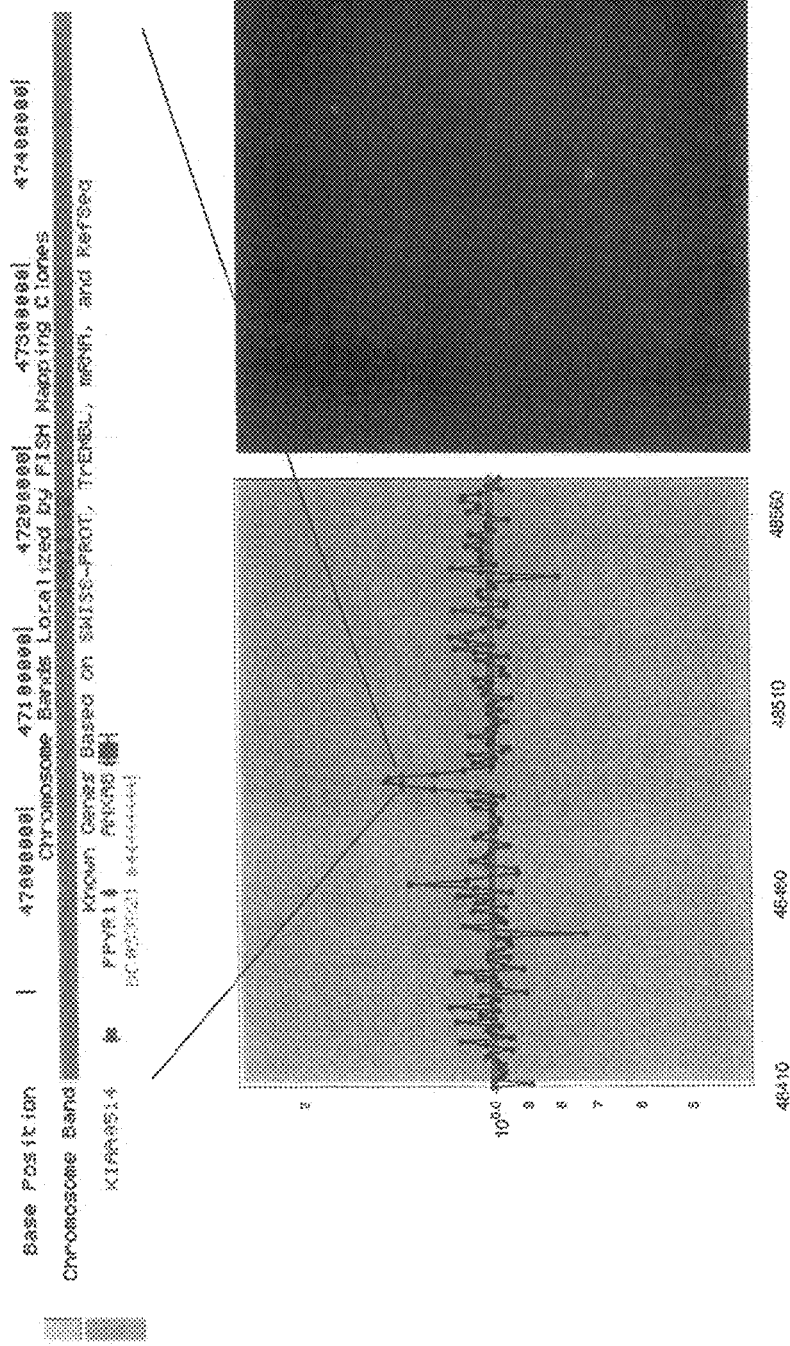
FIG. 28 shows a ROMA-generated genomic profile illustrating amplification of a chromosomal region, as indicated; and the results of a corresponding FISH experiment. As shown in the left panel of FIG. 28, the region corresponding to loci PPYR1 and ANXA8 was amplified in this sample. The amplification detected by ROMA was confirmed by designing a probe corresponding to the amplified region and FISH using that probe. (See the three dots in the FISH image).
Figure 29:
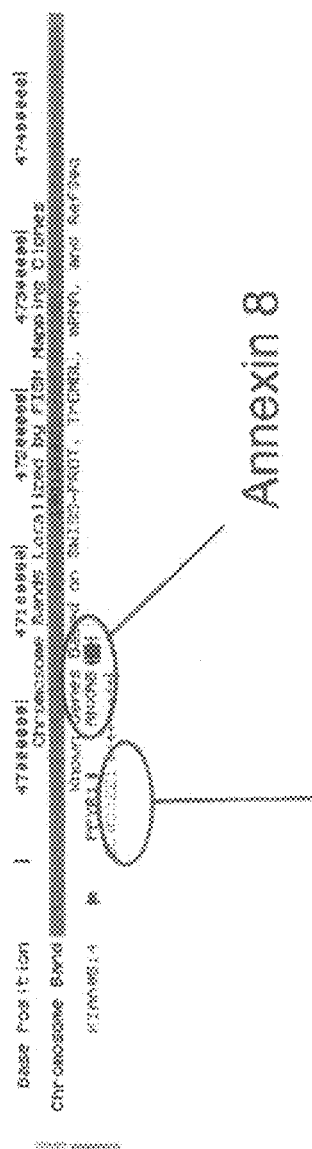
FIG. 29 shows various genetic loci present in the chromosomal region in FIG. 28.

FIGS. 28 and 29 show loci in the chromosome band 10q11.22. As shown in the left panel of FIG. 28, the region corresponding to loci PPYR1 and ANXA8 was amplified in this sample. The amplification detected by ROMA was confirmed by designing a probe corresponding to the amplified region and FISH using that probe. (See the three dots in the FISH image). ANXA8 is selectively over-expressed in acute myelocytic leukemia Chang et al. (1992) Specific expression of the annexin VIII gene in acute promyelocytic leukemia. *Blood* 79: 1802-1810. PPYR1 (also termed Y4 in the literature) appears to be involved in the regulation of appetite and body weight. Sainsbury et al. reported that Y4-null mice showed aggressive behavior. The Null animals also showed reduced body weight and increased plasma pancreatic polypeptide levels. See Sainsbury et al. (2002) Y4 receptor knockout rescues fertility in ob/ob mice. Genes Dev. 16: 1077-1088.

Figure 30:
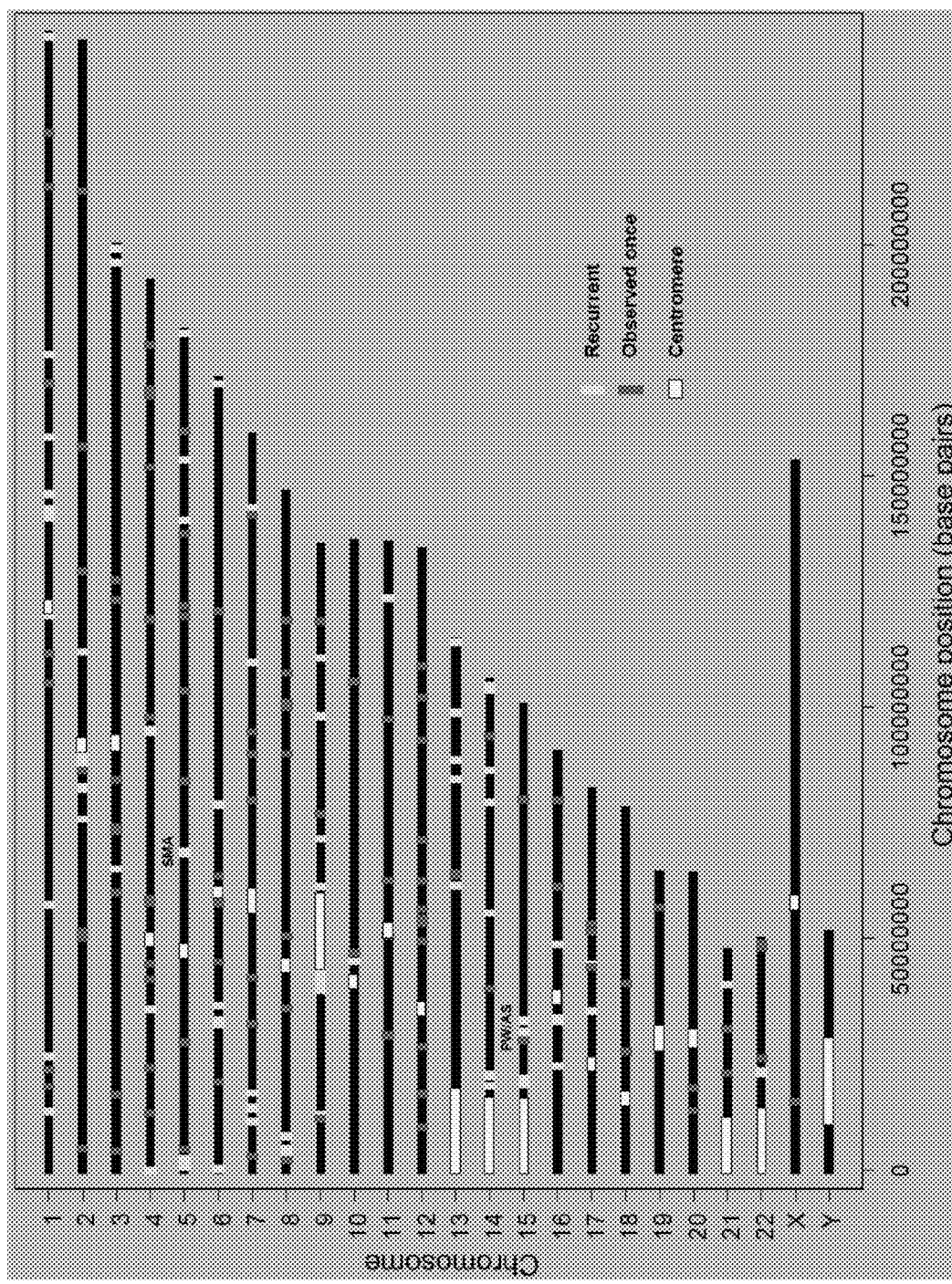
FIGS. 30-35 illustrate the studies of gene copy number variations in diseases other than cancer, such as autism and schizophrenia.
Figure 31:
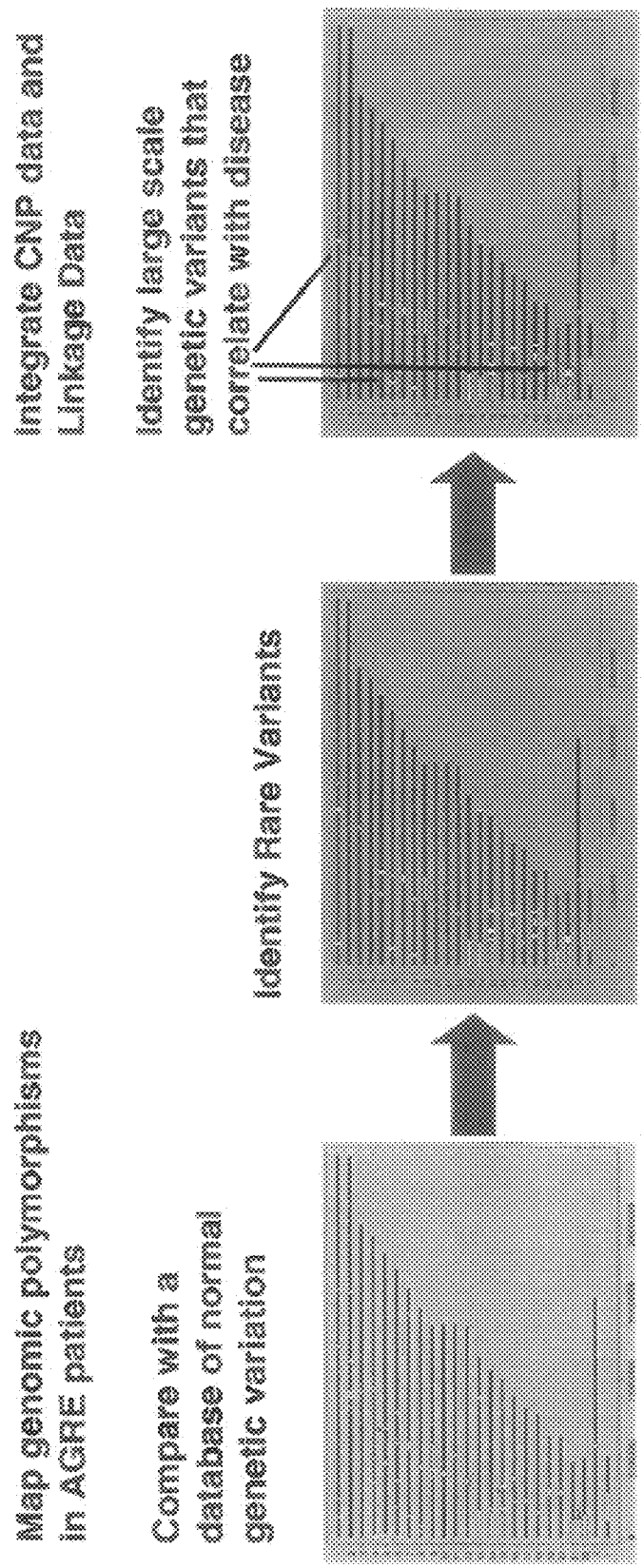
Figure 32:
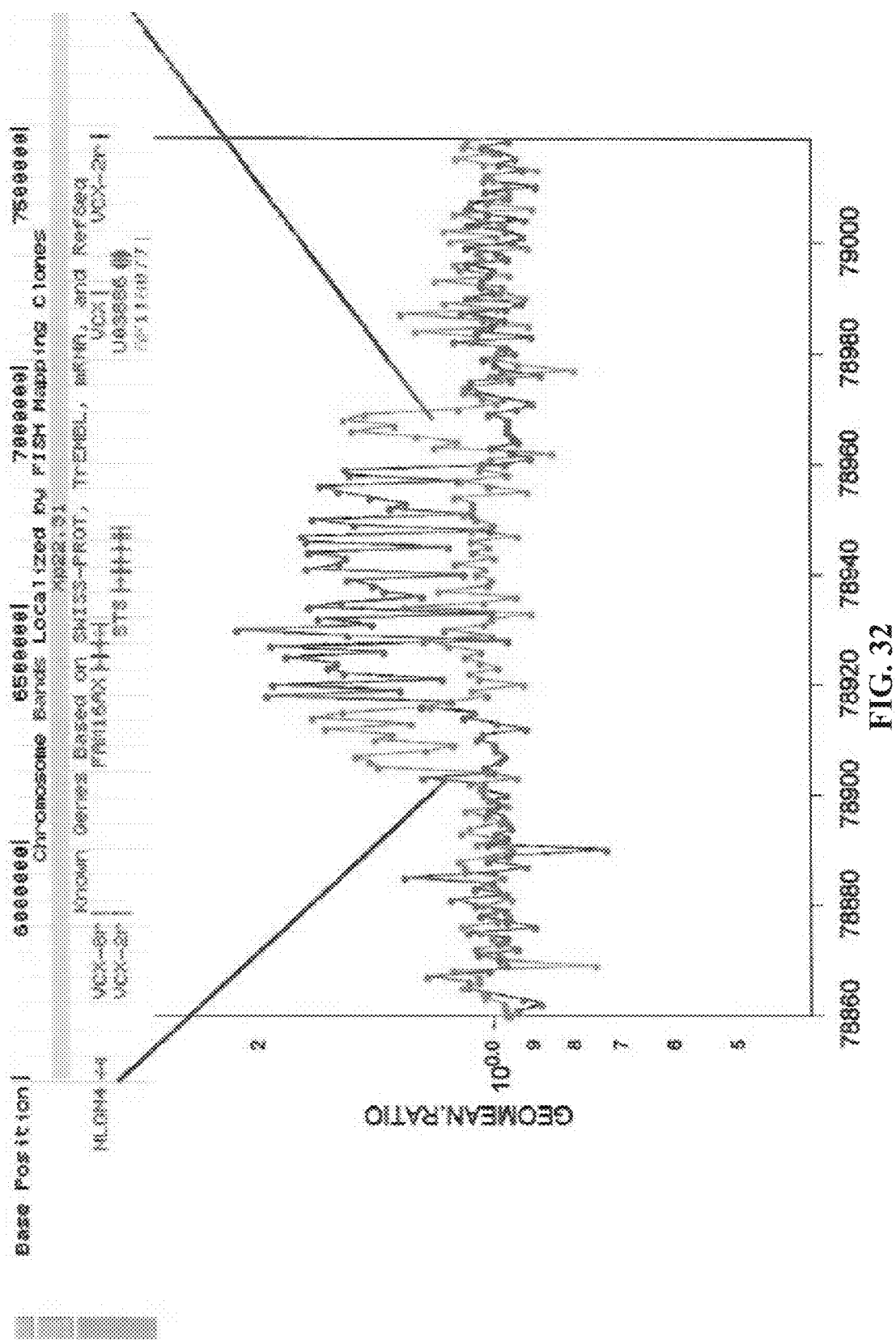
Figure 33:
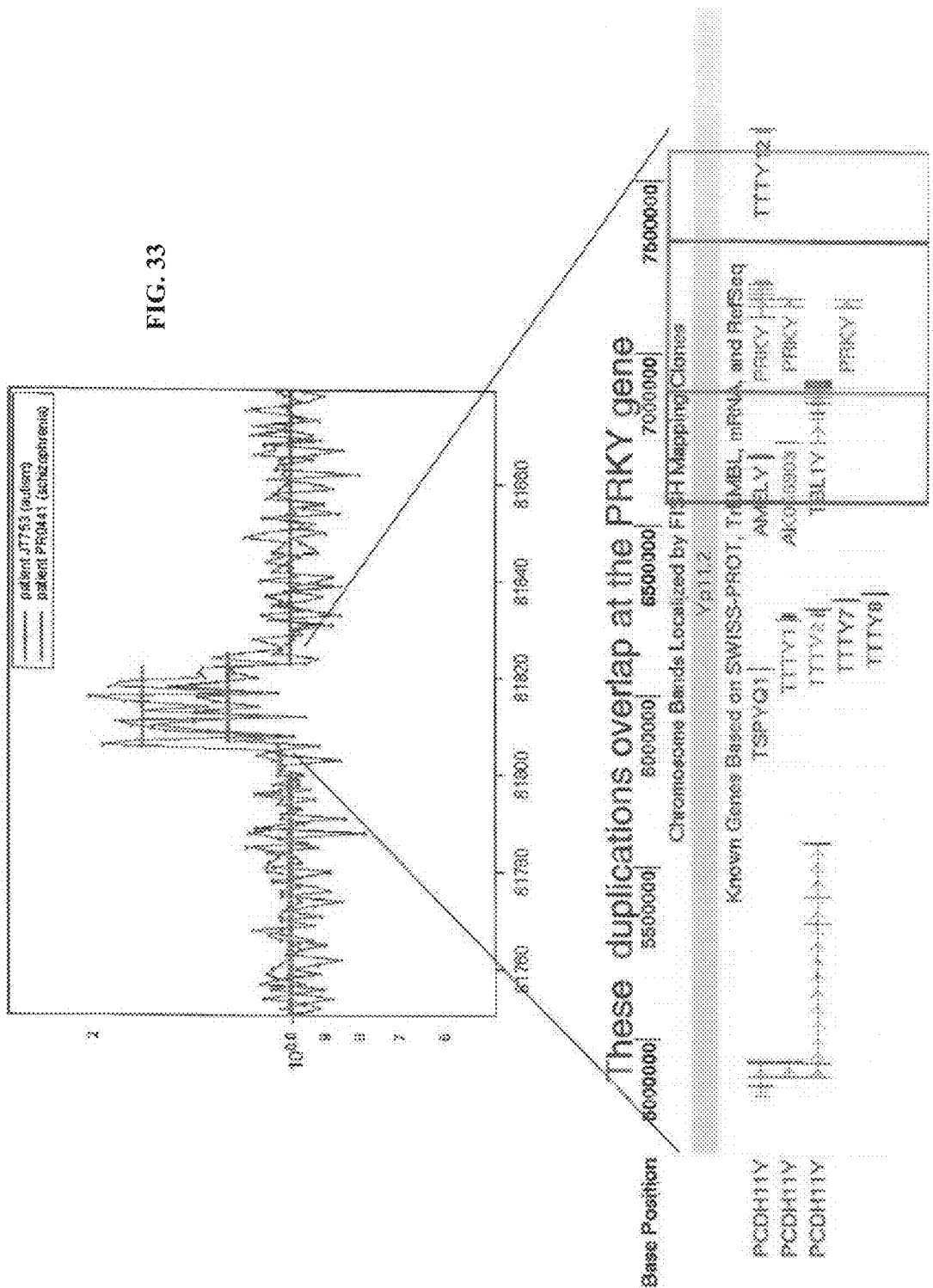
Figure 34:
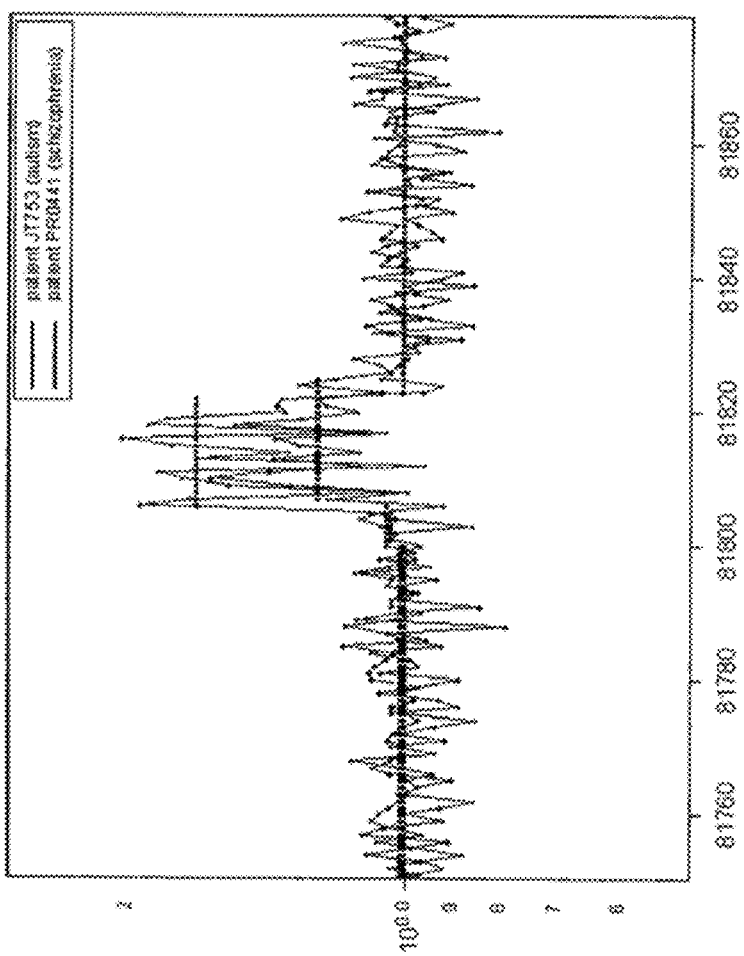
Figure 35:
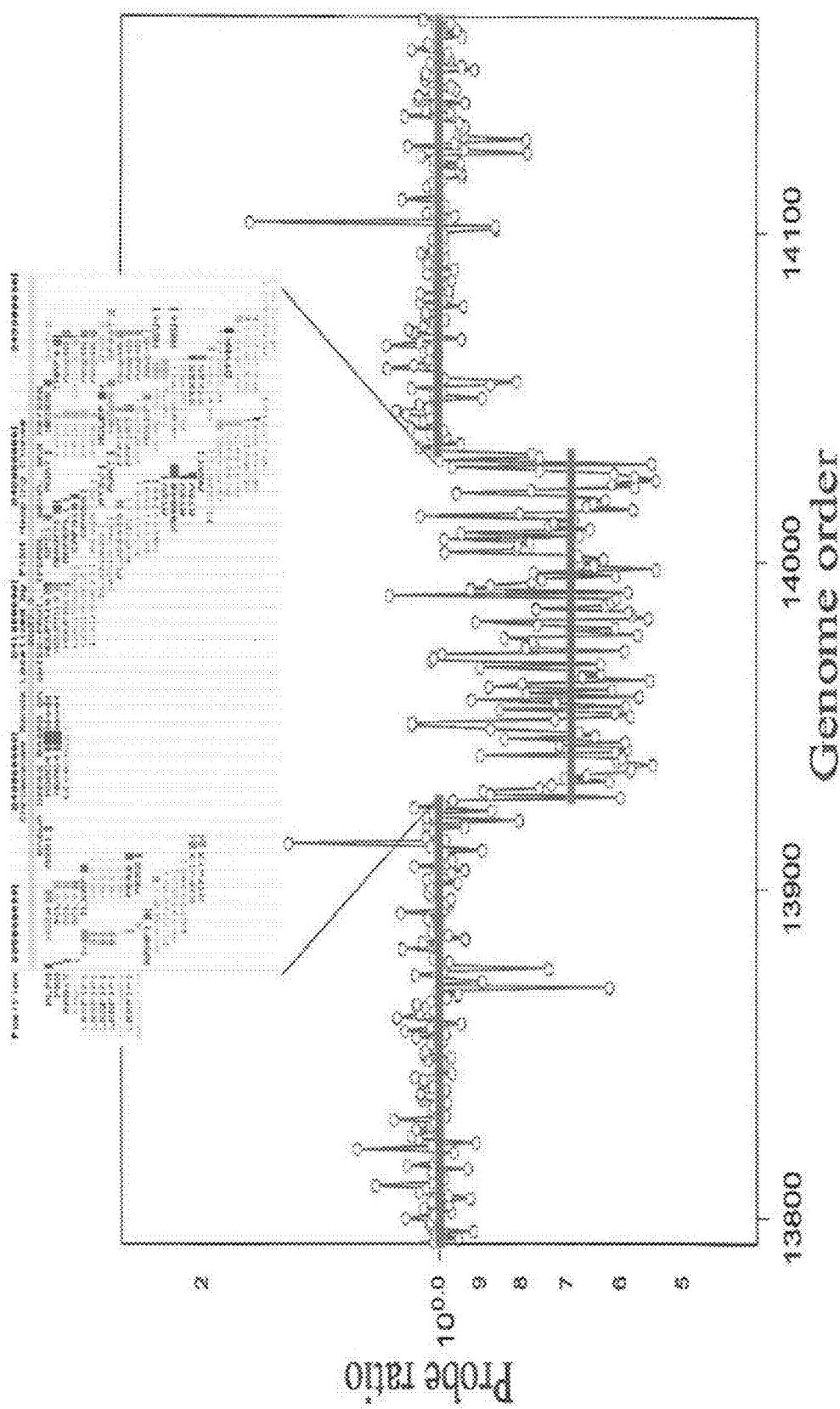

FIGS. 30-35 illustrate the studies of gene copy number variations in other diseases, such as autism and schizophrenia. FIG. 31 illustrates the exemplary steps of the study related to autism: copy number polymorphisms (CNPs) were obtained from genomic samples from the AGRE collection of biomaterials. The CNPs of the patients were then compared against the database of normal genetic variations (e.g., the map of CNPs obtained from 91 control samples as shown in FIG. 30). Rare variants were then identified from that comparison. Large scale CNP variants that correlate with the disease were then identified by integrating the CNP data with the linkage data. FIG. 32 shows a large scale CNP observed in the chromosome band Xp22. FIG. 33 shows a recurrent duplication of the region in chromosome band Yp11.2 in both autism and schizophrenia patient samples. FIG. 34 shows that the variant observed in the chromosome band Yp11.2 appears to be a causal variant, consistent with its familiar inheritance. FIG. 35 shows that a deletion of a region in the chromosome band 2q37.3 observed in a single autism patient. These studies demonstrate that ROMA is a powerful tool to study other diseases that involve genomic rearrangements, e.g., copy number variations. Accordingly, the methods and compositions of the present invention will be useful in analyzing genomic data relating to other diseases, and will provide methods for assigning probabilistic measure and for assessing probable clinical outcome in individual patients with a variety of conditions, diseases and disorders associated with genomic rearrangements.

REFERENCES

Ahr et al. (2002). Identification of high risk breast-cancer patients by gene expression profiling. Lancet 359, 131-132.

Al Kuraya et al. (2004). Prognostic relevance of gene amplifications and coamplifications in breast cancer. Cancer Res 64, 8534-8540.

Albertson, D. G. (2003). Profiling breast cancer by array CGH. Breast Cancer Res Treat. 78, 289-298.

Balmain et al. (2003). The genetics and genomics of cancer. Nature Genetics Supplement 33, 238-244.

Berns et al. (1995). Association between RB-1 gene alterations and factors of favourable prognosis in human breast cancer, without effect on survival. Int. J. Cancer 64, 140-145.

Chunder et al. (2004). Analysis of different deleted regions in chromosome 11 and their interrelations in early- and late-onset breast tumors: association with cyclin D1 amplification and survival. Diagn. Mol. Pathol. 13, 172-182.

Coquelle et al. (1997). Expression of fragile sites triggers intrachromosomal mammalian gene amplification and sets boundaries to early amplicons. Cell 89, 215-225.

Daruwala et al. (2004). A versatile statistical analysis algorithm to detect genome copy number variation. Proc. Natl. Acad. Sci. U.S. A 101, 16292-16297.

DePinho and Polyak (2004). Cancer chromosomes in crisis. Nature Genetics 36, 932-934.

Edén et al. (2004). "Good Old" clinical markers have similar power in breast cancer prognosis as microarray gene expression profilers. Eur. J. Cancer 40, 1837-1841.

Forsslund et al. (1996). Near tetraploid prostate carcinoma. Methodologic and prognostic aspects. Cancer 78, 1748-1755.

Forsslund and Zetterberg (1990). Ploidy level determinations in high-grade and low-grade malignant variants of prostatic carcinoma. Cancer Res 50, 4281-4285.

Garcia et al. (2005). A 1 Mb minimal amplicon at 8p1-12 in breast cancer identifies new candidate oncogenes. Oncogene 24, 5235-5245.

Gisselsson et al. (2000). Chromosomal breakage-fusion-bridge events cause genetic intratumor heterogeneity. Proc Natl Acad Sci USA 97, 5357-5362.

Hellman et al. (2002). A role for common fragile site induction in amplification of human oncogenes. Cancer Cell 1, 89-97.

Jarvinen and Liu (2003). HER-2/neu and topoisomerase IIalpha in breast cancer. Breast Cancer Res Treat. 78, 299-311.

Kallioniemi et al. (1994). Detection and mapping of amplified DNA sequences in breast cancer by comparative genomic hybridization. Proc Natl Acad Sci USA 91, 2156-2160.

Kallioniemi et al. (1992a). Comparative genomic hybridization for molecular cytogenetic analysis of solid tumors. Science 258, 818-821.

Kallioniemi et al. (1992b). Detection of retinoblastoma gene copy number in metaphase chromosomes and interphase nuclei by fluorescence in situ hybridization. Cytogenet. Cell Genet. 60, 190-193.

Kallioniemi et al. (1992c). ERBB2 amplification in breast cancer analyzed by fluorescence in situ hybridization. Proc. Natl. Acad. Sci. U.S. A 89, 5321-5325.

Knoop et al. (2005). Retrospective analysis of topoisomerase IIa amplifications and deletions as predictive markers in primary breast cancer patients randomly assigned to cyclophosphamide, methotrexate, and fluorouracil or cyclophosphamide, epirubicin, and fluorouracil: Danish Breast Cancer Cooperative Group. J. Clin Oncol. 23, 7483-7490.

Kronenwett et al. (2004). Improved grading of breast adenocarcinomas based on genomic instability. Cancer Res 64, 904-909.

Lage et al. (2003). Whole genome analysis of genetic alterations in small DNA samples using hyperbranched strand displacement amplification and array-CGH. Genome Res 13, 294-307.

Loo et al. (2004). Array comparative genomic hybridization analysis of genomic alterations in breast cancer subtypes. Cancer Res 64, 8541-8549.

Lucito et al. (2003). Representational oligonucleotide microarray analysis: a high-resolution method to detect genome copy number variation. Genome Research 13, 2291-2305.

Madjd et al. (2005). Total loss of MHC class I is an independent indicator of good prognosis in breast cancer. Int. J. Cancer 117, 248-255.

McClintock (1938). The production of homozygous deficient tissues with mutant characteristics by means of the aberrant mitotic behavior of ring-shaped chromosomes. Genetics 23, 315-376.

McClintock (1941). The stability of broken ends of chromosomes in *Zea Mays*. Genetics 26, 234-282.

Menard et al. (2001). HER2 as a prognostic factor in breast cancer. Oncology 61, 67-72.

Navin et al. (2006). PROBER: oligonucleotide FISH probe design software. Bioinformatics.

Nessling et al. (2005). Candidate genes in breast cancer revealed by microarray-based comparative genomic hybridization of archived tissue. Cancer Res 65, 439-447.

Olshen et al. (2004). Circular binary segmentation for the analysis of array-based DNA copy number data. Biostat 5, 557-572.

Ormandy et al. (2003). Cyclin D1, EMS1 and 11q13 amplification in breast cancer. Breast Cancer Res Treat. 78, 323-335.

Paik et al. (2004). A multigene assay to predict recurrence of tamoxifen-treated, node-negative breast cancer. N Engl J Med 351, 2817-2826.

Perou et al. (2000). Molecular portraits of human breast tumours. Nature 406, 747-752.

Pollack et al. (2002). Microarray analysis reveals a major direct role of DNA copy number alteration in the transcriptional program of human breast tumors. Proc Natl Acad Sci USA 99, 12963-12968.

Ried et al. (1995). Comparative genomic hybridization of formalin-fixed, paraffin-enbedded breast tumors reveals different patterns of chromosomal gains and losses in fibroadenomas and diploid and aneuploid carcinomas. Cancer Res 5, 5415-5423.

Ried et al. (1997). Tumor cytogenetics revisited: comparative genomic hybridization and spectral karyotyping. J. Mol. Med. 75, 801-814.

Sebat et al. (2004). Large-scale copy number polymorphism in the human genome. Science 305, 525-528.

Shuster et al. (2000). A consistent pattern of RIN1 rearrangements in oral squamous cell carcinoma cell lines supports a breakage-fusion-bridge cycle model for 11q13 amplification. Genes Chromosomes Cancer 28, 153-163.

Slamon et al. (1989). Studies of the HER-2/neu proto-oncogene in human breast and ovarian cancer. Science 244, 707-712.

Sorlie et al. (2001). Gene expression patterns of carcinomas distinguish tumor subclasses with clinical implications. Proc Natl Acad Sci USA 98, 10869-10874.

Sotiriou, C. (2003). Breast cancer classification and prognosis based on gene expression profiles from a population-based study. Proc Natl Acad Sci USA 100, 10393-10398.

Tanaka et al. (2005). Widespread and nonrandom distribution of DNA palindromes in cancer cells provides a structural platform for subsequent gene amplification. Nat. Genet. 37, 320-327.

Tirkkonen et al. (1998). Molecular cytogenetics of primary breast cancer by CGH. Genes Chromosomes Cancer 21, 177-184.

van't Veer et al. (2002). Gene expression profiling predicts clinical outcome of breast cancer. Nature 415, 530-536.

van, d. et al. (1987). Amplification of the neu (c-erbB-2) oncogene in human mammary tumors is relatively frequent and is often accompanied by amplification of the linked c-erbA oncogene. Mol. Cell. Biol. 7, 2019-2023.

Wiedswang et al. (2003). Detection of isolated tumor cells in bone marrow is an independent prognostic factor in breast cancer. J. Clin Oncol. 21, 3469-3478.

U.S. Patent Application Publication No. 20050266444, "Use of representations of DNA for genetic analysis";

U.S. Patent Application Publication No. 20050196799, "Use of representations of DNA for genetic analysis";

U.S. Patent Application Publication No. 20050032095, "Virtual representations of nucleotide sequences";

U.S. Patent Application Publication No. 20040197774, "Representational approach to DNA analysis";

U.S. Patent Application Publication No. 20040137473, "Use of representations of DNA for genetic analysis."

All references cited herein, including the scientific literature, patents, and patent applications are incorporated by references in their entirety.

TABLE 8

Selected genes involved in breast cancer diagnosis or susceptibility

| Gene | chrom | band | probe | chrom. pos | probe | width | | | |
|---|---|---|---|---|---|---|---|---|---|
| ESR1 | 6 | q25.1 | 34559 | 152.16 | 34565 | 152.47 | 6 | | estrogen receptor |
| PGR | 11 | q22-q23 | 54025 | 100.42 | 54029 | 100.54 | 4 | | progesterone receptor |
| HER2/neu | 17 | q21 | 70354 | 35.08 | 70355 | 35.2 | 2 | bracket amp | ERBB |
| TOP2A | 17 | q21-q22 | 70372 | 35.8 | 70373 | 35.84 | 2 | on gene amp | topoisomerase lia |
| ATM | 11 | q22-q23 | 54241 | 107.66 | 54243 | 107.83 | 3 | del | DNA repair |
| CHEK1 | 11 | q24 | 54928 | 124.8 | 54929 | 125.04 | 2 | del | cell cycle checkpoint 2 |
| EGFR1 | 7 | p12 | 36800 | 54.84 | 36806 | 55.06 | 7 | | epidermal growth factor receptor |
| CCND | 11 | q | 53064 | 69.11 | 53065 | 69.18 | 2 | bracket amp | cyclin D1 |
| MYC | 8 | q24.12 | 43267 | 128.75 | 43258 | 128.81 | 2 | bracket amp | myc oncoene |

TABLE 8-continued

Selected genes involved in breast cancer diagnosis or susceptibility

| Gene | chrom | band | probe | chrom. pos | probe | width | | | |
|---|---|---|---|---|---|---|---|---|---|
| TP53 | 17 | p12 | 69589 | 7.5 | 69590 | 7.59 | 2 bracket | del | DNA repair |
| NOG | | | | | | | | | unknown |
| BRCA1 | 17 | q21 | 70461 | 38.42 | 70464 | 38.72 | 4 bracket | | DNA repair, BC susceptibility |
| BRCA2 | 13 | q12.3 | 59605 | 31.77 | 59607 | 31.91 | 3 on gene | | DNA repair, BC susceptibility aka |
| CDKN2A | 9 | p21 | 44459 | 21.96 | 44460 | 22.04 | 2 bracket | del | INK4 |
| CHEK1 | 22 | q11-12 | 78282 | 27.35 | 78283 | 27.47 | 2 bracket | del | cell cycle checkpoint 1 transducer of |
| TOB1 | 17 | q21 | 70693 | 46.24 | 70694 | 46.44 | 2 bracket | amp | ERBB2 |
| CKS1 | 1 | q21.2 | 3850 | 151.75 | 3851 | 151.96 | 2 bracket | amp | cyclin kinase 1 |
| BCAS1 | 20 | q13.2-13.3 | 76564 | 51.99 | 76571 | 52.18 | 8 on gene | | amplified in BC |
| BCAR3 | 1 | p22.1 | 2788 | 93.64 | 2799 | 93.89 | 12 on gene | del | resistance to tamoxifen |
| BCAR1 | 16 | q22-23 | 68998 | 73.8 | 68999 | 73.89 | 2 bracket | | resistance to tamoxifen |
| HOXB grp | 17 | q21.3 | 70615 | 43.75 | 70624 | 44.11 | bracket | | development gene |
| PI3K | 7 | q22.3 | 37878 | 106.1 | 37879 | 106.15 | 2 on gene | | PI3 Kinase |

We claim:

1. A method for determining whether a patient is autistic, comprising:
   (a) obtaining a segmented genomic profile of DNA extracted from a cell of the patient, the segmented genomic profile comprising information about the copy number of a plurality of discrete segments within one or more genomic regions, the one or more genomic regions having been determined by:
      (i) obtaining genomes from a plurality of individuals that have autism;
      (ii) obtaining genomes from a plurality of individuals that do not have autism;
      (iii) identifying one or more genomic regions where copy number polymorphisms in the genomes of individuals that do not have autism are rare relative to copy number polymorphisms in individuals that have autism;
   (b) determining, by computer analysis, a genomic perturbation index value from the segmented genomic profile, wherein said perturbation index value incorporates:
      (i) the number of said discrete segments,
      (ii) the lengths of said discrete segments, or
      (iii) the distribution of the lengths of at least two adjacent segments;
   (c) comparing the perturbation index value of the patient to a perturbation index value determined from a segmented genomic profile of an individual known to have autism, the segmented genomic profile of the individual known to have autism comprising information about the copy number of a plurality of discrete segments within the same one or more genomic regions identified by the process in step (a); and
   (d) classifying the patient as autistic or non-autistic based on the comparison of step (c).

2. The method of claim 1, wherein the segmented genomic profile of the patient is obtained using representational oligonucleotide microarray analysis (ROMA).

3. The method of claim 1, wherein the relative copy number of a discrete segment is set to the measured value of that segment when the measured value of the relative copy number differs from 1 by more than a predetermined fraction of the standard deviation of the relative copy number of that segment in autism-free genomes, and the relative copy number of the discrete segment is set to 1 when the measured value of the relative copy number does not differ from 1 by more than the predetermined fraction of the standard deviation of the relative copy number of that segment in autism-free genomes.

4. The method of claim 1, wherein the one or more genomic regions comprise one or more of Xp22, Yp11.2, and 2q37.3.

* * * * *